US012023250B2

(12) United States Patent
Hjelle et al.

(10) Patent No.: US 12,023,250 B2
(45) Date of Patent: Jul. 2, 2024

(54) CARDIAC TREATMENT SYSTEM AND METHOD

(71) Applicant: DiaxaMed, LLC, Raleigh, NC (US)

(72) Inventors: Aaron J. Hjelle, Andover, MN (US); Tanya Shipkowitz, St. Paul, MN (US)

(73) Assignee: DiaxaMed, LLC, Pinebluff, NC (US)

( * ) Notice: Subject to any disclaimer, the term of this patent is extended or adjusted under 35 U.S.C. 154(b) by 117 days.

(21) Appl. No.: 17/382,941

(22) Filed: Jul. 22, 2021

(65) Prior Publication Data

US 2021/0346160 A1 Nov. 11, 2021

Related U.S. Application Data

(63) Continuation of application No. 16/130,443, filed on Sep. 13, 2018, now Pat. No. 11,109,974.

(60) Provisional application No. 62/558,027, filed on Sep. 13, 2017.

(51) Int. Cl.
*A61F 2/24* (2006.01)
*A61M 60/191* (2021.01)
*A61M 60/289* (2021.01)
*A61M 60/468* (2021.01)
*A61M 60/839* (2021.01)

(52) U.S. Cl.
CPC .......... *A61F 2/2481* (2013.01); *A61M 60/191* (2021.01); *A61M 60/289* (2021.01); *A61M 60/468* (2021.01); *A61M 60/839* (2021.01); *A61F 2002/2484* (2013.01)

(58) Field of Classification Search
CPC .......... A61F 2/2481; A61F 2002/2484; A61M 60/191; A61M 60/289; A61M 60/468; A61M 60/839

USPC .......................................................... 600/37
See application file for complete search history.

(56) References Cited

U.S. PATENT DOCUMENTS

| | | | |
|---|---|---|---|
| 5,702,343 | A | 12/1997 | Alferness |
| 6,508,756 | B1 | 1/2003 | Kung |
| 7,146,226 | B2 | 12/2006 | Lau et al. |
| 8,092,363 | B2 | 1/2012 | Leinsing et al. |
| 9,421,101 | B2 | 8/2016 | Hjelle et al. |
| 11,109,974 | B2 | 9/2021 | Hjelle et al. |
| 2002/0111647 | A1 | 8/2002 | Khairkhahan |
| 2002/0123802 | A1 | 9/2002 | Snyders |
| 2003/0199955 | A1 | 10/2003 | Struble |
| 2004/0010180 | A1 | 1/2004 | Scorvo |

(Continued)

OTHER PUBLICATIONS

Extended European Search Report in Application No. 18855463.8, dated Jul. 20, 2020, 10 pages.

(Continued)

*Primary Examiner* — Sunita Reddy
(74) *Attorney, Agent, or Firm* — Fish & Richardson P.C.

(57) ABSTRACT

Devices and methods for providing localized pressure to a region of a patient's heart to improve heart functioning, including: (a) a jacket made of a flexible biocompatible material, the jacket having an open top end that is received around the heart and a bottom portion that is received around the apex of the heart; and (b) at least one inflatable bladder disposed on an interior surface of the jacket, the inflatable bladder having an inelastic outer surface positioned adjacent to the jacket and an elastic inner surface such that inflation of the bladder causes the bladder to deform substantially inwardly to exert localized pressure against a region of the heart.

16 Claims, 43 Drawing Sheets

(56) References Cited

U.S. PATENT DOCUMENTS

| | | |
|---|---|---|
| 2004/0138521 A1 | 7/2004 | Grabek |
| 2004/0254594 A1 | 12/2004 | Alfaro |
| 2004/0267086 A1 | 12/2004 | Anstadt |
| 2008/0275294 A1 | 11/2008 | Gertner |
| 2009/0062596 A1* | 3/2009 | Leinsing ............... A61F 2/2481 600/16 |
| 2009/0062908 A1 | 3/2009 | Bonhoeffer |
| 2010/0016072 A1 | 1/2010 | Yu et al. |
| 2010/0160721 A1 | 6/2010 | Alferness et al. |
| 2011/0237872 A1 | 9/2011 | Shaolian |
| 2012/0130485 A1 | 5/2012 | Lillehei |
| 2013/0023985 A1 | 1/2013 | Khairkhahan |
| 2013/0138205 A1 | 5/2013 | Kushwaha |
| 2013/0310928 A1 | 11/2013 | Morriss |
| 2014/0107405 A1 | 4/2014 | Hjelle et al. |
| 2014/0107775 A1 | 4/2014 | Hjelle |
| 2014/0194671 A1 | 7/2014 | Wildhirt |
| 2014/0194678 A1 | 7/2014 | Wildhirt |
| 2014/0214159 A1 | 7/2014 | Vidlund |
| 2014/0277424 A1 | 9/2014 | Oslund |
| 2015/0045881 A1 | 2/2015 | Lim |
| 2015/0112421 A1 | 4/2015 | Barnes |
| 2016/0143732 A1 | 5/2016 | Glinnsdale |
| 2016/0213472 A1 | 7/2016 | Kim |
| 2016/0262892 A1 | 9/2016 | Kermode |
| 2016/0346449 A1 | 12/2016 | Roche |
| 2017/0112618 A1 | 4/2017 | Li |
| 2017/0165068 A1 | 6/2017 | Machold |
| 2018/0110468 A1 | 4/2018 | Goldshtein |
| 2019/0000621 A1* | 1/2019 | Wilson ................ A61F 2/2445 |
| 2019/0076250 A1 | 3/2019 | Hjelle et al. |
| 2019/0175339 A1 | 6/2019 | Vidlund |
| 2021/0128304 A1* | 5/2021 | Maimon ............... A61F 2/2466 |
| 2021/0346160 A1 | 11/2021 | Hjelle et al. |

OTHER PUBLICATIONS

International Preliminary Report on Patentability in PCT Appln. No. PCT/US2018/050820, dated Mar. 17, 2020, 7 pages.

International Search Report and Written Opinion in International Application No. PCT/US2018/050820, dated Nov. 19, 2018, 12 pages.

* cited by examiner

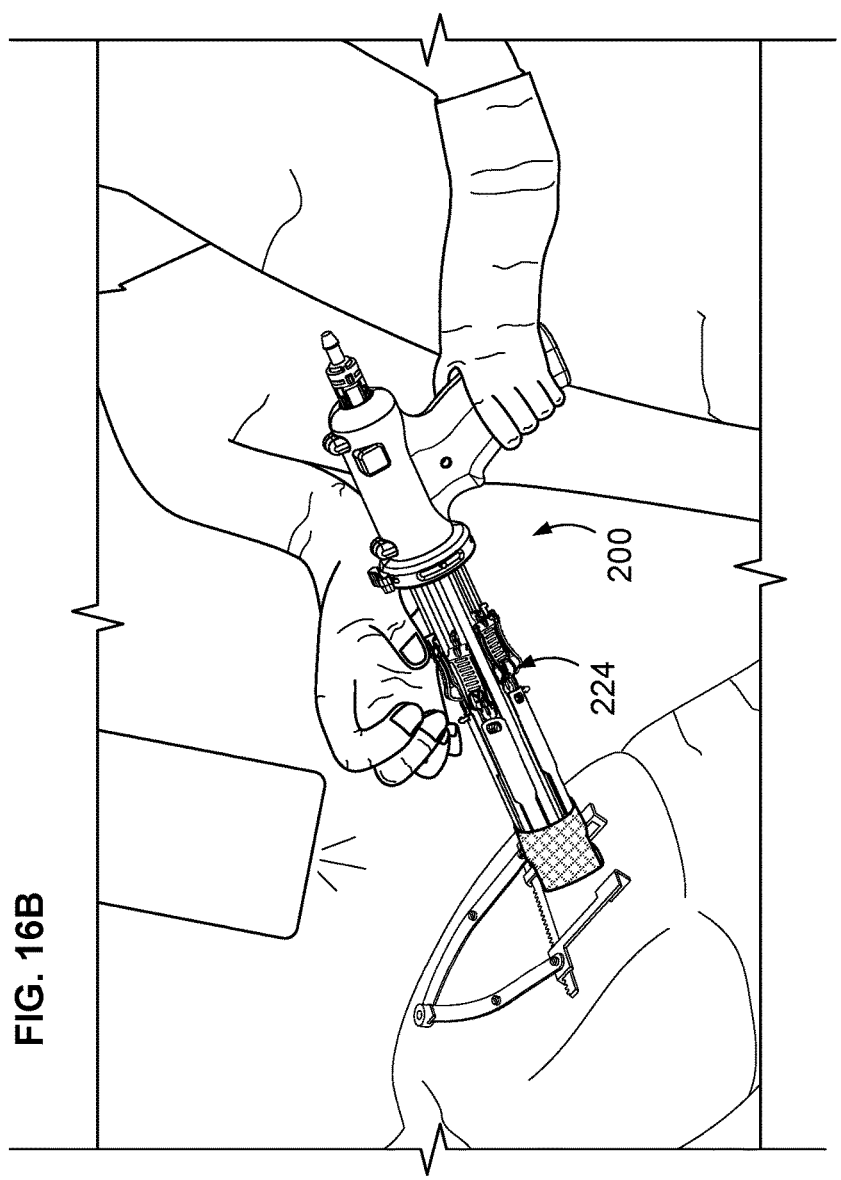
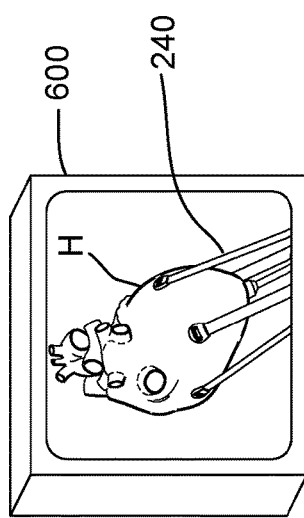
FIG. 16A
FIG. 16B

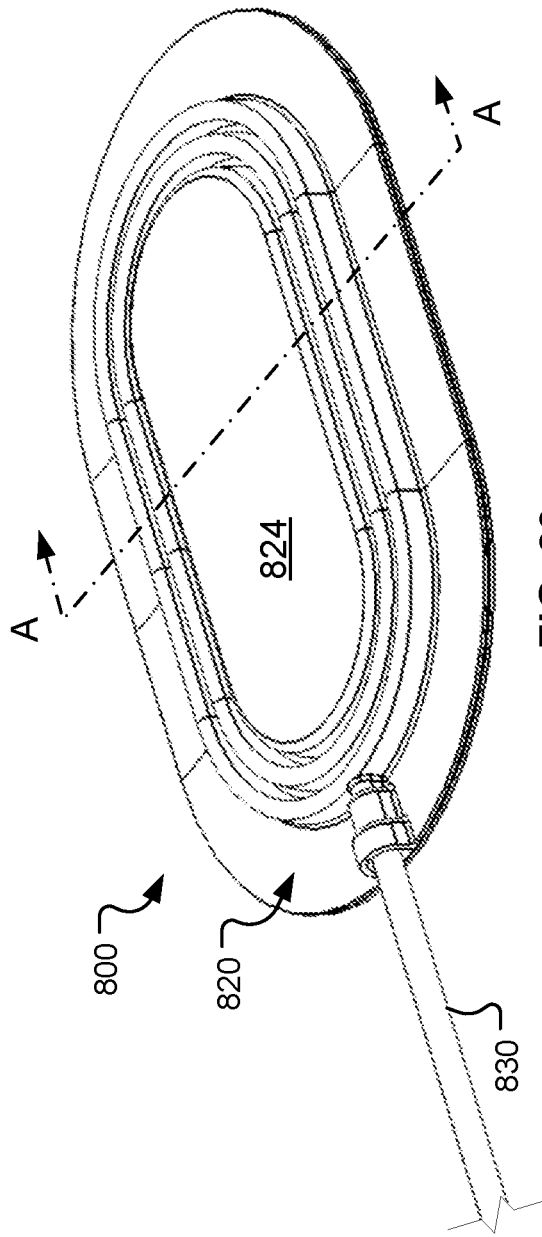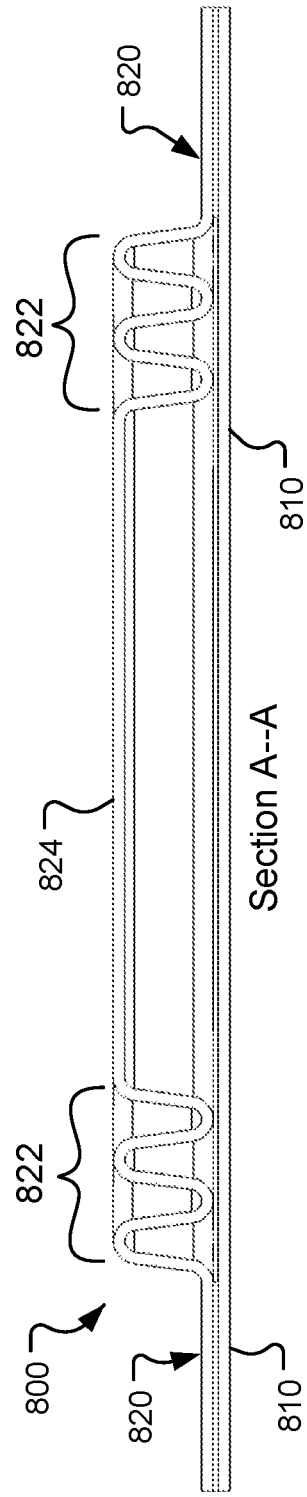

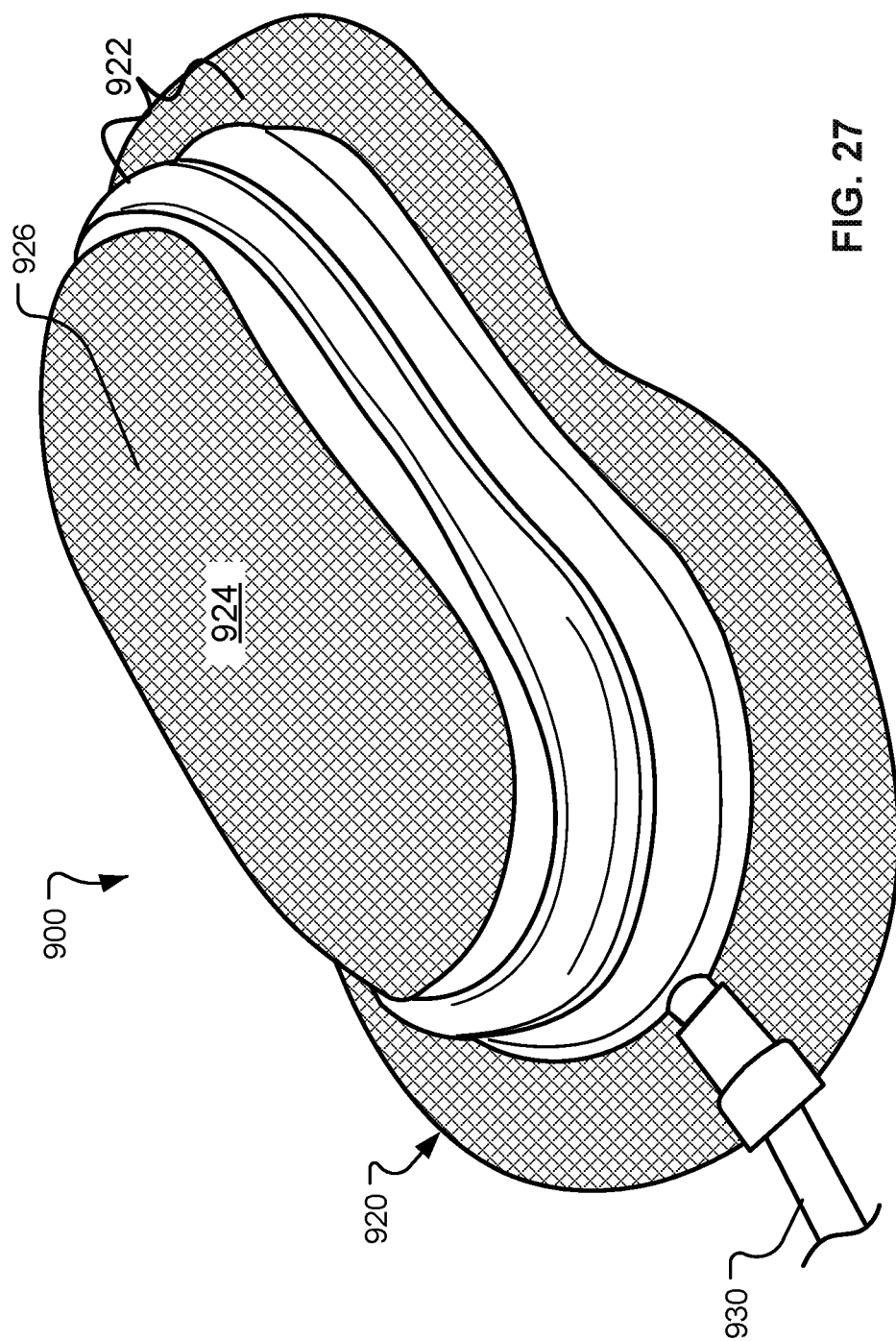

CARDIAC TREATMENT SYSTEM AND METHOD

CROSS REFERENCE TO RELATED APPLICATIONS

This application is a continuation application of U.S. application Ser. No. 16/130,443, filed on Sep. 13, 2018, which claims the benefit of U.S. Application Ser. No. 62/558,027, filed Sep. 13, 2017. The disclosure of the prior applications are considered part of and are incorporated by reference in the disclosure of this application.

TECHNICAL FIELD

The present disclosure relates to medical devices for treating heart diseases and valvular dysfunction, including valvular regurgitation.

BACKGROUND OF THE INVENTION

Various compression-style systems currently exist for treating heart diseases and conditions such as congestive heart disease and valvular dysfunction. These systems typically involve either: (a) jackets that are placed around the heart to limit heart expansion to treat congestive heart disease, or (b) bands that are placed around the heart with fillable chambers to exert localized pressure to re-form the shape of heart valves, for example to minimize valve leakage.

An example of the former is found in U.S. Published Patent Application 2010/0160721 entitled "Cardiac Support Device With Differential Compliance." This device is used to treat congestive heart disease. Congestive heart disease is the progressive enlargement of the heart. This enlargement requires the heart to perform an increasing amount of work. In time, the heart cannot supply an adequate amount of blood, resulting in a patient that is fatigued and in discomfort. The cardiac support device of U.S. Published Patent Application 2010/0160721 limits heart expansion using a flexible jacket positioned around the heart. An example of the second type of system is found in Mardil, Inc.'s U.S. Pat. No. 8,092,363 entitled "Heart Band With Fillable Chambers To Modify Heart Valve Function." This device has fillable chambers that exert inward radial forces on heart valves. The fillable chambers are disposed within inner and outer layers of a silicone rubber band.

SUMMARY

Some embodiments described herein provide a system including an cardiac implant structure configured to be positioned around the exterior of an epicardial surface of a heart. Such a system can be used, for example, to treat various heart conditions, including but not limited to functional mitral regurgitation ("FMR"), tricuspid valve regurgitation, congestive heart failure, or a combination thereof. The implant structure can include a mesh body having a leading hem region configured to elastically flex and engage with an atrial-ventricular groove of the heart, and one or more fillable bladders mounted to the mesh body at one or more predetermined locations so as to provide localized pressure at a targeted surface regions of the heart spaced apart from the atrial-ventricular groove. The implant structure can be equipped with radiopaque markers at selected locations along the leading hem region, along or within the fillable bladders, or a combination thereof, so that the relative positioning of the implant structure and the targeted landmarks of the heart can be readily identified both during and after an implantation procedure. For example, in particular embodiments, the fillable bladders (equipped with markers along a periphery thereof) can be coupled to the mesh body at a specific location to exert a localized pressure on the posterior lateral surface of the heart to thereby deflect the "P2" portion of the posterior leaflet of the mitral valve to treat FMR. Accordingly, the combined components of the implant structure can be configured to apply supporting or deformation forces to multiple targeted regions of the heart in a manner that supports the ventricle walls of the heart, particular valve structures of the heart, and (optionally) the atrial-ventricular groove of the heart.

In one aspect, this disclosure is directed to a cardiac implant for implantation around an exterior of a heart. The implant includes: (i) an implant body comprising a mesh material that is formed into a generally tubular configuration, the implant body comprising a leading end portion defining an open leading end and a trailing end portion defining an open trailing end of a diameter that is less than a diameter of the open leading end; and (ii) a fillable bladder mounted to the implant body and positioned relative to the open leading end such that, when the leading end portion is positioned in an atrial-ventricular groove of the heart, the fillable bladder is positionable on an exterior of a heart wall. The fillable bladder includes side walls with one or more undulations.

Such a cardiac implant may optionally include one or more of the following features. The side walls with one or more undulations may facilitate expansion of the fillable bladder without stretching. The fillable bladder may include: (a) an inner bladder layer positioned with respect to the mesh material of the implant body to face inwardly toward the exterior of the heart wall when the leading end portion is positioned in the atrial-ventricular groove of the heart, and (b) an outer bladder layer position opposite from the inner bladder layer. The inner bladder layer may include the side walls with one or more undulations. The inner bladder layer may include a pressure-exerting surface defined within a periphery of the side walls with one or more undulations. The side walls with one or more undulations may include at least two undulations. The cardiac implant may also include at least a first radiopaque marker positioned along a periphery of the fillable bladder, and at least a second radiopaque marker positioned along a periphery of the leading end portion proximate to the leading open end.

In another aspect, this disclosure is directed to a cardiac implant for implantation around an exterior of a heart. The implant includes: (1) an implant body comprising a mesh material that is formed into a generally tubular configuration, the implant body comprising a leading end portion defining an open leading end and a trailing end portion defining an open trailing end of a diameter that is less than a diameter of the open leading end; and (2) a fillable bladder mounted to the implant body and positioned relative to the open leading end such that, when the leading end portion is positioned in an atrial-ventricular groove of the heart, the fillable bladder is positionable on an exterior of a heart wall. The fillable bladder includes a fabric layer positioned to face inwardly toward the exterior of the heart wall when the leading end portion is positioned in the atrial-ventricular groove of the heart.

Such a cardiac implant may optionally include one or more of the following features. The fillable bladder may include side walls with one or more undulations. The fabric layer may be positioned on a pressure-exerting surface of the inflatable bladder defined within a periphery of the side walls with one or more undulations.

In another aspect, this disclosure is directed to a method of treating heart valve insufficiency. The method includes introducing a cardiac implant into a patient. The implant includes: (a) an implant body formed into a generally tubular configuration, the implant body comprising a leading end portion with an open leading end and a trailing end portion with an open trailing end; (b) a first fillable bladder attached to the implant body; and (c) a second fillable bladder attached to the implant body. The method also includes positioning the cardiac implant so that: (i) the leading end portion is positioned in an atrial-ventricular groove of the heart, (ii) the first fillable bladder is positioned adjacent to a first exterior surface of the heart that is adjacent to a mitral valve annulus, and (iii) the second fillable bladder is positioned adjacent to a second exterior surface of the heart that is adjacent to papillary muscles that control chordae attached to mitral valve leaflets. The method also includes closing the open trailing end of the trailing end portion of the implant body so that the implant body encompasses an apex of the heart.

Such a method of treating heart valve insufficiency may optionally include one or more of the following features. The method may also include filling the first fillable bladder to apply localized pressure on the first exterior surface of the heart so as to modify a shape of the mitral valve annulus; and filling the second fillable bladder to apply localized pressure on the second exterior surface of the heart so as to modify a position of the papillary muscles that control chordae attached to the mitral valve leaflets.

In another aspect, this disclosure is directed to a method of treating heart valve insufficiency. The method includes introducing a cardiac implant into a patient. The implant includes: (A) an implant body formed into a generally tubular configuration, the implant body comprising a leading end portion with an open leading end and a trailing end portion with an open trailing end; and (B) a fillable bladder attached to the implant body, wherein the fillable bladder includes a fabric layer positioned to contact a heart when the implant body is positioned around the heart. The method also includes positioning the cardiac implant so that: (i) the leading end portion is positioned in an atrial-ventricular groove of the heart, and (ii) the fillable bladder is positioned adjacent to an exterior surface of the heart that is adjacent to a mitral valve annulus. The method also includes closing the open trailing end of the trailing end portion of the implant body so that the implant body encompasses an apex of the heart.

Such a method of treating heart valve insufficiency may optionally include one or more of the following features. The method may also include allowing, while the cardiac implant is on the heart, a time period to lapse to allow for growth of epicardial tissue into the fabric layer. The method may also include, after the time period has lapsed, filling the fillable bladder to apply localized pressure on the exterior surface of the heart so as to modify a shape of the mitral valve annulus. In some cases, the time period is at least two weeks. In some cases, the time period is at least four weeks.

These and other embodiments described herein may provide one or more of the following benefits. First, some embodiments include an implant structure having a combination of components that operate to contemporaneously apply forces for supporting or deformation different targeted regions of the heart. For example, the implant structure of particular embodiments of the system described can be configured to contemporaneously apply a localized pressure to a defined area of the posterior lateral surface of the heart while also applying a restraining force of to the ventricle walls of the heart and (optionally) a compressive supporting force to the atrial-ventricular groove of the heart.

Second, some embodiments of the system or method described herein can be used to treat various heart conditions, including but not limited to functional mitral valve regurgitation ("FMR"), tricuspid valve regurgitation, congestive heart failure, or a combination thereof. Upon implantation, implantation structure can apply forces for supporting or deformation regions of the heart in a manner that eliminates or reduces the symptoms of these conditions and that improves blood flow from the heart.

Third, some embodiments of the system or method described herein can include a delivery device configured to advantageously advanced the implant structure to the heart through a relatively small opening of a selected intercostal space proximate to the apex of the heart. Optionally, each delivery device can be configured as a disposable, single-use instrument that is pre-loaded with the implant structure and packaged in a sterilized kit. As such, the clinician can simply select a delivery device bearing the selected size of implant structure (pre-installed on a barrel of the delivery device by during manufacture or assembly) from a plurality of delivery devices in a hospital inventory. After the implant structure in implanted, the delivery device can be conveniently discarded along with other disposables from the operating room.

Fourth, in some embodiments, the implant structure can be arranged on the delivery device in a predetermined orientation relative to the handle of the delivery device. In such circumstances, the fillable bladder of the implant structure may be predisposed for advancement along a targeted side of the heart (e.g., a posterior side) when the handle of the delivery device is held in a selected position external to the opening in the chest, thereby assisting the clinician in aligning the fillable bladder with the targeted surface region of the heart.

Fifth, in particular embodiments, the implant structure can be equipped with radiopaque markers positioned at an advantageous combination of locations along the leading end, along the fillable bladder, or both. As such, during use of the implant structure, the relative positioning of the implant structure and the targeted landmarks of the heart can be readily identified both during and after an implantation procedure.

The details of one or more embodiments of the invention are set forth in the accompanying drawings and the description below. Other features, objects, and advantages of such embodiments will be apparent from the description and drawings, and from the claims.

BRIEF DESCRIPTION OF THE DRAWINGS

FIGS. 16A-16C are perspective views of the advancement of an implant onto the patient's heart, in accordance with some implementations of the method of FIGS. 12A-12C.

FIG. 23 is a perspective view of an example fillable bladder that includes undulated side walls that allow the bladder to expand without distension of the bladder's material.

FIG. 24 is a cross-sectional view of the fillable bladder of FIG. 23 prior to expansion of the bladder.

FIG. 27 is a photograph of an expanded fillable bladder with a textured material on the face of the bladder, in accordance with some implementations.

DETAILED DESCRIPTION OF ILLUSTRATIVE EMBODIMENTS

Figure 1A:
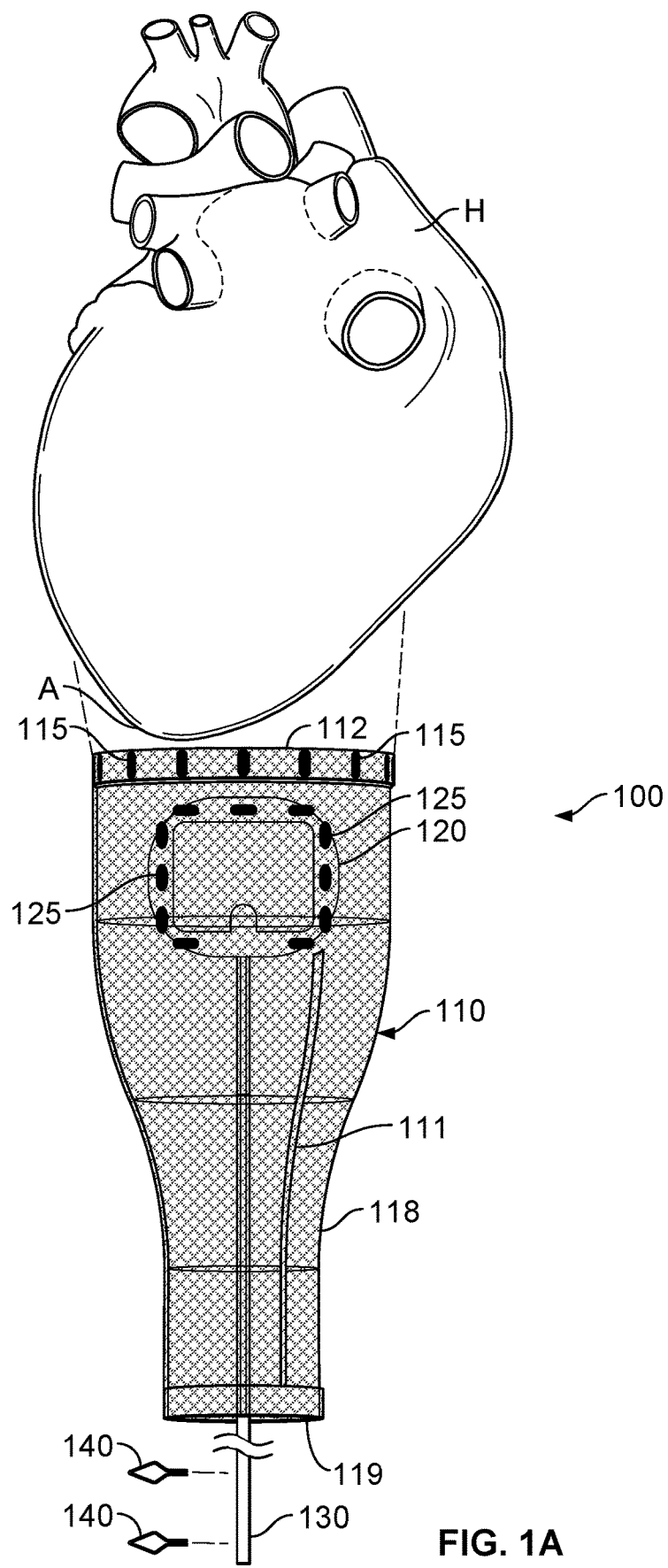
FIG. 1A is an exploded view showing an implant for treating a heart and the heart upon which the implant may be implanted, in accordance with some embodiments.
Figure 1B:
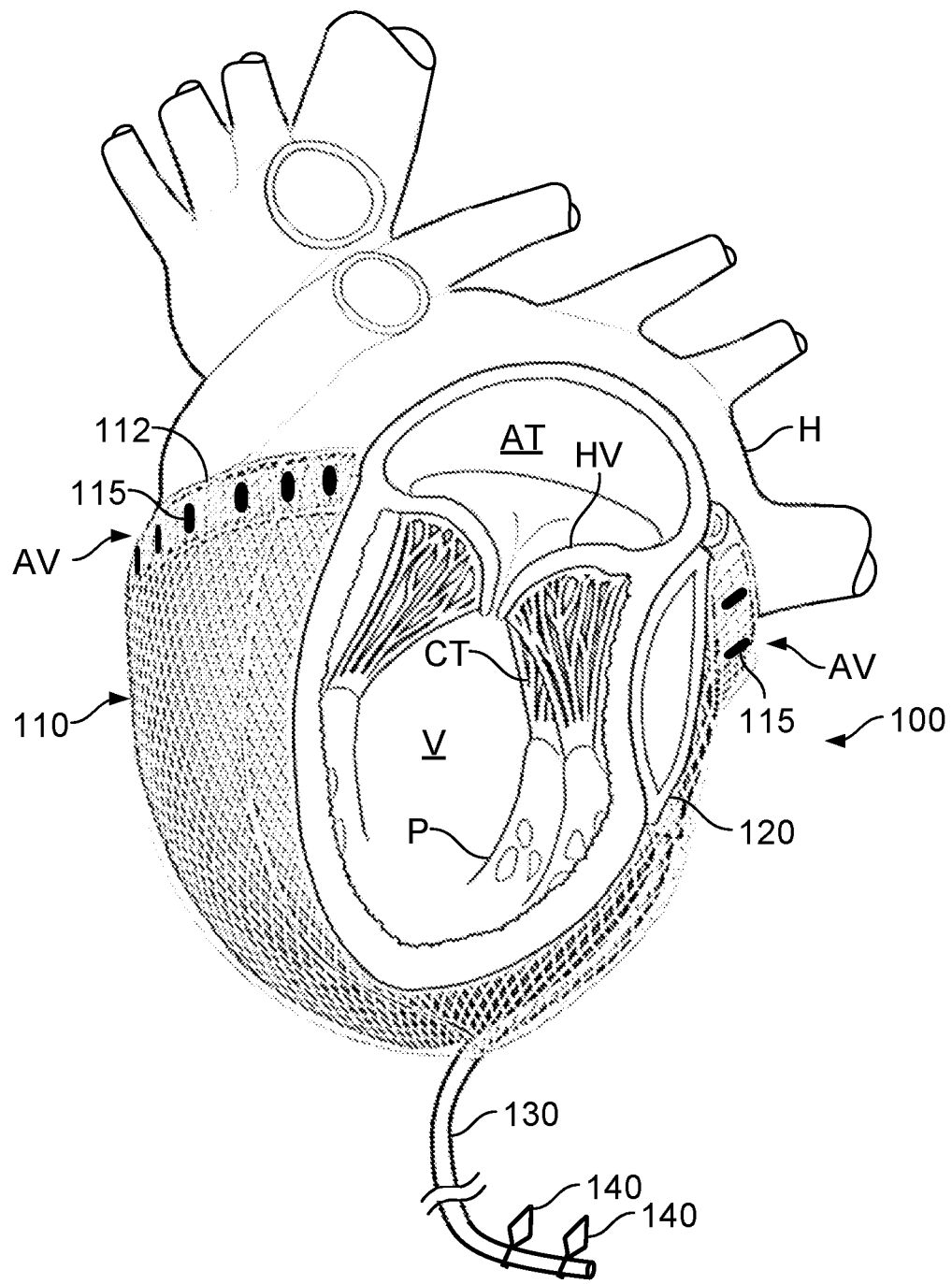
FIG. 1B is a perspective cutaway view of a heart with the implant of FIG. 1A implanted on the heart.

Referring to FIGS. 1A-1B, some embodiments of a system or method described herein include an implant structure configured to be positioned around the exterior of an epicardial surface of a heart H. Such an implant 100 can be used, for example, to treat various heart conditions, including but not limited to FMR, tricuspid valve regurgitation, congestive heart failure, or a combination thereof. For example, in the embodiment depicted in FIG. 1B, the implant 100 can include a fillable bladder 120 coupled to a mesh body 110 at a specific location to exert a localized pressure on the posterior lateral surface of the heart H to thereby deflect the "P2" portion of the posterior leaflet of the mitral valve to treat FMR. The combined components of the implant 100 can be configured to apply supporting or deformation forces to multiple targeted regions of the heart H in a manner that supports the ventricle walls of the heart, particular valve structures of the heart, and (optionally) atrial-ventricular groove of the heart. In use, the implant 100 can be delivered to the heart H through a relatively small opening of a selected intercostal space and thereafter expanded over the apex, ventricles, and atrial-ventricular groove of the heart. In some embodiments, a delivery device (described in detail below) can be operated by a clinician to install the implant 100 on the beating heart H at a selected location, which is verified in real time by the clinician in real using radiopaque markers positioned at an advantageous combination of locations along a hem 113 of the leading end, along the fillable bladder 120, or both.

Referring to FIG. 1A, an implant 100 can be positioned around the external surface of a heart H (e.g., external to the epicardium) to treat various heart conditions. Such heart conditions can include, but are not limited to, functional mitral regurgitation ("FMR"), tricuspid valve regurgitation, and congestive heart failure. FMR is a condition in which the valve structures are normal but the heart is in an abnormal configuration (e.g., an enlarged heart) wherein valve functioning is degraded or not optimal. The implant 100 in this embodiment has a tubular shape that defines an interior space. The implant 100 can be installed onto the heart H such that a portion of the heart H is positioned within the interior space defined by the implant 100. For example, in some implementations the implant 100 is installed so that some or all of the left and right ventricles of the heart H are positioned within the interior space defined by the implant 100. In such an arrangement, the implant 100 surrounds a perimeter of a portion of the heart H. Hence, the implants provided herein, of which implant 100 is one example, may also be referred to herein as jackets. In the depicted embodiment, the implant 100 is of a flexible or expandable tubular design in that it has an open distal end 112 and an open proximal end 119. The open distal end 112 of the implant 100 enables the implant 100 to be implanted by advancing the open distal end 112 around the heart from an inferior (apex) end of the heart to, for example, an atrial-ventricular groove of the heart (described below in connection with FIG. 1B). The open proximal end 119 of the implant 100 is present in the depicted embodiment to accommodate a minimally invasive delivery device (described below in connection with FIGS. 6A-6C) with one or more members that extend through the open proximal end 119 and attach to the open proximal end 119 of the implant 100 so as to push the distal end 112 of the implant 100 over and beyond the apex of the heart H and into, for example, the atrial-ventricular grove, as will be shown and described below.

In some embodiments, the implant 100 can include a tubular mesh body 110. The tubular mesh body 110 may include one or more seams 111 that are formed as a result of the construction of the tubular mesh body 110. For example, the one or more seams 111 may be formed as a result of making the mesh body 110 into a tube, as a result of creating contours within the mesh body 110, or as a result of creating hemmed ends of the mesh body 110. However, seams are not a requirement in all embodiments of the implant described herein. That is, in some alternative embodiments, the implant can be made with a seamless construction.

Still referring to FIG. 1A, a fillable bladder 120 is attached to the mesh body 110. The fillable bladder 120 may also be referred to herein as an inflatable bladder. In this embodiment, the fillable bladder 120 is affixed on an interior surface of the mesh body 120. Hence, when the implant 100 is installed onto the heart H (e.g., between the pericardium and epicardium), the fillable bladder 120 is positioned adjacent to and makes contact with the external surface of the heart H. In some alternative embodiments, the fillable bladder 120 can be affixed on the exterior of the mesh body 110, or installed in or between layers of material of a multi-layered mesh body. In further alternative embodiments, multiple fillable bladders 120 are affixed on a single mesh body 120.

An inflation tube 130 is in fluid communication with the fillable bladder 120. As described further herein, the inflation tube 130 provides a lumen through which an inflation fluid (e.g., saline or another biocompatible liquid) is transferred to thereby inflate or deflate the fillable bladder 120. In some embodiments, one or more ligation clips 140 are used to seal the inflation tube 130 after the fillable bladder 120 has been filled with an inflation fluid to a desired extent. As an alternative to the ligation clips 140, the inflation tube 130 can be doubled over to seal the inflation tube 130, and the configuration can be secured by tightly wrapping the doubled-over portion with a suture. In another alternative, a plug can be inserted into the end of the inflation tube 130. Other techniques and a combination of techniques can also be used to seal the proximal region of inflation tube 130. With the one or more ligation clips 140 installed on the inflation tube 130, the selected amount of inflation fluid can be maintained within the fillable bladder 120. With the fillable bladder 120 thusly inflated, the expansion of the bladder 120 causes a localized pressure to be applied to a selected exterior surface of the heart H (e.g., along an exterior of the epicardium), to thereby treat a heart condition.

The implant 100 can also include a plurality of radiopaque markers 115 and 125 in selected locations that provide a number of benefits to a surgeon during and after implantation. Such radiopaque markers 115 and 125 can facilitate radiographical visualization of the implant 100 during a minimally invasive implantation process. For example, in some instances the implant 100 is installed with the assistance of fluoroscopy. Other imaging modalities may also be used, such as echocardiography, MRI, and the like. Using imaging systems in conjunction with radiopaque markers 115 and 125, the implant 100 can be positioned onto the heart H, and oriented in relation to anatomical features of the heart H, as desired. In some implant procedures, contrast agent solutions are injected into the heart, or within the pericardial space, to enhance the radiographical visualization of anatomical features of the heart H on which an implant 100 is to be installed. The radiopaque markers 115 and 125 can comprise materials such as, but not limited to, tantalum, platinum, tungsten, palladium alloys, and the like.

In the embodiment shown, a first group of radiopaque markers 115 are positioned at a leading end 112 of the mesh body 110. The leading end 112 in this embodiment includes a circumferential hem region that defines the distal end opening 117 (refer to FIG. 2A). As described further herein, in some embodiments the radiopaque markers 115 are used to facilitate the installation of the implant 100 in relation to the heart H such that the leading end 112 is positioned in the atrial-ventricular groove of the heart H. A second group of radiopaque markers 125 are positioned on the implant 100 to identify the location of the fillable bladder 120 on the mesh body 110. For example, the second group of markers 125 can be mounted along at least a portion of a periphery of the fillable bladder 120. Using the radiopaque markers 125, the fillable bladder 120 can be positioned at a target location on the exterior surface of the heart H. For example, as will be described further herein, in some instances the fillable bladder 120 may be configured for installation at a selected position on the surface of the heart H (for example, on a posterior wall of the heart adjacent the mitral valve) so that the fillable bladder 120 will exert a localized pressure to induce the reshaping of a portion of the heart H when the fillable bladder 120 is inflated. In the case of positioning on a posterior wall of the heart adjacent the mitral valve, the fillable bladder 120 provides localized pressure that in turn is applied to a posterior portion of the mitral valve annulus, thus bringing the leaflets of the valve into closer proximity with one another and addressing a mitral valve regurgitation problem (described, for example, in more detail below in connection with FIG. 1B). While this embodiment includes the radiopaque markers 115 and 125 located near the leading end 112 and fillable bladder 120 respectively, in other embodiments radiopaque markers may be included at other locations instead of, or in addition to, the locations of the radiopaque markers 115 and 125.

Still referring to FIG. 1A, the mesh body 110 of the implant 100 also includes a trailing end portion 118 that is located opposite of the leading end 112. The trailing end portion 118 may also be referred to herein as the proximal region. The trailing end portion 118 can provide the implant 100 with an axial length such that, when the implant 100 is installed on the heart H, excess mesh material extends proximally away from the apex A of the heart H. As described in detail below, after installing the implant 100 onto the heart H, an excess length portion of the trailing end portion 118 can be optionally trimmed off of the implant 100. Thereafter, in some implementations the trimmed end of the mesh body 110 at the trailing end portion 118 is gathered or cinched around the apex A and closed using one or more sutures, clips, or the like. This implementation of providing a post-installation closure to the trimmed end of the mesh body 120 may be preferred in some cases, for example, to prevent the proximal end of the implant 100 from migrating, after implantation, distally toward the distal end of the implant 100, which may otherwise occur given the movement of the heart and the lesser degree anchoring of the implant 100 immediately after installation (before fibrosis and tissue ingrowth between the implant 100 and the heart tissue such as the epicardium, pericardium, or both).

Referring now to FIG. 1B, the implant 100 can be installed on the heart H so as to surround an inferior portion of the heart H, including at least a portion of the left and right ventricles V. In some embodiments, at least a portion of the leading end 112 is positioned in the atrial-ventricular groove of the heart H. By positioning the leading end 112 in the atrial-ventricular groove AV, the implant 100 can maintain a desired positioning in relation to the heart H by taking advantage of the contours of the heart H. In this embodiment, the implant 100 is installed in the pericardial cavity. That is, during the implantation process, the pericardium is opened and the implant 100 is installed over an exterior of the epicardium of the heart H and internal to the pericardium of the heart H. Thereafter, the pericardium is closed to thereby contain the implant 100 in the pericardial cavity. Over time, a fibrosis or tissue ingrowth process may occur to cause the mesh body 110 to be anchored to the epicardium, the pericardium, or a combination thereof. Optionally, in some instances, one or more sutures may be used to attach the mesh body 110 to the epicardium at the time of implantation.

In the depicted embodiment, the fillable bladder 120 is attached to an interior surface of the mesh body 110 such that, when the implant 100 is implanted, the fillable bladder 120 is positioned between the mesh body 110 and the heart H. In other words, a surface of the fillable bladder 120 is in direct contact with a surface of the heart H (e.g., an exterior epicardial surface in this embodiment). When an inflation fluid is supplied under pressure into the fillable bladder 120 (e.g., from a syringe device coupled to the inflation tube 130), the fillable bladder 120 expands from a collapsed condition to an operative condition to thereby exert a localized pressure to a targeted portion of the surface of the heart H. A target location for applying the localized pressure can be strategically selected to induce a desired effect to the patient's heart H. For example, as shown, a localized pressure can be exerted at a location on the heart H that causes a deflection to an annulus of a heart valve HV, such as a mitral valve or a tricuspid valve. In that manner, some types of valvular regurgitation can be treated. In a particular example, the fillable bladder 120 can be positioned to exert a localized pressure on the posterior lateral surface of the heart H to thereby deflect the "P2" portion of the posterior leaflet of the mitral valve to treat FMR. In another example, other areas on the exterior surface of the ventricles V can be targeted for the exertion of a localized pressure from the fillable bladder 120. In some such examples, the papillary muscles P are advantageously deflected. In certain instances, such deflecting of the papillary muscles P, and the chordae tendineae CT confluent therewith, can also treat valvular regurgitation.

While the examples of FIGS. 1A and 1B depict an implant 100 having a single fillable bladder 120, it should be understood that in other embodiments two or more fillable bladders may be included on a single implant device. In the depicted embodiment, the fillable bladder 120 is pre-attached to the mesh body 110. In some embodiments, one or more fillable bladders are separate from the mesh body, and are attached to the mesh body or positioned at a desired location inside the mesh body during the implantation procedure either before or after the mesh body has been installed on the heart. For example, the mesh body may be installed on the heart H of a patient, and subsequently one or more fillable bladders can be positioned at target locations in relation to the mesh body and then optionally attached to the mesh body in situ.

In some embodiments, the mesh body 110 is sized to snugly fit on the heart H, but not so tight as to cause a significant increase in left ventricular pressure during diastole or obstructions to the coronary arteries or other vessels such as the coronary sinus. That is, in these embodiments, the mesh body 110 is designed to be highly compliant to the shape of the heart H, and adaptable to gently conform with the distension of the myocardium as the heart H performs pumping actions.

Figure 2A:
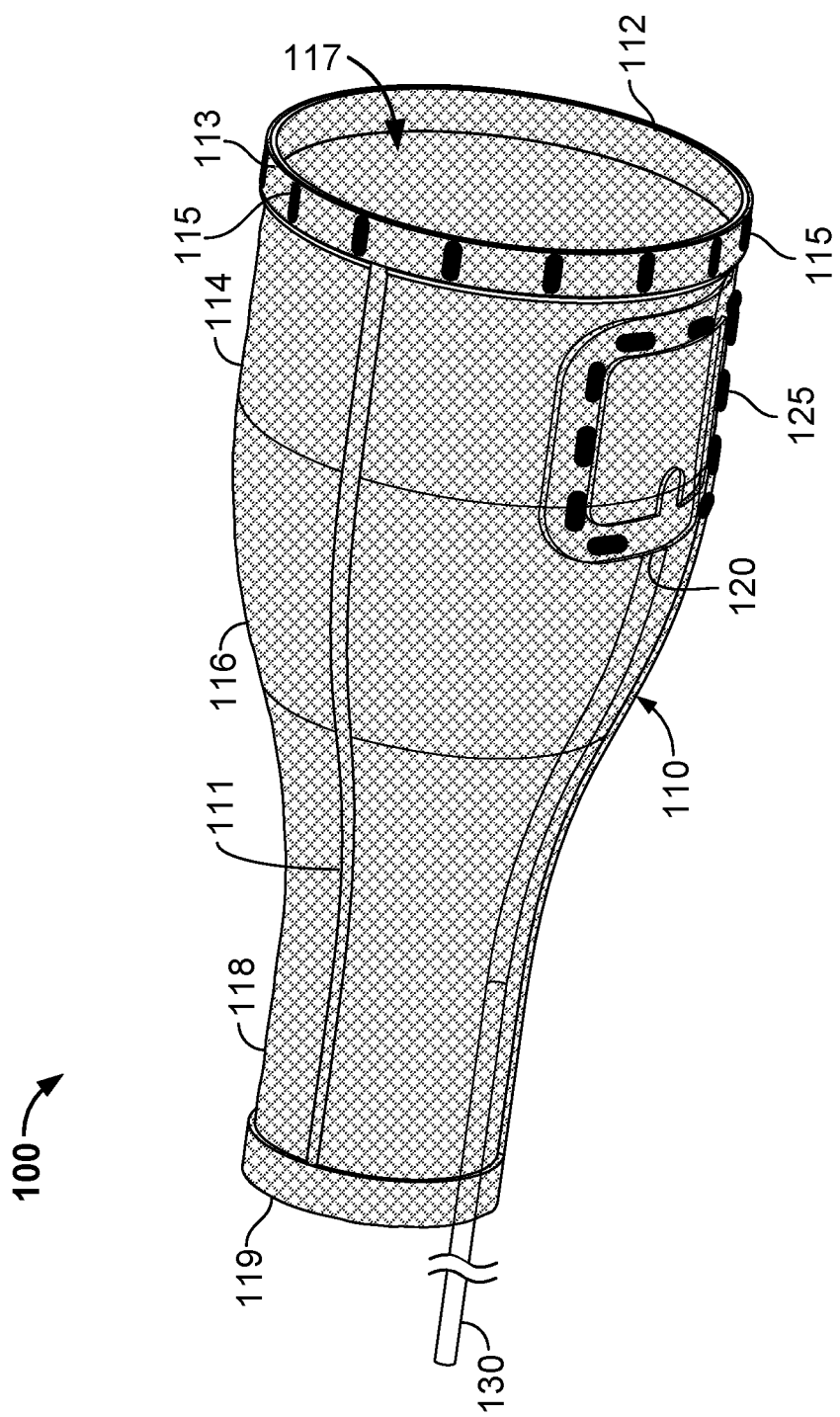
FIG. 2A is a perspective side view of an implant for treating a heart, in accordance with some embodiments.
Figure 2B:
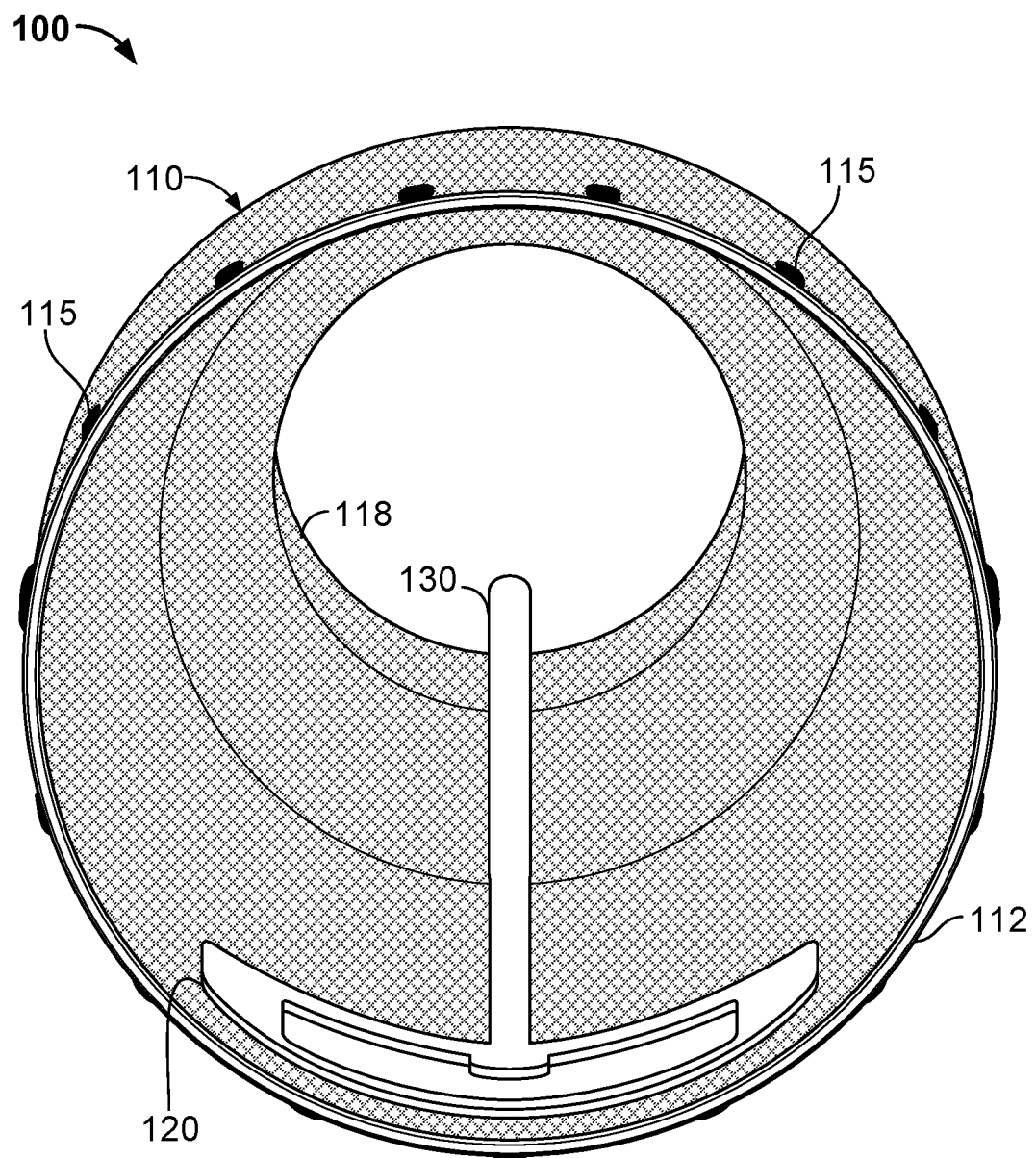
FIG. 2B is a perspective end view of the implant of FIG. 2A showing a fillable bladder in a deflated configuration.
Figure 2C:
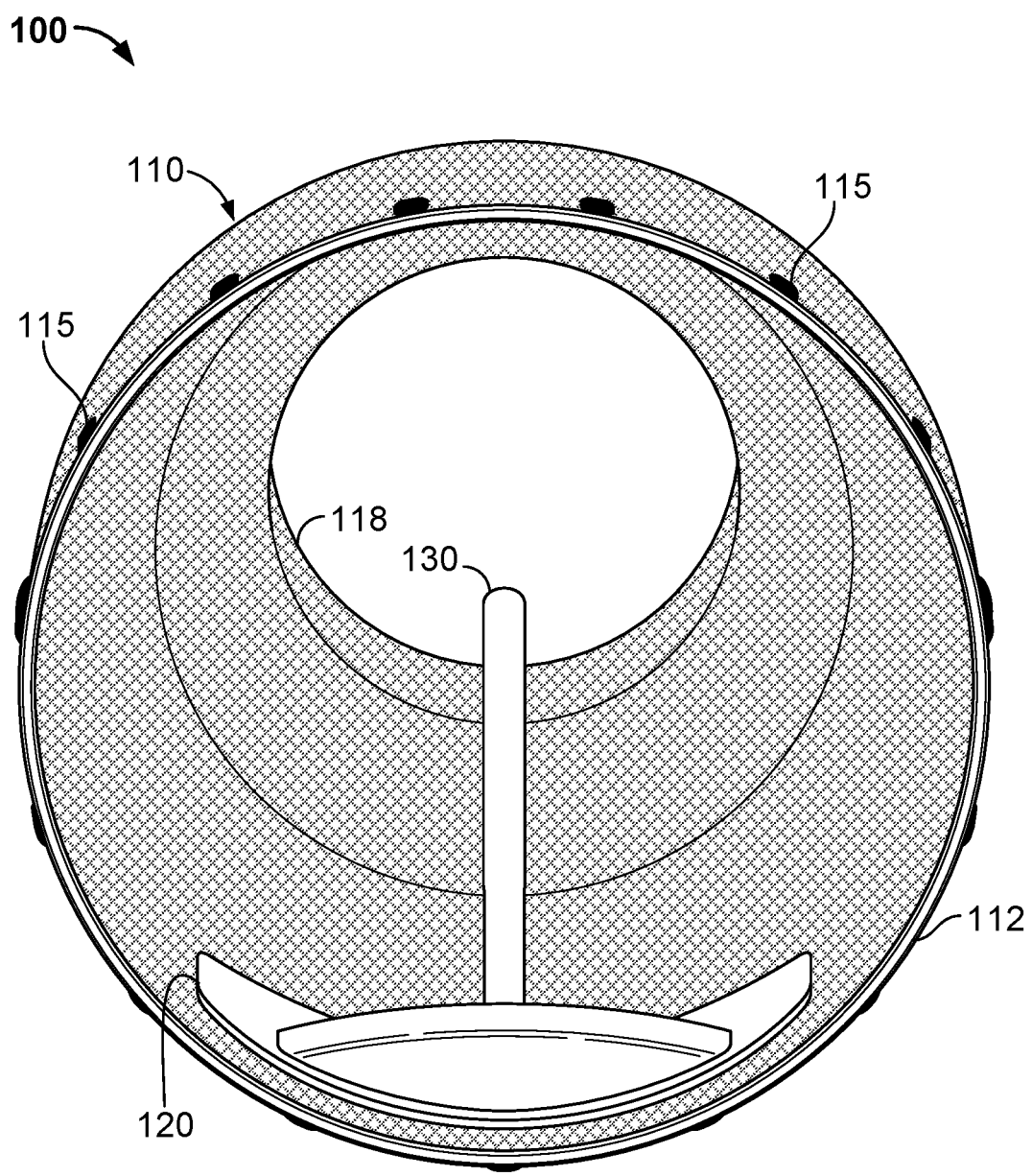
FIG. 2C is a perspective end view of the implant of FIG. 2A showing the fillable bladder in an inflated configuration.

Referring to FIGS. 2A-2C, the implant 100 of FIG. 1 will now be described in greater detail. FIG. 2A provides a perspective view illustrating the tubular shape and other features of the implant 100. FIGS. 2B and 2C provide end perspective views to illustrate, for example, the interior surfaces of the implant 100 and the fillable bladder 120. For instance, FIG. 2B depicts the fillable bladder 120 in a deflated configuration, while FIG. 2C depicts the fillable bladder 120 in an inflated configuration.

In some embodiments, the material of the mesh body 110 is constructed from a knitted, biocompatible material. In particular embodiments, the knitted material is made using a construction known as "Atlas knit." The Atlas knit is a knit of fibers having directional expansion properties. More specifically, the knit, although formed of generally inelastic fibers, permits a construction of a flexible fabric at least slightly expandable beyond a rest state. The fibers of the mesh fabric are woven into two sets of fiber strands. The strands are interwoven to form the fabric with a first set of strands generally parallel and spaced-apart and with a second set of strands generally parallel and spaced-apart. For purposes of illustration in FIGS. 2A-2C, the mesh fabric is schematically shown herein as a diamond-shaped open cell mesh fabric having diagonal axes, but it should be understood from the description herein that the mesh fabric may have a different appearance. FIGS. 1A and 2A illustrates the knit mesh body 110 in a generally unexpanded state, whereas FIG. 1B illustrates the knit mesh body 110 is an expanded state. In some embodiments, the mesh body 110 is made of a Denier polyester. In other embodiments, the mesh body 110 can be made of other suitable biocompatible materials including polytetrafluoroethylene (PTFE), expanded PTFE (ePTFE), polypropylene, stainless steel, and the like, or combinations thereof. Other types of knitting processes can also be used to construct the implants provided herein. Further, other construction techniques in addition to knitting are envisioned. For example, some or all parts of the body 110 may be woven, braided, made of tubing or an expanded tubing, and the like.

In some embodiments, the mesh body 110 includes a leading end portion 114, a transition portion 116, and a trailing end portion 118. Each of the three portions 114, 116, and 118 are tubular. That is, the mesh material used to construct the portions 114, 116, and 118 is arranged to define open interior spaces. In this embodiment, the mesh body 110 is configured to provide a cross-section shape (e.g., perpendicular to a central axis of the implant 100) that is circular in each of the three portions 114, 116, and 118, and the portions 114 and 118 may be generally cylindrical along a majority of their respective axial lengths. In other embodiments, the materials can be arranged to define other cross-sectional shapes. In other embodiments, other configurations of implant body shapes are envisioned, and such portions 114, 116, and 118 are not necessarily implemented in all embodiments described herein. In some embodiments, the construction of the mesh body 110 may include one or more seams 111 as a result of sewing the mesh material into the desired shape. In some embodiments, the construction of the mesh body 110 may be seamless.

Still referring to FIGS. 2A-2C, in this embodiment, the generally cylindrical leading end portion 114 provides the largest diameter of the three portions 114, 116, and 118 (when the implant 100 is in a non-stressed state prior to implantation). In some embodiments, the three portions 114, 116, and 118 are not separately constructed regions, but rather are defined regions of a device constructed from a single piece of mesh material. In other embodiments, the three portions 114, 116, and 118 may be separately constructed and attached together to form the final implant construction. The trailing end portion 118 provides the smallest diameter of the three portions 114, 116, and 118 (when the implant 100 is in a non-stressed state prior to implantation). The transition portion 116 extends between a proximal end periphery of the leading end portion 114 and a distal end periphery of the trailing end portion 118. The transition portion 116 has diameter variance from its distal end portion to its proximal end portion. That is, the transition portion 116 may be tapered (providing either a linear taper or a curved taper), extending proximally from the leading end portion 114 while decreasing in diameter to join with the distal end periphery of the trailing end portion 118. In some embodiments, the transition portion 116 comprises a frustoconical shape. In particular embodiments, some or all of the transitional region 116 has a radiused profile to provide smooth transitions to the leading and trailing portions 114 and 118.

In some embodiments, at least a portion of the leading end portion 114 has a diameter and construction for positioning around a heart in the atrial-ventricular groove AV of the heart H. For example, a hem 113 comprising an elastic band member may be configured for positioning around an atrial-ventricular groove AV (refer to FIG. 1B), to thereby releasably affix the leading end 112 to the heart H. The diameter of the hem 113 (including the elastic band member) may be selected in relation to the size of the heart of a patient. The selected diameter of the hem 113, at rest, will be smaller than the perimeter of the heart at the atrial-ventricular groove, to provide an interference fit therebetween. The high compliance and elasticity of the hem 113 (including the elastic band member) facilitates an interference fit that is effective for maintaining the implant 100 in the targeted position on the heart H while not detrimentally constricting the heart and vessels on the outside of the heart such as the coronary artery or coronary sinus over which the hem 113 may be positioned when the implant 100 is implanted.

Portions of the leading end portion 114, other than the hem 113, are configured for circumferentially encompassing upper portions of the heart ventricles. In addition, some or all of the transition portion 116 may be configured for circumferentially encompassing other portions the heart ventricles. Most or all of the trailing end portion 118 may be configured to extend proximally from the apex of the heart when the leading end 112 is positioned in the atrial-ventricular groove. After installation of the implant 100 on a heart, some or all of the trailing end portion 118 may be trimmed away and removed from the implant 100. Thereafter the trimmed proximal end of the implant 110 may gathered or cinched and closed around the apex of the heart. Closing the proximal open end prevents the implant 100 from migrating toward the superior regions of the heart after implantation. In this manner, the implant 100 can be tailored to fit the patient-specific size and contours of the heart on which the implant 100 is installed.

Multiple sizes of implants 100 are envisioned that are suitable for treating multiple sizes of hearts. For example, the diameters of some or all of portions 114, 116, and 118 can be available in incremental sizes. In some embodiments, the axial lengths of some or all of portions 114, 116, and 118 are also configured in incremental sizes. As will be described further herein, an implant 100 of a particular size can be selected for a patient based on a pre-operative measurement of the patient's heart. For example, in some instances a measurement is taken of the patient's largest ventricular perimeter, and that measurement is used to select the size of implant 100 to be used for that patient. As will be described further herein, various sizes of implants 100, each of which is preloaded on an implant delivery device (refer to FIGS. 5-7), can be available to a clinician, and the clinician can select a particular size of implant 100 based on the measurement of the patient's heart. In some embodiments, a particular size of implant 100 can be used for a range of heart measurement values. For example, a particular size of implant 100 may be used for a range of maximum ventricular perimeters of 36.9 cm to 40.0 cm. Another size of implant 100 may be used for a range of maximum ventricular perimeters of 40.1 cm to 43.4 cm. Still another size of implant 100 may be used for a range of maximum ventricular perimeters of 34.0 cm to 36.8 cm, and so on. It should be understood that these ranges of maximum ventricular perimeters provided are merely illustrative, and are non-limiting examples. In addition, the combination of mesh material compliance and size, hem construction including the compliance of an elastic band on the hem 113, and fillable bladder construction include the compliance of materials used to construct together may be selected in accordance with the teachings herein to achieve implant design configurations that enable a fewer number of sizes for a wide range of heart sizes, thereby achieving inventory cost benefits. In some embodiments, the trailing end portion 118 is configured to have the same diameter across all sizes of implants. The fillable bladder 120 may also be implemented with various sizes. For example, larger fillable bladders may be used with larger sized implants, and smaller fillable bladders may be used with smaller sized implants.

Still referring to FIGS. 2A-2C, the leading end 112 in this embodiment is defined by the hem 113. In some embodiments, the hem 113 can be constructed by wrapping some of the mesh material at the distal end of the leading portion 114 around the elastic band, and then securing the free end of the material to an interior portion of the leading end portion 114. Such securing may be continuous or in multiple discreet sections. In particular embodiments an elastic hem band material can be contained within the doubled over layers of mesh material. The elastic hem band material can be made of a low durometer silicon elastomer material, or any other suitable elastic biocompatible material. The diameter of the elastic hem band material, at rest, may be less than the at rest diameter of the mesh material at the hem 113. By way of example, in some embodiments the circumference of the mesh material, at rest, in the hem 113 may be about 25 centimeters, whereas the length of the elastic hem band material may be about 20 centimeters. Such a configuration may accommodate, by way of example only, a heart size wherein the atrial-ventricular groove may be about 30 centimeters in circumference. Owing to the length of the elastic band being longer than the circumference of the mesh material at the hem 113, the mesh material at the hem 113 may be gathered in a slightly wavy or "bunched" configuration about the internal elastic member when the hem 113 is not being stretched around the heart H. In some alternative embodiments, the internal elastic band may not be implemented, and in such cases, the mesh material may be configured into a reduced diameter region in the hem area so as to enable an interference fit of the hem area into an atrial-ventricular groove. In other alternative embodiments, the elastic band serves as the hem 113 and distal end 112 with the mesh material wrapping around it, and in such cases, the mesh material may be bonded to a proximal periphery of the elastic band. Optionally, the trailing end 119 may also be hemmed, and the hem of the trailing end 119 may or may not include an elastic member.

As previously described, some embodiments of the implant 100 include multiple radiopaque markers 115 located around the hem 113 and multiple radiopaque markers 125 located around the periphery of the fillable bladder 120. As described previously, various types of radiopaque markers can be used. In some embodiments, the radiopaque markers 115 and 125 have an adhesive quality during manufacture of the implant 100 that can be used advantageously during the construction of the implant 100. For example, the second group of radiopaque markers 125 can be adhered to the mesh body 110 and, via the interstitial spaces of the mesh, adhered to the fillable bladder 120 to thereby affix the fillable bladder 120 to the implant 100. In one such embodiment, the radiopaque markers 125 (and 115) can be made from raw materials such as a silicone adhesive paste mixed with powdered tantalum. During manufacturing of the implant 100, the mixture can be injected into depressions residing in a metal plate, and that are configured in a generally rectangular pattern as defined by the radiopaque markers 125 shown in the implant 100. The metal plate can thereby act as a mold for forming the radiopaque markers 125. The mesh body 110 can be placed over the metal plate in an orientation that will position the fillable bladder 120 as desired in relation to the mesh body 110. The fillable bladder 120 can be placed on top of the mesh body 110 in an orientation so as to locate the radiopaque markers 125 around the periphery of the fillable bladder 120. A second metal plate can be positioned over the fillable bladder 120. The second metal plate may have a depression that corresponds to the fillable bladder 120. The stacked assembly can then be heated to cure the silicone adhesive paste. In the process, the radiopaque markers 125 become adhered to the mesh body 110 and to the fillable bladder 120. In this manner, the radiopaque markers 125 can be used to affix the fillable bladder 120 to the mesh body 110. Using a similar technique, the radiopaque markers 115 can be formed and adhered to the exterior layer of the mesh material of the hem 113, and adhered to the internal elastic band of the hem 113. Furthermore, the elastic band can thereby be "staked" in relation to mesh material of the hem 113 at the locations of the radiopaque markers 115. In other embodiments, the fillable bladder 120 and/or elastic band of the hem 113 can be affixed to the mesh body 110 using other bonding techniques, such as adhesives, mechanical clips, sutures, interweaving, ultrasonic welding, RF welding, and the like.

Still referring to FIGS. 2A-2C, the implant 100 includes the fillable bladder 120, which as previously described, can be used to exert a localized pressure on a surface of the heart to induce a therapeutic deflection thereto. FIG. 2B illustrates the fillable bladder 120 in a deflated state, and FIG. 2C illustrates the fillable bladder 120 in an inflated state. While the fillable bladder 120 depicted in FIGS. 2A-2C is generally rectangular in shape, other shapes of fillable bladders are also envisioned. For example, fillable bladders can be circular, elliptical, semi-toroidal, triangular, linear, pyramidal, irregularly shaped, and any other like shape, or combinations of shapes.

As previously described, the inflation tube 130 is in fluid communication the fillable bladder 120. The inflation tube 130 is of a flexible tubular construction and is configured to remain in the patient's body as part of the implant 100, and to remain in fluid communication with the fillable bladder 120. The free end of the inflation tube 130 can be positioned subcutaneously, and near to the underside of the epidermis. In some implementations, the free end of the inflation tube 130 is located in an intercostal space after implantation of the mesh body 110 around the heart. So locating the free end of the inflation tube 130 may allow future access to the inflation tube 130 via a simple cut-down procedure through the skin adjacent to the intercostal space between the ribs (e.g., the fifth intercostal space in some implementations). Future inflation or deflation of the fillable bladder 120 may thereby be performed with a minimally invasive access to an intercostal space under the side without extensive surgery to access the pericardium or epicardium.

In some embodiments, the flexible inflation tube 130 is made of silicone, but other biocompatible materials may also be used. In some embodiments, the outer diameter of the inflation tube 130 can range from about 0.065 inches to about 0.25 inches (about 1.60 mm to about 6.40 mm). In one example embodiment, the outer diameter of the inflation tube is about 0.125 inches (about 3.2 mm). In some embodiments, the inner diameter of the inflation tube 130 can range from about 0.031 inches to about 0.125 inches (about 0.78 mm to about 3.18 mm). In one example embodiment wherein the outer diameter of the inflation tube is about 0.125 inches (about 3.2 mm), the inner diameter of the inflation tube is about 0.0625 inches (about 1.58 mm). Such inflation tube dimensions are provided as examples, and it should be understood that other sizes are also envisioned within the scope of this disclosure. In addition, the cross-sectional sizing of the inflation tube may be selected to accommodate the specific inflation material (and in some cases radiopaque contrast agent) that will flow through the tube (discussed below).

The inflation tube 130 provides a flexible conduit through which inflation fluid can be conveyed to inflate or deflate the fillable bladder 120. After inflating or deflating the fillable bladder 120 with a selected volume of inflation fluid, the proximal end region of the inflation tube 130 is sealed to prevent withdrawal of the inflation fluid from the fillable bladder 120. Various types of inflation fluids can be used. For example, the inflation fluid can be a saline liquid solution, silicone gel, gaseous substances, and fluids containing a contrast agent that facilitate visualization of the inflation fluid via imaging systems.

In some embodiments, the fillable bladder 120 is configured of two different sheet components 122 and 124 so that the bladder 120, when inflated, expands more interiorly (that is, toward the heart wall when implanted) than exteriorly. As such, the bladder 120 is configured to provide a differential compliance in which one surface of a bladder 120 is significantly more compliant than the opposing (less compliant) surface of the bladder 120. In the context of fillable bladder 120, the interior sheet component 122 of the fillable bladder 120 is more compliant than the outer sheet component 124 of the fillable bladder 120. When the implant 100 is installed on a heart, the heart is located within the interior region of the mesh body 110 and in contact with the interior sheet component 122 of the fillable bladder 120. The greater compliance of the interior sheet component 122 of the fillable bladder 120 (in relation to the lesser compliance of the outer surface material) can accentuate the localized pressure applied onto the surface of the heart when the fillable bladder 120 is inflated.

Figure 3:
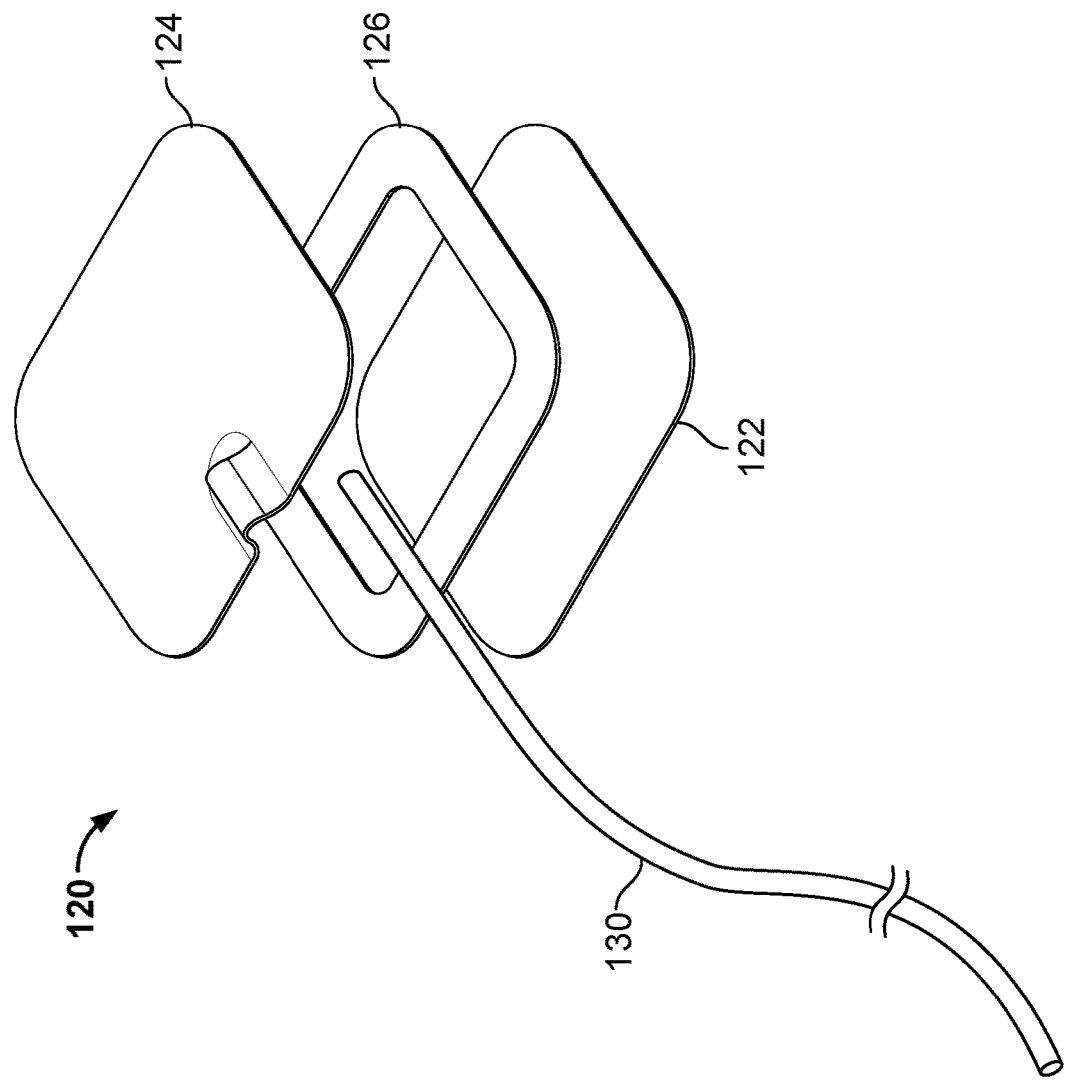
FIG. 3 is an exploded view of a fillable bladder, in accordance with some embodiments.

Referring now to FIG. 3, some embodiments of the fillable bladder 120 can include the two different sheet components 122 and 124 in the form of an interior sheet component 122 and an outer sheet component 124. A chamber for containing fluids can be formed therebetween by hermetically sealing together the periphery of the sheet components 122 and 124. As discussed above, this sealed periphery of the bladder 120 is the portion of the bladder 120 to which the radiopaque markers 115 are attached through spaces in the mesh material interposed between the bladder 120 and the markers 115. In this embodiment of the bladder 120 shown in FIG. 3, the sheet components 122 and 124 are sealed together using a bonding agent 126, but other techniques are also envisioned, such as ultrasonic welding, solvent bonding, a molded monolithic bladder, and the like. An end portion of the inflation tube 130 is also sealed between the sheet components 122 and 124, such that the lumen of the inflation tube 130 is in fluid communication with the resulting chamber of the fillable bladder 120. In some embodiments, a fitting may be used to couple an inflation tube to a fillable bladder.

The material of the interior sheet component 122 can be selected to have a higher compliance than the material selected for the outer sheet component 124. The interior sheet component 122 can be made of a silicone sheet material, or other biocompatible airtight sheet materials. In some embodiments, the thickness of the interior sheet component 122 is in the range of about 0.005 inches to about 0.050 inches (about 0.12 mm to about 1.30 mm). In one example embodiment, the interior sheet component 122 is a silicone sheet material that is about 0.015 inches (about 0.38 mm) in thickness. The outer sheet component 124 can also be made of a silicone sheet material, or other biocompatible airtight sheet materials. In some embodiments, the material of the outer sheet component 124 can be reinforced (e.g., with a polyester mesh that is impregnated into the sheet) to resist deformation, thereby reducing the compliance of the outer sheet component 124. In some embodiments, the thickness of the outer sheet component 124 is in the range of about 0.005 inches to about 0.070 inches (about 0.12 mm to about 1.78 mm). In one example embodiment wherein the interior sheet component 122 is a silicone sheet material that is about 0.015 inches (about 0.38 mm) in thickness, the outer sheet component 124 is a reinforced silicone sheet material that is about 0.020 inches (about 0.51 mm) in thickness.

Various sizes of inflatable bladders 120 can be constructed, and differently sized inflatable bladders 120 can be used with differently sized implants. In some embodiments, the length and width dimensions of the sheet components 122 and 124 (including the peripheral regions of the membranes that are sealed together) can be in a range from about 0.5 inches to about 4.0 inches (about 12.7 mm to about 101.6 mm). In one example embodiment, the length and width dimensions of the membranes 122 and 124 are in a range from about 1.075 inches to about 2.265 inches (about 27.30 mm to about 57.53 mm). In some embodiments, the fillable bladder 120 has a peripheral seal that is about 0.25 inches (about 6.35 mm) wide, and the sheet material within the peripheral seal is the inflatable portion.

In this embodiment, the peripheral bonding of the sheet components 122 and 124 can be accomplished using the bonding agent 126. The bonding agent 126 can cross-link with the materials of the sheet components 122 and 124 when the bonding agent 126 and sheet components 122 and 124 are heat-soaked as an assembly. In one example, the assembly is heat-soaked at about 350 F (about 177 C) for about 2 hours. Other heat-soaking time and temperature combinations can also be used, and lower temperatures will tend to require longer durations (and vice versa). Various types of bonding agents 126 can be used. In a preferred embodiment, the bonding agent 126 is a non-vulcanized silicone sheet that is about 0.010 inches (about 0.25 mm) thick. After the bonding of the inner and outer sheet components 122 and 124, and the inflation tube 130, the fillable bladder 120 can be leak tested to confirm that the fillable bladder 120 is hermetically sealed.

Upon implantation and proper positioning of the fillable bladder 120 with respect to targeted heart H structure(s), the fillable bladder 120 (and specifically the bladder's interior sheet component 122) is located and bears against an outer epicardial wall of the heart H, and the mesh material of the mesh body 110 that is located exteriorly of the bladder 120 faces outwardly and bears against the pericardium. When the bladder 120 is inflated, the interior sheet component 122 of the bladder 120 expands inwardly (e.g., expansion from a reference plane defined as extending through the sealed periphery region of the bladder 120) more so than the outer sheet component 124 of the bladder 120 expands outwardly from this reference plane. This characteristic is accentuated in larger bladder embodiments in comparison to smaller bladder embodiments. Therefore, design selections, including interior and outer sheet properties as well as bladder size and other parameters, can be made to attain a fillable bladder with the desired expansion characteristics.

The combination of the implant's mesh body 110 located exteriorly of the bladder 120 (which provides an circumferential restraint force to urge the bladder 120 toward the heart H) and the presence of the pericardium that surrounds the heart H (the pericardium providing a bearing surface against which the implant's mesh material and hence the outer sheet component 124 of the bladder 120 bears) collectively resist outward movement of the bladder 120. This resistance to outward movement of the bladder 120 from the heart H also contributes so that the interior sheet component 122 of the bladder provides localized pressure upon the targeted surface region of the heart. This localized pressure deforms not only the targeted surface region of the heart wall, but also valve structures located inside the chambers of the heart in the location of the localized pressure (refer to FIG. 1B). In addition, at some point in time after implantation (typically in about 1 week to 3 weeks), the mesh body 110 makes a fibrous attachment to both the epicardial wall and to the pericardium. This fibrous attachment of the mesh body 110 to both the epicardial wall and the inner wall of the pericardium increases the resistance to outward movement of the bladder 120, thereby increasing the degree to which the inward expansion of the interior sheet component 122 of the bladder 120 provides localized pressure upon the targeted surface region of the epicardial wall that lies adjacent the bladder 120.

Figure 4A:
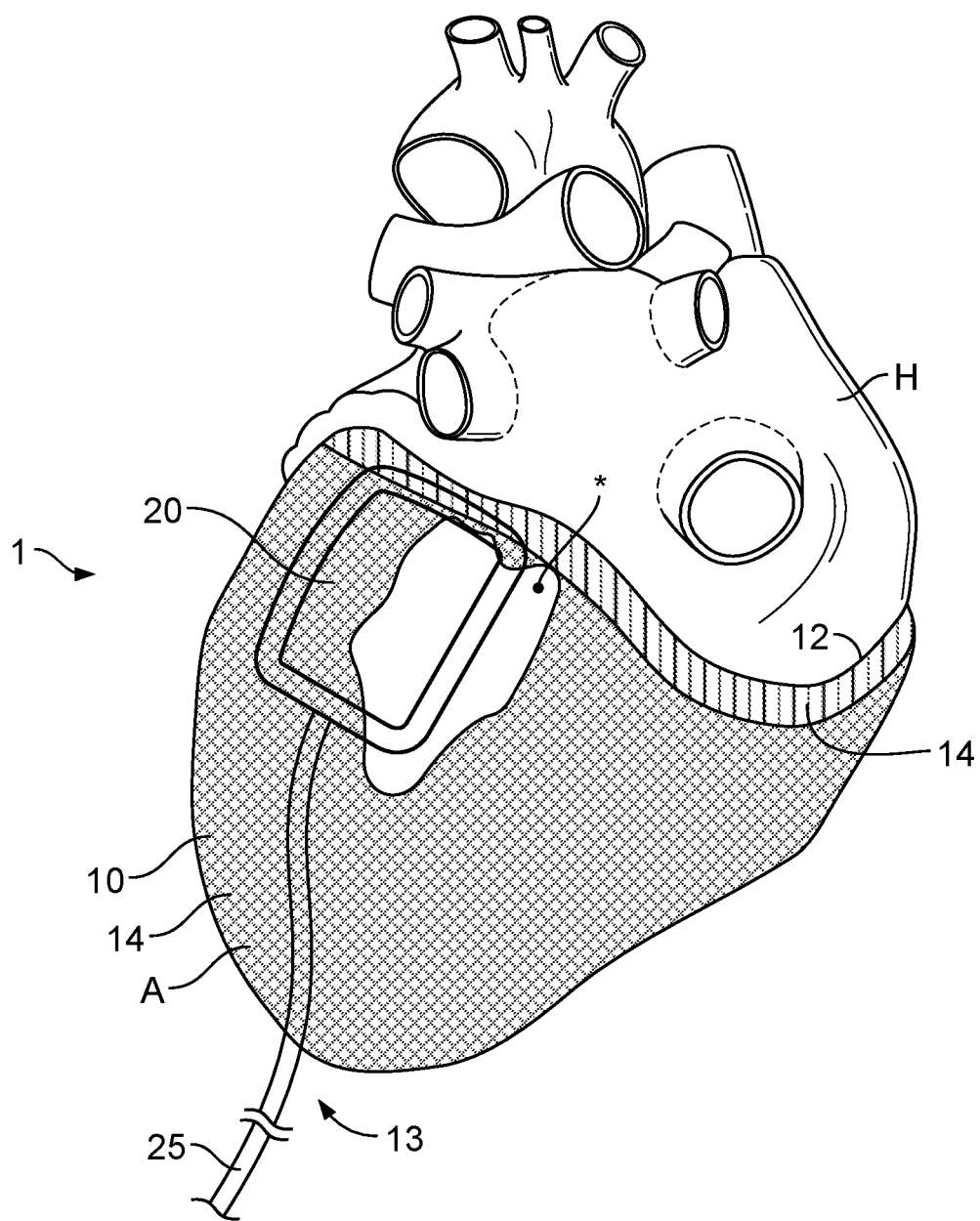
FIG. 4A is a perspective view of another implant for treating a heart that is positioned on a patient's heart, in accordance with some embodiments.
Figure 4B:
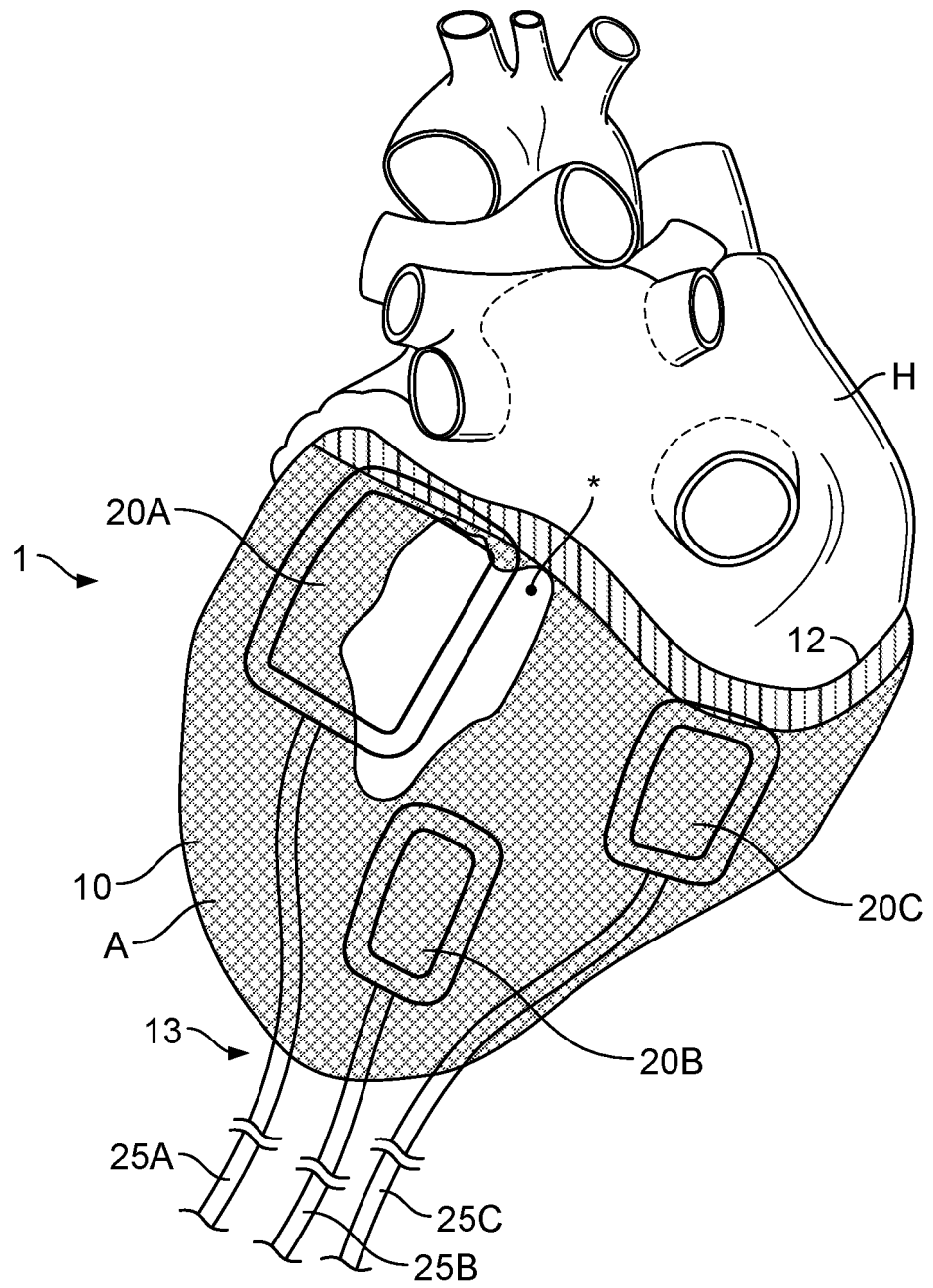
FIG. 4B is a perspective view of another implant for treating a heart including three optional bladder locations at the mitral valve, papillary muscle and tricuspid valve, in accordance with some embodiments.

FIGS. 4A and 4B show alternative embodiments having one or more inflatable bladders, as follows. In FIG. 4A, the inflatable bladder is positioned adjacent to the patient's mitral valve. FIG. 4B shows additional placement locations of bladders adjacent to the papillary muscle and tricuspid valve. It is to be understood that the description herein encompasses embodiments with only one or with more than one inflatable bladder. Thus, FIGS. 4A and 4B simply show preferred locations for the bladder placement(s).

Figure 5:
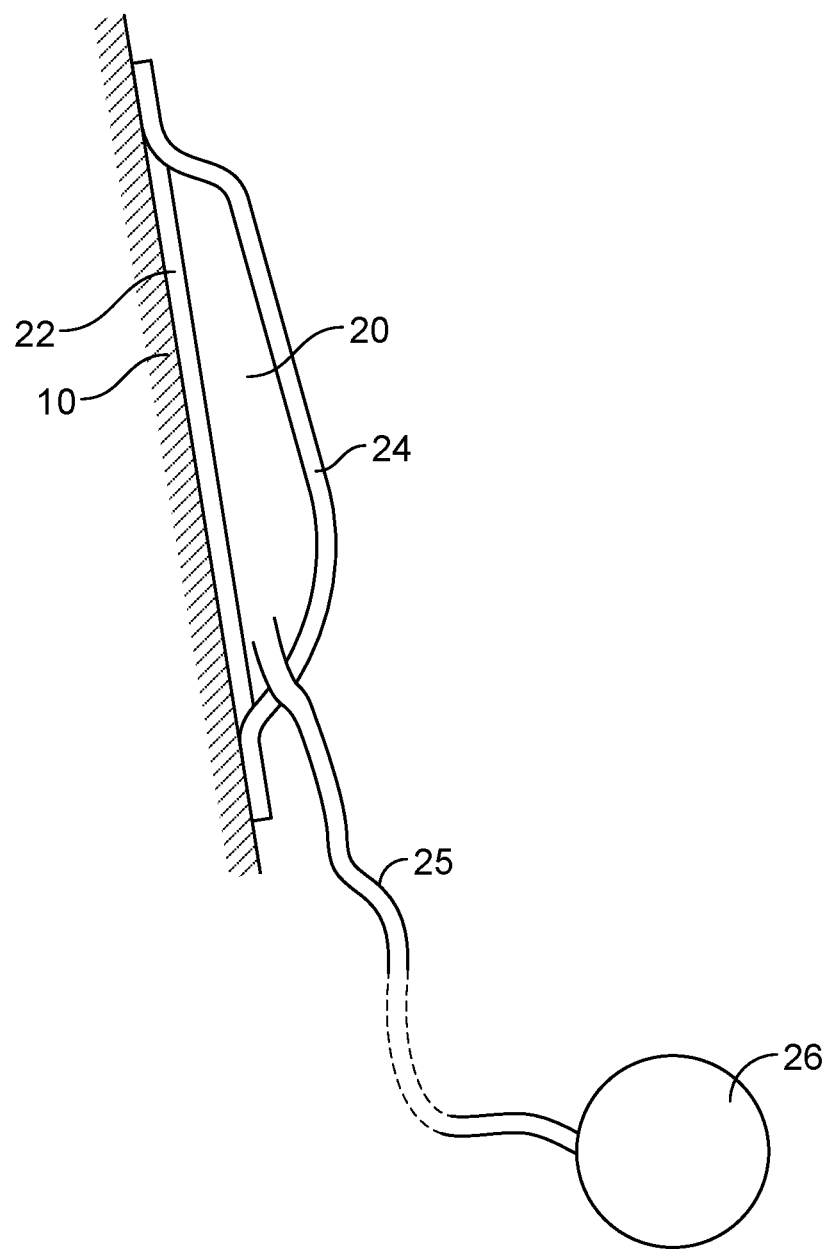
FIG. 5 is a sectional elevation view through one of the inflatable bladders of FIGS. 4A and 4B.

As seen in FIGS. 4A-B and 5, the depicted embodiment provides an assembly making up an implant 1 wherein the assembly comprises: a jacket 10 and at least one inflatable bladder 20. Jacket 10 is made of a flexible biocompatible material and has an open top end 12 that is received around the heart H and a bottom portion 14 that is received around the apex A of the heart. In optional aspects, jacket 10 may be made of a knit mesh. This knit mesh may optionally be made of a polymer, including but not limited to high-density polyethylene. Alternatively, jacket 10 may be made of metal.

In one example embodiment, jacket 10 is made of a suitable knit material. An example of such a knit material may be "Atlas Knit" material described above. Alternatively, jacket 10 may be elastic. Optionally, the fibers may be made of Denier polyester. However, other suitable materials, including but not limited to, PTFE, ePTFE, polypropylene and stainless steel may also be used. Advantages of using a knit material include flexibility, fluid permeability and minimizing the amount of heart surface area in direct contact with the jacket (thereby minimizing the potential of scar tissue development).

Inflatable bladder 20 is disposed on an interior surface of jacket 10. Bladder 20 may or may not be attached to jacket 10. FIG. 4B illustrates three separate inflatable bladders 20, one being located near a hem of the implant 1 and being positioned on a posterior portion of the heart H wall adjacent the mitral valve (bladder 20A), one being located away from the hem for positioning to a portion of the heart H wall adjacent to a papillary muscle (bladder 20B), and one being located also near a hem of the implant 1 and positioned on an anterior portion of the heart H wall adjacent the tricuspid valve (bladder 20C). In embodiments wherein the bladder 20 is attached to the jacket 10 prior to implantation of the implant 1, the implant may include one, two or all of the three bladders 20A-C depicted in FIG. 4B. As such, FIG. 4B depicts the different locations where a bladder 20 may be located, wherein some embodiments may include only one or two bladders 20 positioned on the jacket 10 so that the bladder 20 may be positioned at the depicted locations shown in FIG. 4B. When bladder 20 (that is, bladder 20A in FIG. 4B) is positioned adjacent to the mitral valve, it is preferably positioned at the P2 area of the valve (in the center of the posterior leaflet) to reduce the distance across the valve, thereby reducing the gap in the valve responsible for the regurgitation. When bladder 20C is positioned adjacent to the tricuspid valve, it performs a similar function, reducing regurgitation through the tricuspid valve. When bladder 20B is positioned adjacent to the papillary muscle, it gently corrects papillary muscle position and relieves tension on the chordae (which otherwise prohibits normal valve functioning).

As seen in FIG. 5, inflatable bladder 20 has an inelastic outer surface 22 positioned adjacent to jacket 10 and an elastic inner surface 24 positioned adjacent to the heart H, as discussed previously in connection with other embodiments. Bladder 20 may optionally be made of silicon. In some embodiments, jacket 10 is relatively non-compliant in comparison to the elastic inner surface 24, the outer surface 22 of bladder 20 positioned adjacent to the bladder is also relatively non-complaint, and the inner surface 24 of bladder 20 is elastic. As a result and as described above, when inflated through fluid supply line 25, inflation of bladder 20 causes the bladder to deform substantially inwardly (i.e., towards the heart). This then exerts localized pressure against a region of the heart. As can be seen, supply line(s) 25 are positioned inside jacket 10 and extend out of an open bottom end 13 of the jacket adjacent to the apex of the heart. Bottom end 13 may be cinched (and/or sewn) closed after the jacket 10 has been positioned around the heart.

As discussed previously, bladder 20 may be inflated with fluids including air, inert gasses (such as fluorocarbons), silicone gel, saline and contrast agents. Supply lines 25 may optionally be inflated through a blunt needle port, a Luer port fitting, a subcutaneous port 26, etc. In other embodiments, a port-type device may not be used, and instead, the supply lines may be clamped in a closed position, as described previously. Supply lines 25 are made of a suitable bio-compatible material, including but not limited to silicone. This document includes a disclosure of various mechanisms for inflating and deflating bladders 20 post-implementation. For example, in one approach the device is first received onto the heart. After a period of time (e.g.: 30 days) fibrotic encapsulation of mesh jacket 10 will have occurred. At this time, the bladder(s) 20 can then be inflated (through supply line 25 using a needle to percutaneously access filling reservoir 26). Thus, subcutaneous ports 26 may be employed for percutaneous inflation and deflation for therapy optimization or abandonment. Alternatively, and because in some cases implanted subcutaneous port-type devices may have potential drawbacks, clamping of the fluid path tube may be done, with the fluid path staying in the intercostal space and may be accessed by a small "cut-down" procedure to access the tube.

In optional embodiments, jacket 10 has an elastic band 14 passing around its top end 12, as described previously. In addition, radiopaque markers 15 can also be provided around top end 12 of the implant 1.

The present jacket and bladder implant system 1 can be placed around the patient's heart in a variety of different approaches. In an example method of use, the present system further includes a delivery device for positioning the jacket onto the heart, as described later in this document. In one example of the method described later in this document, the assembly is implanted into the patient in a left intercostal mini-thoracotomy using contrast pericardiography and fluoroscopic visualization. After opening the parietal pericardium, the lower portion of the heart is free for applying the jacket over the apex.

In some embodiments, methods of providing localized pressure to a region of a patient's heart H to improve heart functioning may be performed by: (a) positioning an assembly around a patient's heart, wherein the assembly comprises a jacket 10 and at least one inflatable bladder 20, wherein jacket 10 is made of a flexible biocompatible material having an open top end 12 that is received around the heart and a bottom portion 14 that is received around the apex of the heart, and the inflatable bladder 20 is disposed on an interior surface of the jacket, and the inflatable bladder 20 has an inelastic outer surface positioned adjacent to the jacket and an elastic inner surface. In addition, bladder 20 may be inflated causing it to expand such that the bladder deforms substantially inwardly to exert localized pressure against a region of the heart.

In another method of use, a pericardial edge management system (PEMS) may be used in the surgical procedure for safe introduction of the implant 1. A PEMS includes multiple separate sheets that each have one "peel and stick" side, and may be made of Teflon. These sheets can be used to keep the opening into the pericardium open to facilitate insertion of the device without damage to the pericardium (i.e., the insertion tool getting hung up on the edges of the opening). In addition, the PEMS can be used to initially separate the heart from the mesh fabric. After all of the PEMS sheets are pulled out, the jacket fabric can then engage the heart.

Figure 6A:
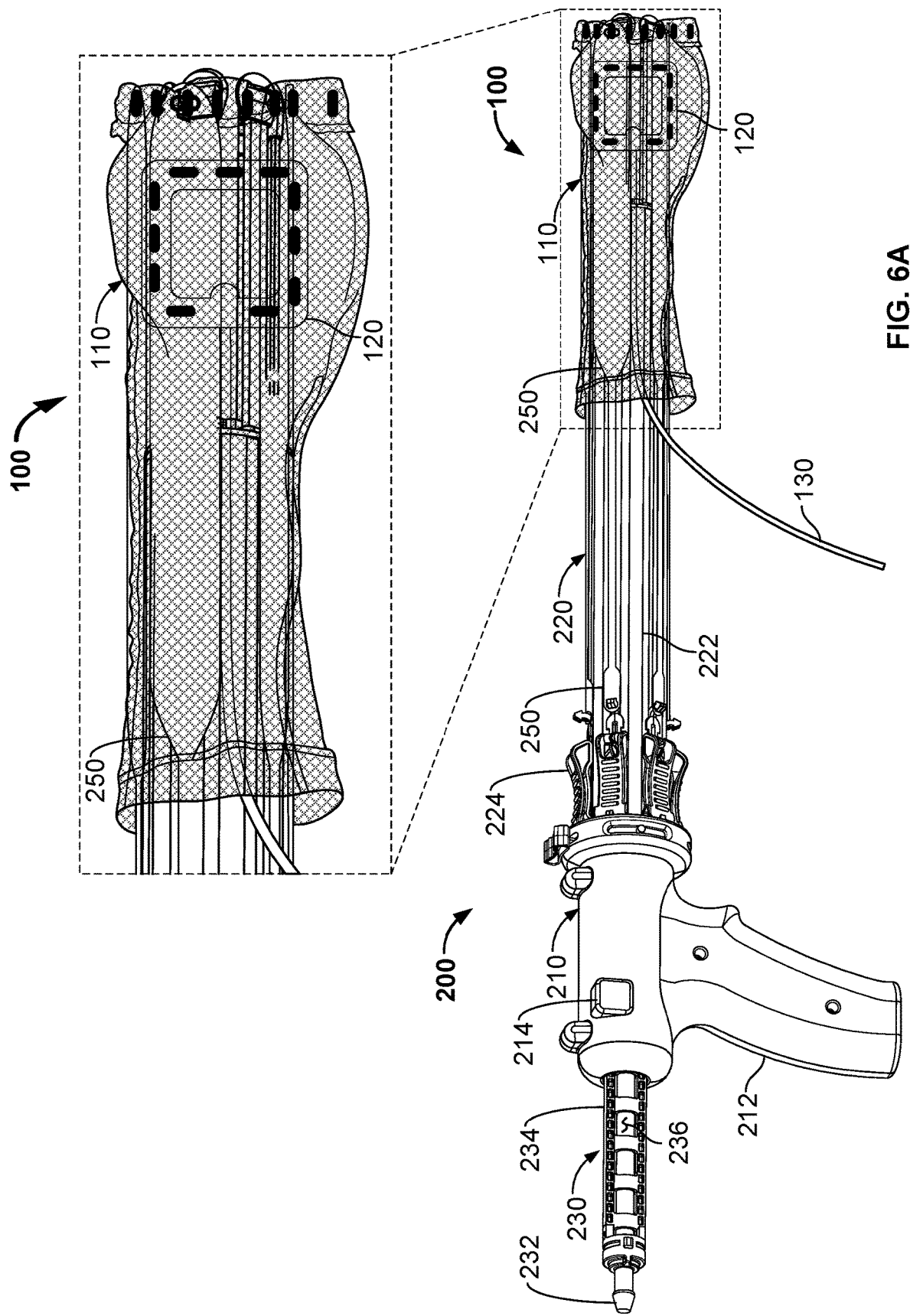
FIG. 6A is a perspective side view of an implant delivery device that is loaded with an implant, in accordance with some embodiments.
Figure 6B:
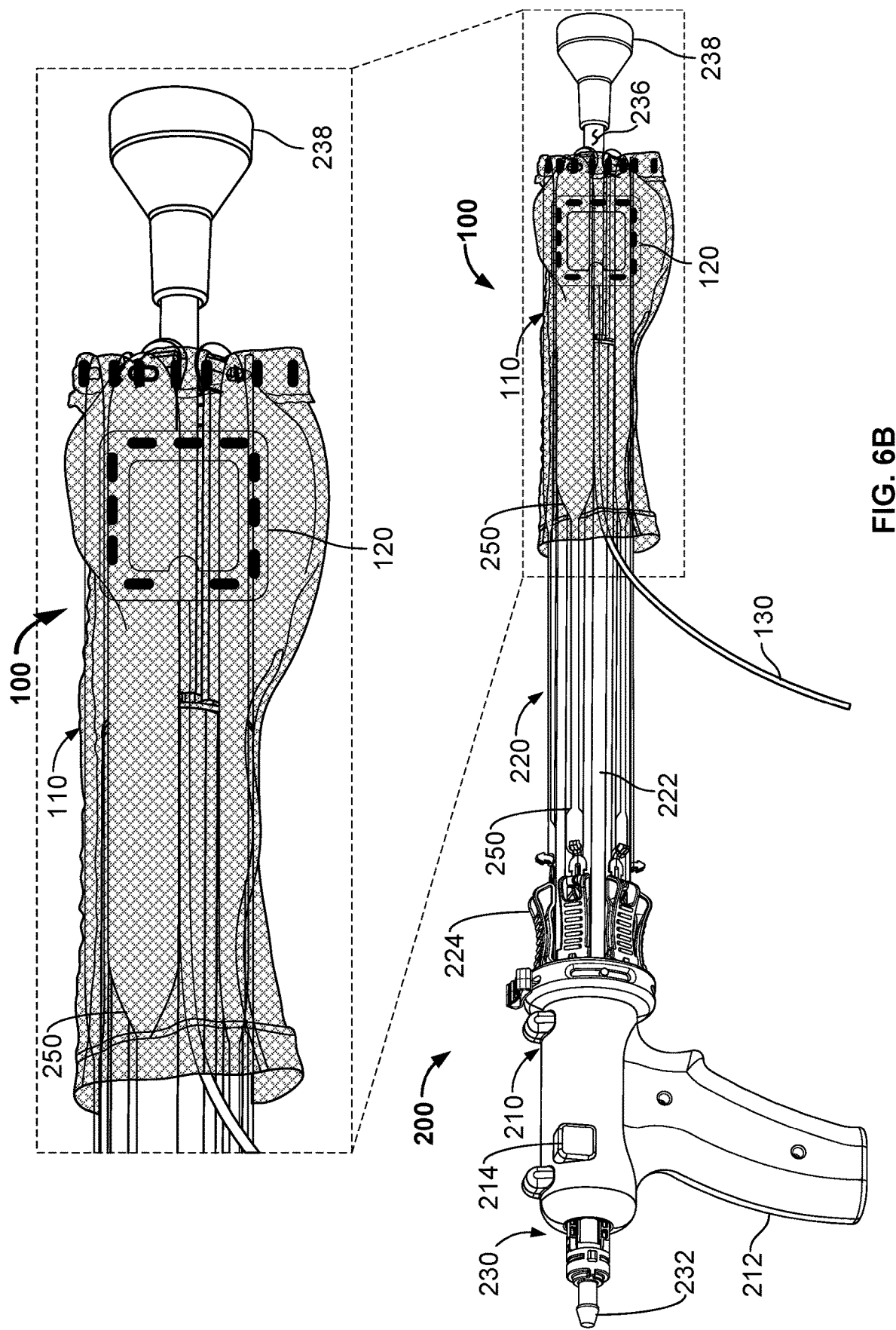
FIG. 6B is a perspective side view of the implant delivery device of FIG. 6A with a heart stabilizer in an extended position.
Figure 6C:
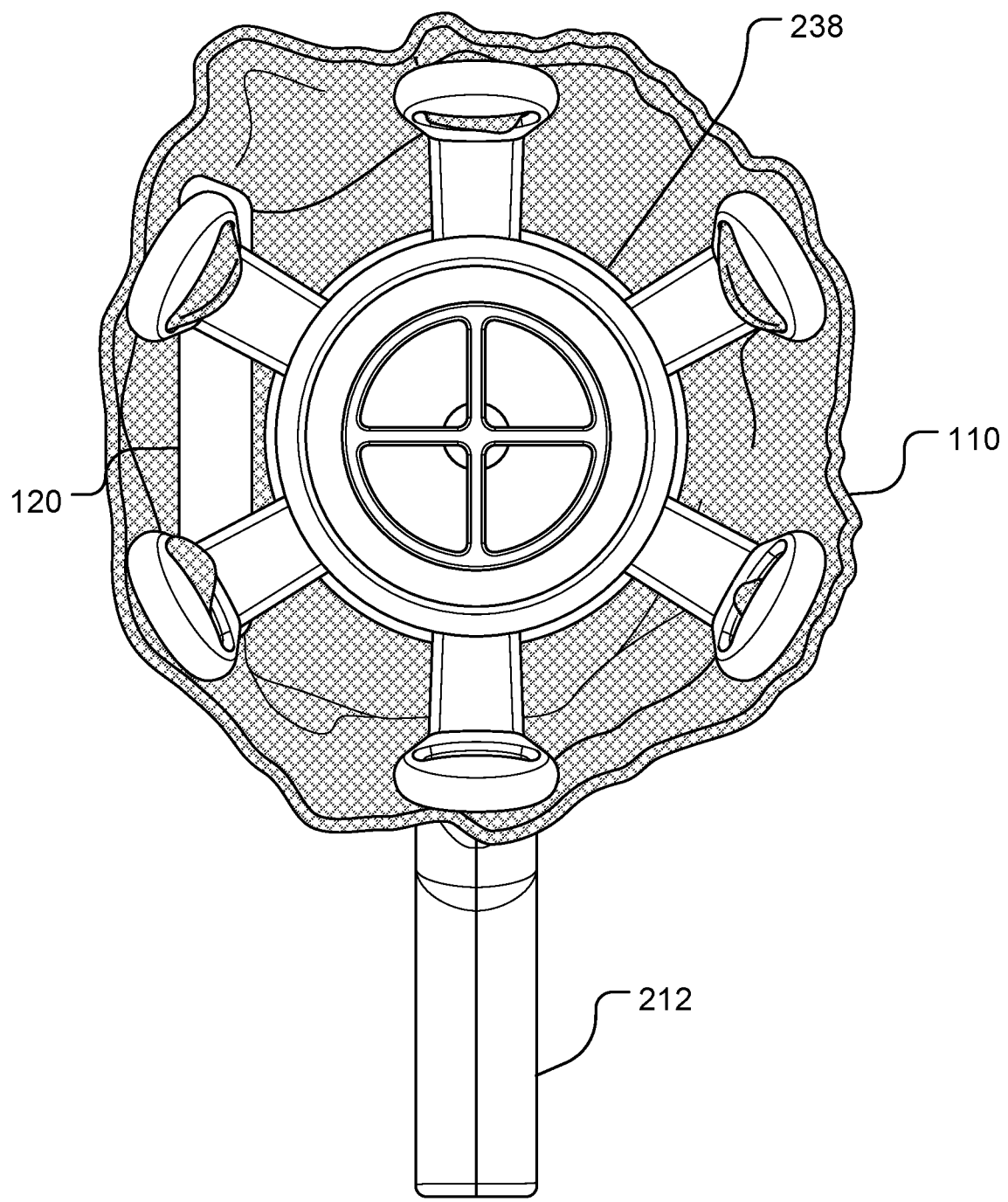
FIG. 6C is a distal end view of the implant delivery device of FIG. 6A.

Referring to FIGS. 6A-6C, some embodiments of a delivery device 200 can be used by a clinician to install the implant 100 onto a patient's heart. As described in detail below, during a procedure to install the implant 100, some distal portions of the delivery device 100 are temporarily advanced within the body of the patient, while other proximal portions of the delivery device 100 remain external to the patient's body. The delivery device 200 used for installing the implant 100 is a sterile device. In some embodiments, the delivery device 200 is a sterile single-use device. Alternatively, the delivery devices may be designed to be re-sterilized and reused.

In this embodiment, the implant 100 is loaded onto the delivery device 200 at a distal end of the delivery device 200. A main body 210 of the delivery device 200 is located near a proximal end of the delivery device 200. A barrel assembly 220 extends from the main body 210 to the distal end of the delivery device 200. The implant 100 surrounds and is coupled to a distal end of the barrel assembly 220. A proximal end of the barrel assembly 220 is attached to the main body 210. A heart stabilizer assembly 230, which may be configured to releasably anchor to the apex of the hearth H during an implantation procedure, extends from a proximal end of the main body 210 to the distal end of the barrel assembly 220.

In some embodiments, the delivery device 200 and the implant 100 are pre-assembled and packaged together in sterile packaging. That is, the delivery device 200 can be provided to a clinician with the implant 100 pre-loaded onto the delivery device 200 and ready for sterile use. As described elsewhere herein, implants 100 of various sizes are used in order to properly fit multiple sizes of hearts. Therefore, a hospital that performs procedures to install the implants 100 may keep an inventory of various sized implants 100, each of which is pre-loaded on a particular delivery device 200 and packaged in sterile packaging. After the clinician determines the size of patient's heart, the clinician can select from the hospital's inventory the implant 100 that is sized to best fit the patient's heart. The clinician will receive a sterile delivery device 200 that is pre-loaded with that selected size of implant 100. After the implant 100 is deployed from the delivery device 200, the delivery device 200 may be discarded as a single-use instrument (for those embodiments in which the delivery device 200 is packaged as a single-use device).

Still referring to FIGS. 6A-6C, the main body 210 of the delivery device 200 may optionally include a pistol grip type handle 212 for handling by a clinician and also may include a lock release button 214 for the heart stabilizer 230. The pistol grip handle 212 provides a convenient and ergonomic structure by which a clinician can grasp and maneuver the delivery device 200. In some embodiments, the pistol grip handle 212 includes a textured surface to enhance the friction between the pistol grip handle 212 and the clinician's hand. The lock release button 214 in this embodiment is a spring-loaded depressible button that is biased to extend outward from the main body 210. When the lock release button 214 is depressed inward in relation to the main body 210, the heart stabilizer assembly 230 is unlocked and therefore able to translate axially relative to the pistol grip type handle 212. When the lock release button 214 is not depressed, the lock release button 214 extends outward from the main body 210 and the heart stabilizer assembly 230 is locked in its axial position and therefore not able to translate axially.

The barrel assembly 220 of the delivery device 200 may optionally include a splined elongate barrel 222 for guiding the actuators 224 of the delivery device 200. In this embodiment, six actuators 224 are included around the periphery of the barrel 222. In other embodiments, fewer or more than six actuators can be included in a delivery device. The actuators 224 are each individually slidably coupled to a spline of the barrel 222. The actuators 224 are also each individually releasably coupled to an epicardial management strip 250. In this embodiment, there are a total of six epicardial management strips 250. The epicardial management strips 250 extend from the actuators 224, on the external surface of the barrel 222, under the implant 100, and terminate where the implant 100 is coupled to the delivery device 200. The epicardial management strips 250 provide low-friction surface area that facilitates the advancement of the implant 100 onto a heart. The epicardial management strips 250 are not shown in FIG. 6C so that other components of the implant 100 and delivery device 200 are visible.

Still referring to FIGS. 6A-6C, the heart stabilizer assembly 230 can include a vacuum connection fitting 232, a shaft rack 234, a vacuum tube 236, and a distal vacuum cup 238. Those components of the heart stabilizer assembly 230 are affixed together in the configuration as shown. That is, when the heart stabilizer assembly 230 is moved in relation to the other parts of the delivery device 200 (while the lock release button 214 is depressed), the vacuum connection fitting 232, heart stabilizer shaft rack 234, vacuum tube 236, and vacuum cup 238 move as a unit together in the axial direction.

In this embodiment, the vacuum connection fitting 232 is a barbed fitting. Other types of fittings can also be used, such as luer connections, compressing fittings, threaded fittings, quick-lock fittings, and the like. A source of negative pressure (vacuum) can be connected via flexible tubing (not shown) to the vacuum connection fitting 232. The negative pressure will be communicated from the vacuum connection fitting 232, through the vacuum tube 236, and to the vacuum cup 238.

The shaft rack 234 of the heart stabilizer assembly 230 is configured to be releasably engageable with the lock release button 214. Engagement between the shaft rack 234 and the lock release button 214 effectuates the locking of the heart stabilizer assembly 230 in a selected axial position in relation to the main body 210 and barrel assembly 220. Disengagement of the shaft rack 234 and the lock release button 214 (when the lock release button 214 is depressed) unlocks the heart stabilizer assembly 230 such that the heart stabilizer assembly 230 can move axially in relation to the main body 210 and barrel assembly 220.

In this embodiment, the shaft rack 234 includes a series of holes with which one or more protrusions on the shaft lock release button 214 engage. When the lock release button 214 is extending outward from the main body 214 (which is the default position of the button 214), the one or more protrusions on the lock release button 214 extend into one or more holes on the shaft rack 234 to lock the heart stabilizer assembly 230 in place. In contrast, when the lock release button 214 is depressed towards the main body 214 (e.g., by manually pushing the button 214), the one or more protrusions on the lock release button 214 become disengaged from the holes on the shaft rack 234. As a result of depressing and maintaining the lock release button 214 in a depressed position, the heart stabilizer assembly 230 becomes unlocked and free to move axially in relation to the other parts of the delivery device 200. That is the case because depressing and maintaining the lock release button 214 in a depressed position disengages the protrusions of the lock release button 214 from the holes of the shaft rack 234. When the lock release button 214 is no longer maintained in the depressed position, the outward bias of the lock release button 214 causes the button 214 to translate to an extended position to once again lock the heart stabilizer assembly 230 in relation to the other parts of the delivery device 200.

In one example, a comparison of FIGS. 6A and 6B illustrates how the heart stabilizer assembly 230 can translate axially when the lock release button 214 is pressed. For example, in FIG. 6A the heart stabilizer assembly 230 is in an axially retracted position (a proximal position). To extend the heart stabilizer assembly 230 distally (e.g., to the position shown in FIG. 6B), first the lock release button 214 is manually pressed and maintained in a depressed position, and then the heart stabilizer assembly 230 can be manually slid distally in the axial direction. In the configuration of FIG. 6B, and as will be described further below, the vacuum cup 238 extends distal-most and is positioned to be the initial member of the delivery device 200 to be inserted into the chest cavity of a patient during an implant 100 installation procedure.

Various other design embodiments for locking and unlocking the heart stabilizers are also envisioned. Such embodiments can include the use of, but are not limited to, eccentric collars, cam mechanisms, interlocking tapers, over-center devices, set screws, and the like.

Still referring to FIGS. 6A-6C, the location of the fillable bladder 120 on the implant 100, and more specifically, the relative orientation of the fillable bladder 120 in relation to the pistol grip handle 212 of the delivery device 200 can provide a number of benefits in some embodiments. For example, the implant 100 can be loaded onto the delivery device 200 in a predetermined orientation such that the location of the fillable bladder 120 in relation to the pistol grip handle 212 facilitates alignment of the bladder with a targeted surface region of the heart H during deployed of the implant 100 over the heat H. In such circumstances, a clinician may be able to ascertain the position of the fillable bladder 120 based on the position of the pistol grip handle 212. This feature can be advantageous, for example, during an implantation procedure when the fillable bladder 120 is within the chest cavity of a patient and therefore out of the direct sight of the clinician. For example, during use, the clinician will be estimate the location of the fillable bladder 120 relative to the targeted surface region of the heart based on the orientation of the pistol grip handle 212 in the clinician's hand.

In this embodiment illustrated in FIG. 6C, when viewing on an axial sight-line in a proximal direction at the distal end of the delivery device 200, the fillable bladder 120 is on the left side of the delivery device 200 (e.g., at the "9 o'clock" position) when the pistol grip handle 212 is extending vertically downward (e.g., at the "6 o'clock" position). Stated in another way, and as shown in the side views of FIGS. 6A and 6B, from the perspective of a clinician holding the pistol grip handle 212 vertically downward and in front of the clinician (e.g., see FIG. 16A), the fillable bladder 120 is located on the right side of the delivery device 200 (e.g., at the "3 o'clock" position relative to the "6 o'clock" position of the handle 212). Other embodiments may use different variations of orienting a fillable bladder in relation to the delivery device. For example, in some embodiments the fillable bladder may be located on the other side of the delivery device, on the upper or lower sides, or at any other position around the periphery of the barrel assembly 220.

Figure 7:
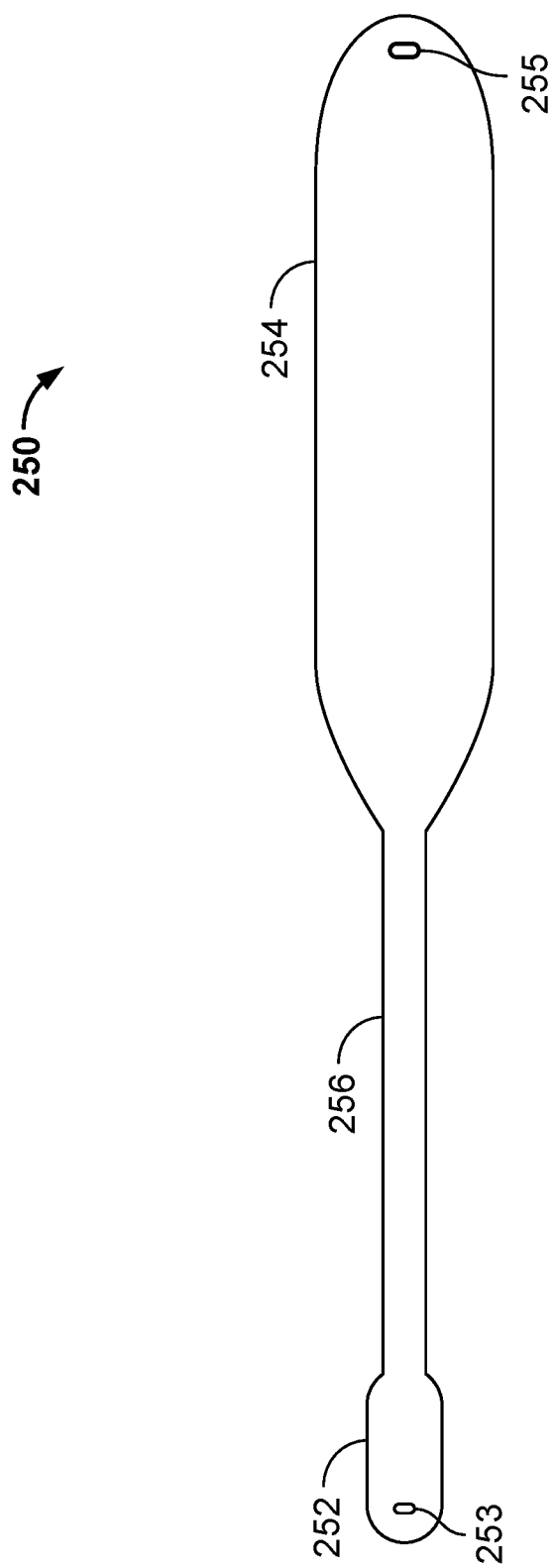
FIG. 7 is a front view of a low friction (e.g., lubricious) strip component for use with the implant delivery device of FIG. 6A, in accordance with some embodiments.

Referring now to FIG. 7 (in addition to FIGS. 6A and 6B), some embodiments of the delivery device 200 include multiple epicardial management strips 250 that are positioned between the barrel 222 and the implant 100 during advancement of the implant 100 toward and over the apex of the heart H. As mentioned previously, epicardial management strips 250 can be used to assist with the installation of an implant 100 onto the heart H. As the implant 100 is slid over the heart H, the epicardial management strips 250 can be temporarily positioned between the epicardial surface of the heart and the implant 100. The epicardial management strips 250 can be made of a flexible, lubricious material to provide low-friction surface area that facilitates the sliding advancement of the implant 100 onto the heart. In this embodiment, the epicardial management strips 250 are components of the delivery device 200 and are preloaded on the delivery device 200, as is the implant 100. After the implant 100 is installed and seated in the selected position (e.g., with the hem 113 positioned in the atrial-ventricular groove of the heart H), the epicardial management strips 250 are removed from the chest cavity.

The epicardial management strips 250 can be made from a variety of different materials, including but not limited to, polytetrafluoroethylene (PTFE), expanded-PTFE (ePTFE), ultra-high-molecular-weight polyethylene (UHMWPE), fluorinated ethylene propylene (FEP), perfluoroalkoxy (PFA), and the like. In some embodiments, a lubricious coating or surface treatment can be applied to the material used to make the epicardial management strips 250. The materials selected to construct the epicardial management strips 250 have properties such as a low coefficient of friction, biocompatibility, and resistance to absorption of liquids. The thickness of the epicardial management strips 250 can be selected to provide the desired levels of lateral flexibility, column strength, and other mechanical properties. For example, in some embodiments the thickness of the epicardial management strips 250 are in the range of about 0.010 inches to about 0.100 inches (about 0.25 mm to about 2.54 mm).

In this embodiment, there are a total of six epicardial management strips 250. The epicardial management strips 250 extend from the actuators 224, over the external surface of the barrel 222, under the implant 100, and terminate where the implant 100 is coupled to the delivery device 200. In this embodiment, the epicardial management strips 250 include a proximal portion 252, a distal portion 254, and an intermediate portion 256 therebetween. The proximal portion 252 includes a first clearance hole 253 that is configured to engage with a barbed protrusion located on the actuators 224. The distal portion 254 is a widened area that slides on the heart's surface as an implant 100 is being installed. A second clearance hole 255 is located at the distal portion 254. The second clearance hole 255 is configured to allow a portion of the mesh material of the implant 100 to pass therethrough, whereafter the portion of mesh material is releasably coupled with the delivery device 200.

Referring now to FIGS. 8A-8E, the delivery device 200 is illustrated from multiple perspectives. In these views, the implant 100 and epicardial management strips 250 are not shown for purposes of illustrating the barrel assembly 220 and other components distal thereto. As described previously, the delivery device 200 includes the main body 210, barrel assembly 220, and heart stabilizer assembly 230. In addition, the delivery device 200 includes multiple elongate arm assemblies 240. As described further herein, the arm assemblies 240 can be individually and selectively extended from the barrel assembly 220 to convey the implant 100 onto a heart. Thereafter, the arm assemblies 240 can be decoupled from the implant 100 and retracted from the patient's chest space (along with the epicardial management strips 250 not shown in FIGS. 8A-8E), while the implant 100 remains in a selected position on the patient's heart H (e.g., with the hem 113 positioned in the atrial-ventricular groove of the heart H).

The arm assemblies 240 extend from the distal end of the barrel assembly 220 and terminate at free ends 244. A proximal end of each arm assembly 240 is coupled to an actuator 224. In this embodiment, the delivery device 200 includes six actuators 224 and six corresponding arm assemblies 240. Other embodiments may include more than six or fewer than six actuators and arm assemblies. In this embodiment, each actuator 224 is coupled to one and only one arm assembly 240, and each arm assembly 240 is coupled to one and only one actuator 224. However, in some embodiments, more than one arm assembly may be coupled to one actuator. As described further herein, the distal free ends 244 of the arm assemblies 240 are configured to releasably couple with the mesh material of an implant (refer, for example, to FIG. 6C).

Figure 8A:
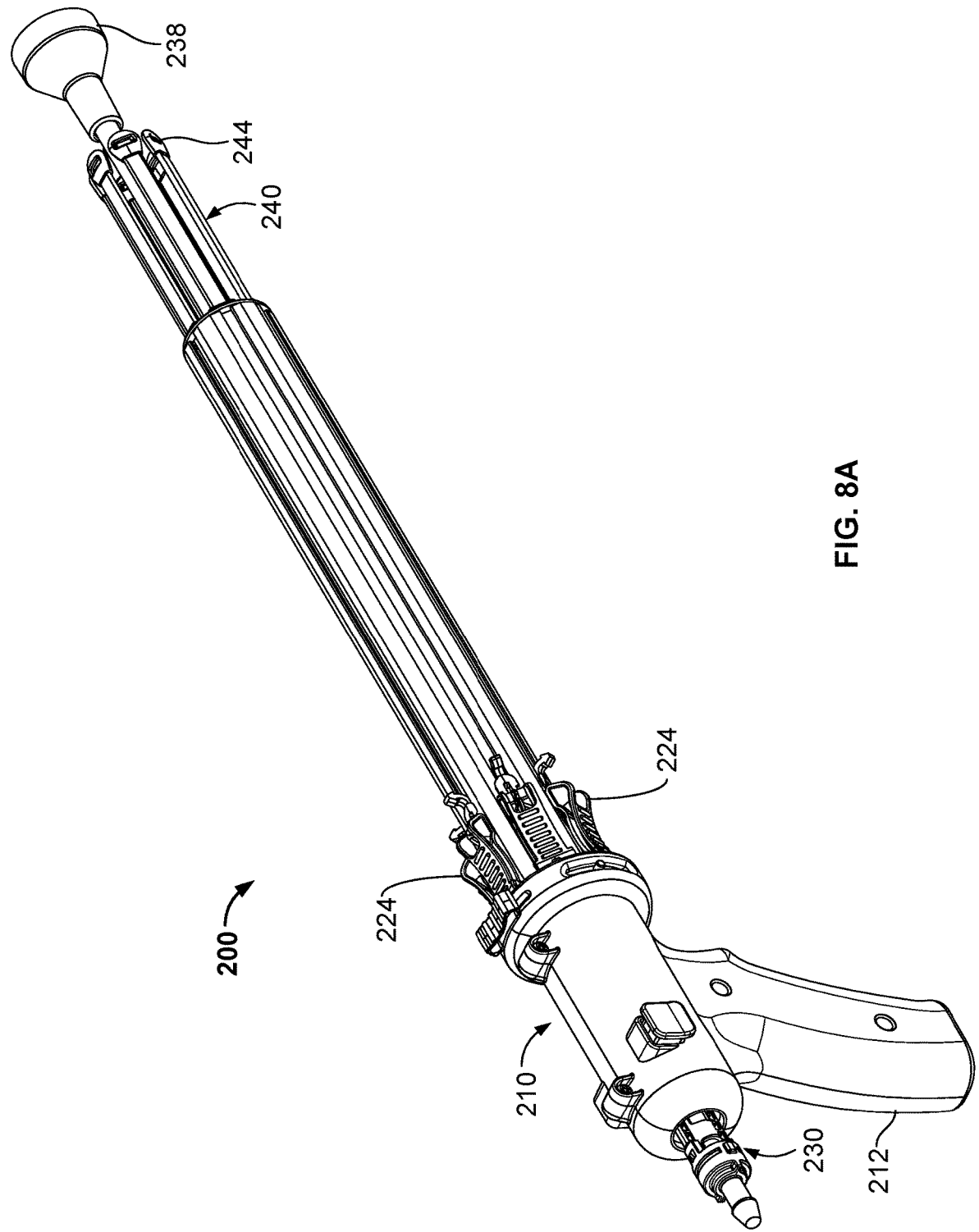
FIGS. 8A-8E are multiple perspective views of an implant delivery device with the heart stabilizer in an extended position, in accordance with some embodiments.
Figure 8B:
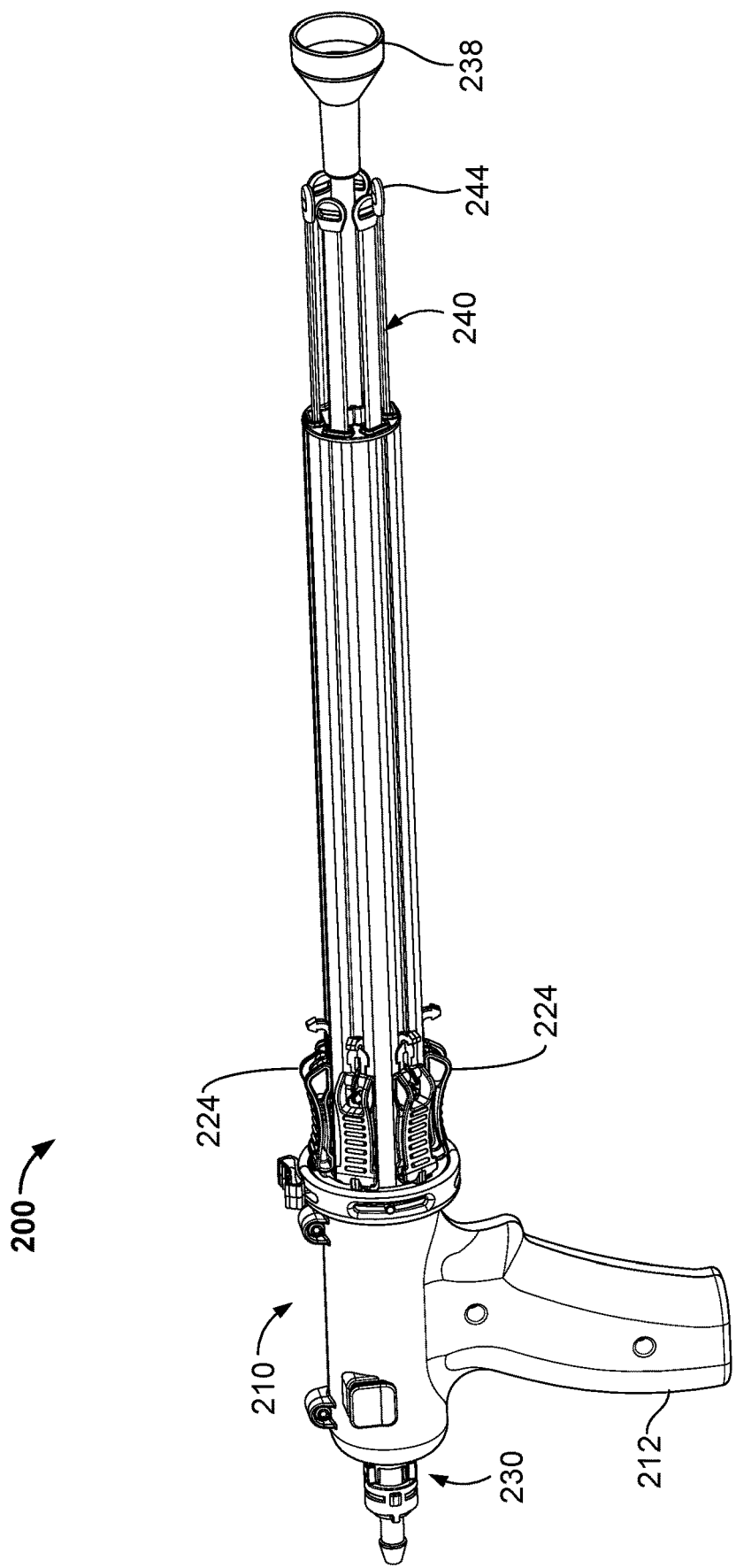
Figure 8C:
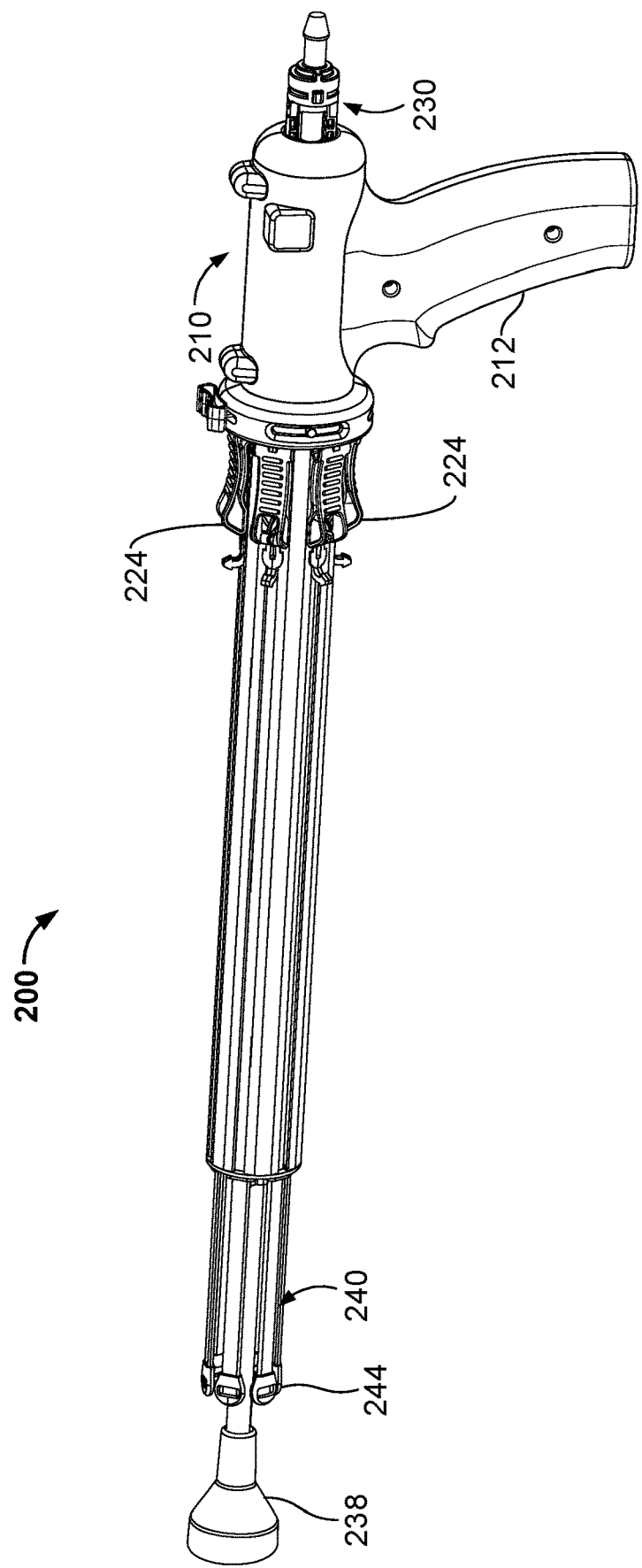
Figure 8D:
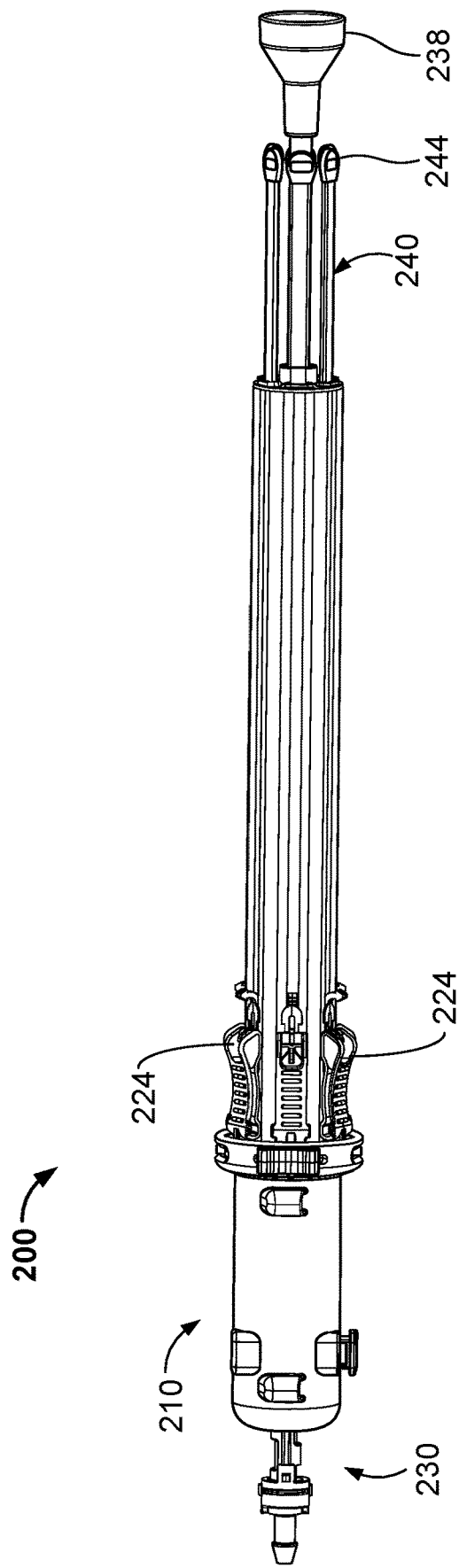
Figure 8E:
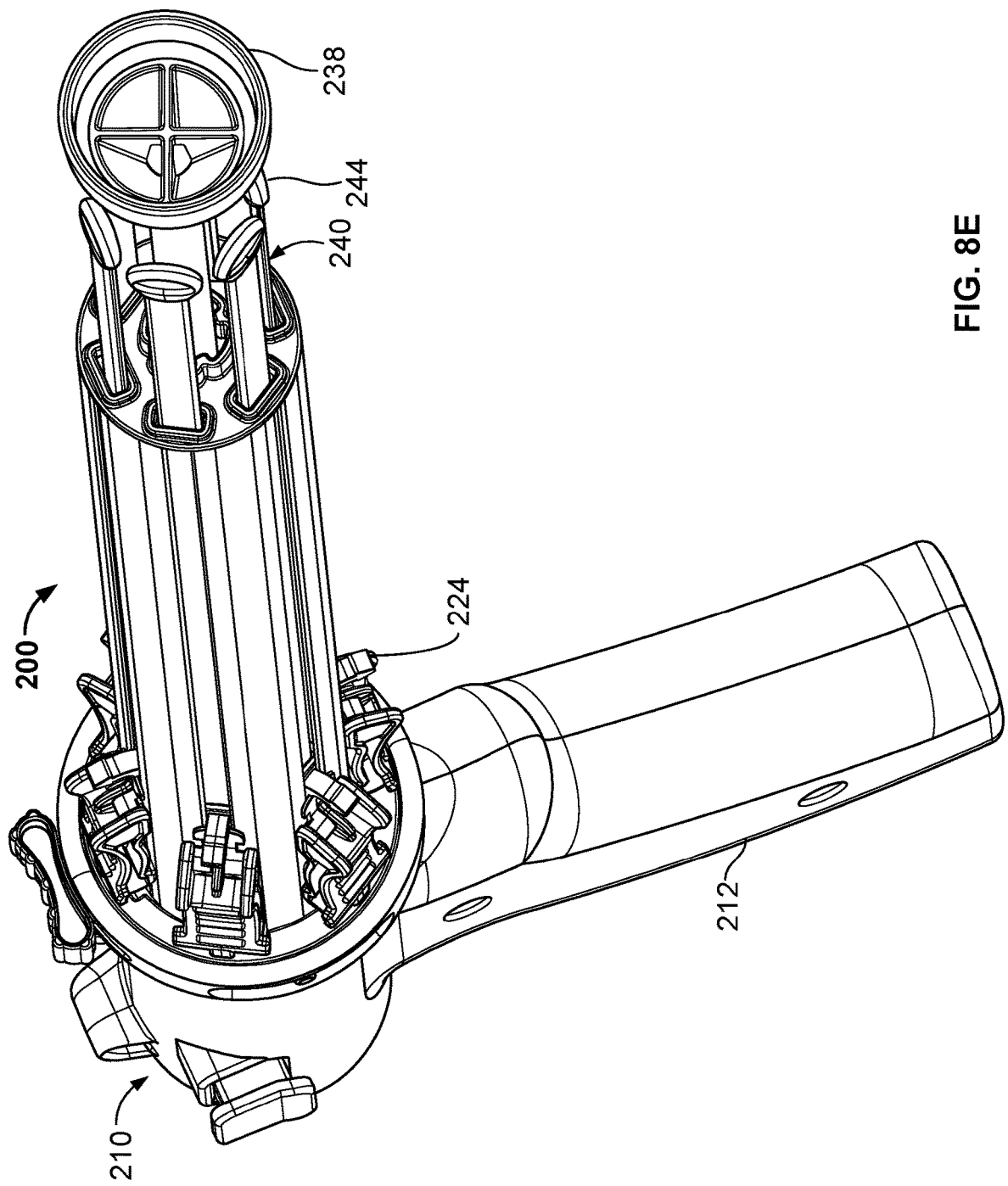
Figure 8F:
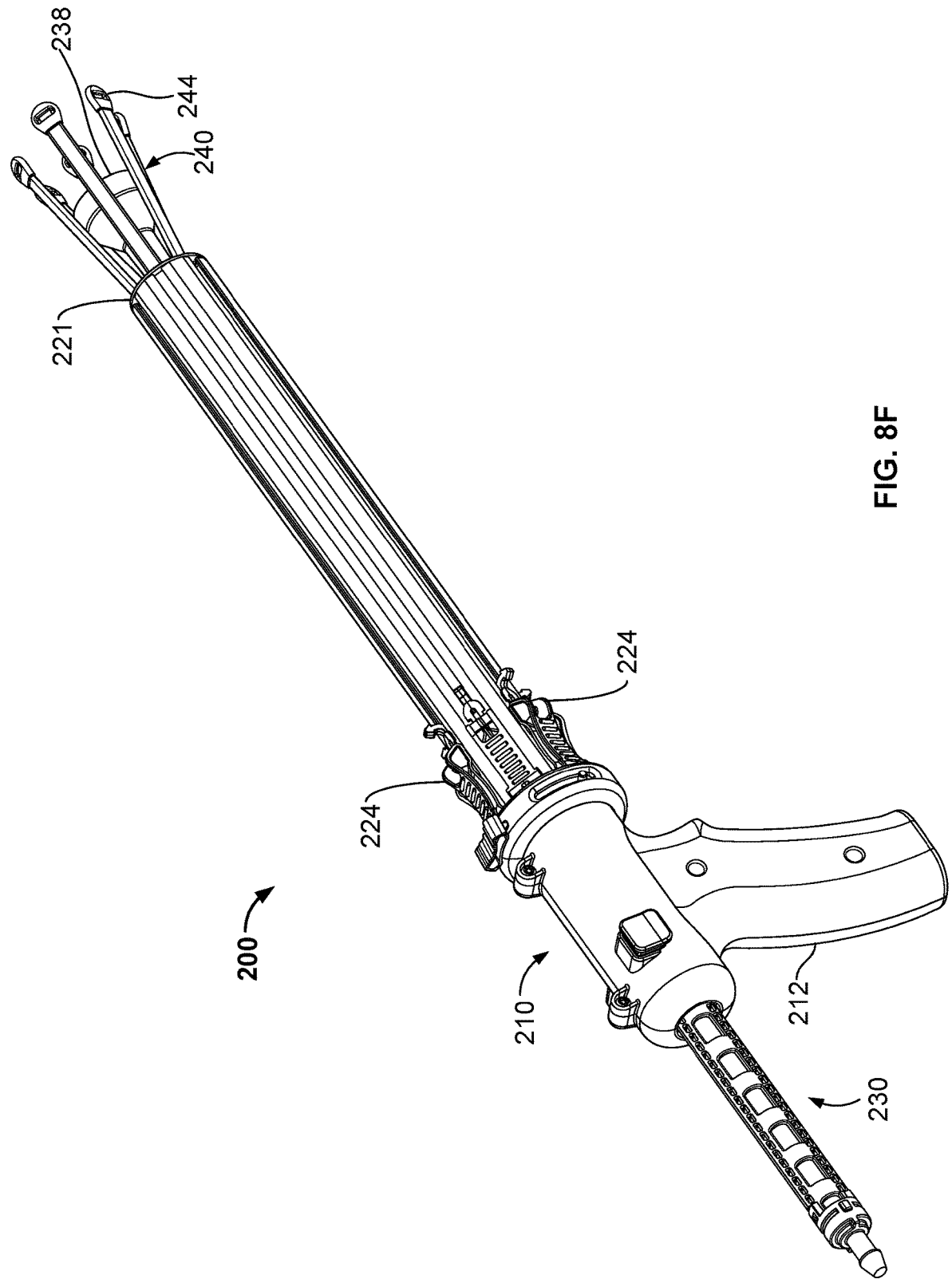
FIG. 8F is a perspective view of the implant delivery device of FIGS. 8A-8E, with the heart stabilizer in a retracted position.
Figure 8G:
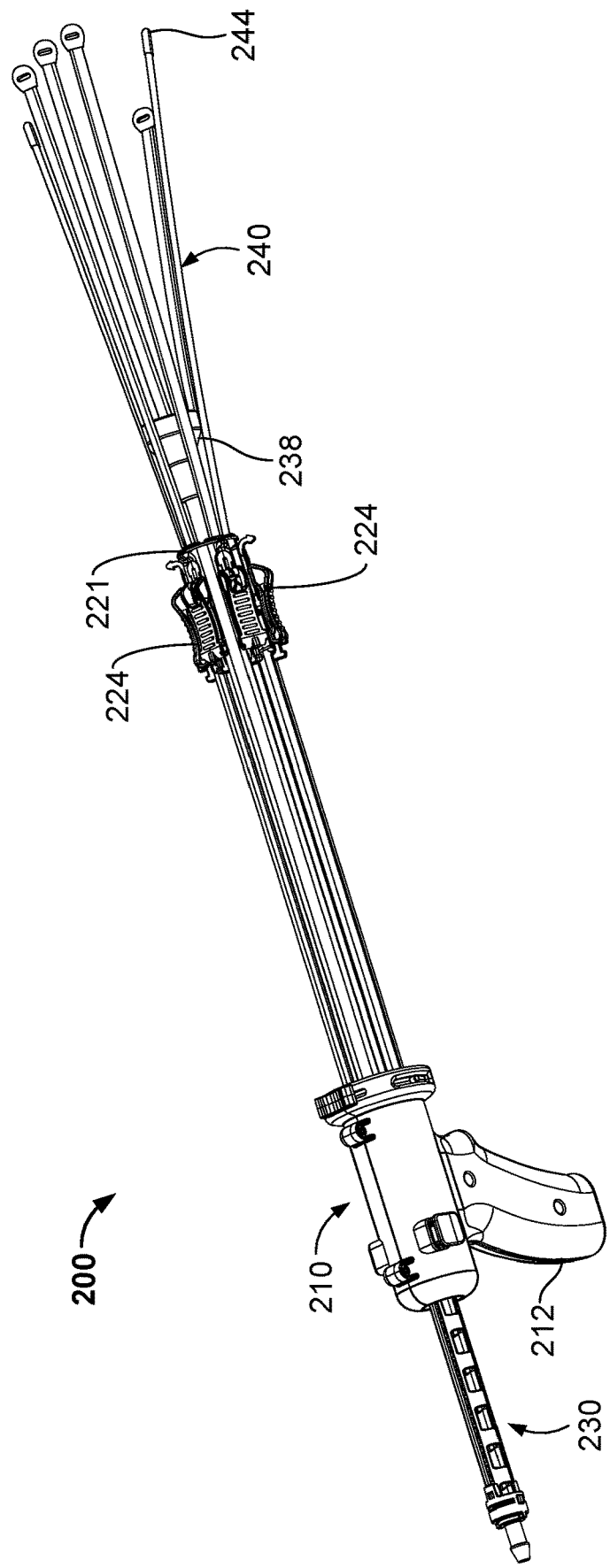
FIG. 8G is a perspective view of the implant delivery device of FIGS. 8A-8E, with the heart stabilizer in a retracted position and multiple elongate actuator arms in fully extended positions.

Referring to FIGS. 8F and 8G, the elongate arm assemblies 240 are laterally flexible and axially extendable members. That is, each of the arm assemblies 240 can elastically bend laterally and translate axially in the depicted embodiment. Such properties can be useful for conveying an implant through a relatively small chest opening, into the pericardial cavity of a patient, and then onto the ventricles of the patient's heart H in an atraumatic manner.

In this embodiment of the delivery device 200, the elongate arm assemblies 240 can be manually adjusted between a retracted position (depicted in FIG. 8F) and an extended position (depicted in FIG. 8G). In the extended position, the elongate arm assemblies 240 project distally from the distal end 221 of the barrel assembly 220 to a greater extent than when the arm assemblies 240 are in the retracted position. This ability of the arm assemblies 240 to extend distally is useful for the purpose of conveying an implant onto the heart of a patient. That is, while the distal end 221 of the barrel assembly 220 remains outside of the chest cavity, the arm assemblies 240 can be extended through a chest incision, and then extended into the chest cavity of the patient. The arm assemblies 240 can be extended further to project around the ventricles of the patient's heart to place the implant 100 onto the heart H (e.g., refer to FIGS. 1B, 4A, and 4B). The flexibility of the arm assemblies 240 can be useful because the arm assemblies sustain flexure during the minimally invasive implantation procedure. For example, after passing through the chest incision, at least some of the arm assemblies 240 thereafter bend to follow the contours of the heart H. Because the arm assemblies 240 are laterally compliant, the arm assemblies 240 can enter the chest through a small incision (e.g., a mini-thoracotomy) and elastically flex within the chest cavity to convey an implant 100 onto the patient's heart H.

In the depicted embodiment, the arm assemblies 240 can be extended and retracted by moving the arm actuators 224. That is the case, because the proximal ends of the arm assemblies 240 are coupled to the actuators 224. In order to axially move an arm assembly 240, the corresponding actuator 224 can be slid along the splined elongate barrel 222. For example, because the actuators 224 are located near the proximal end of the splined elongate barrel 222 in FIG. 8F, the arm assemblies 240 are in retracted positions. In contrast, because the actuators 224 are located near the distal end of the splined elongate barrel 222 in FIG. 8G, the arm assemblies 240 are in extended positions.

Figure 9A:
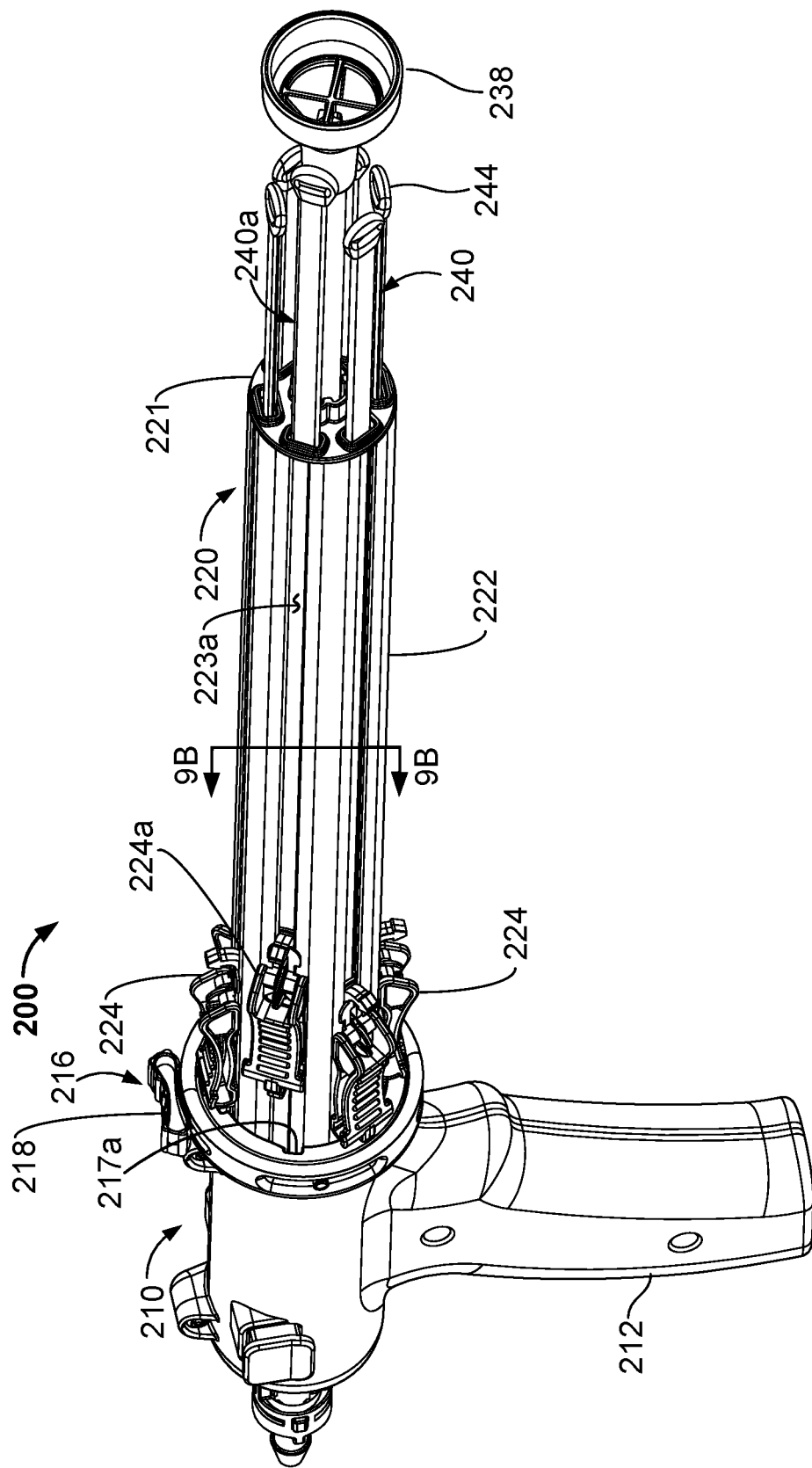
FIG. 9A shows a perspective view of the implant delivery device of FIGS. 8A-8E, with one of its elongate arms in a partially extended position.
Figure 9B:
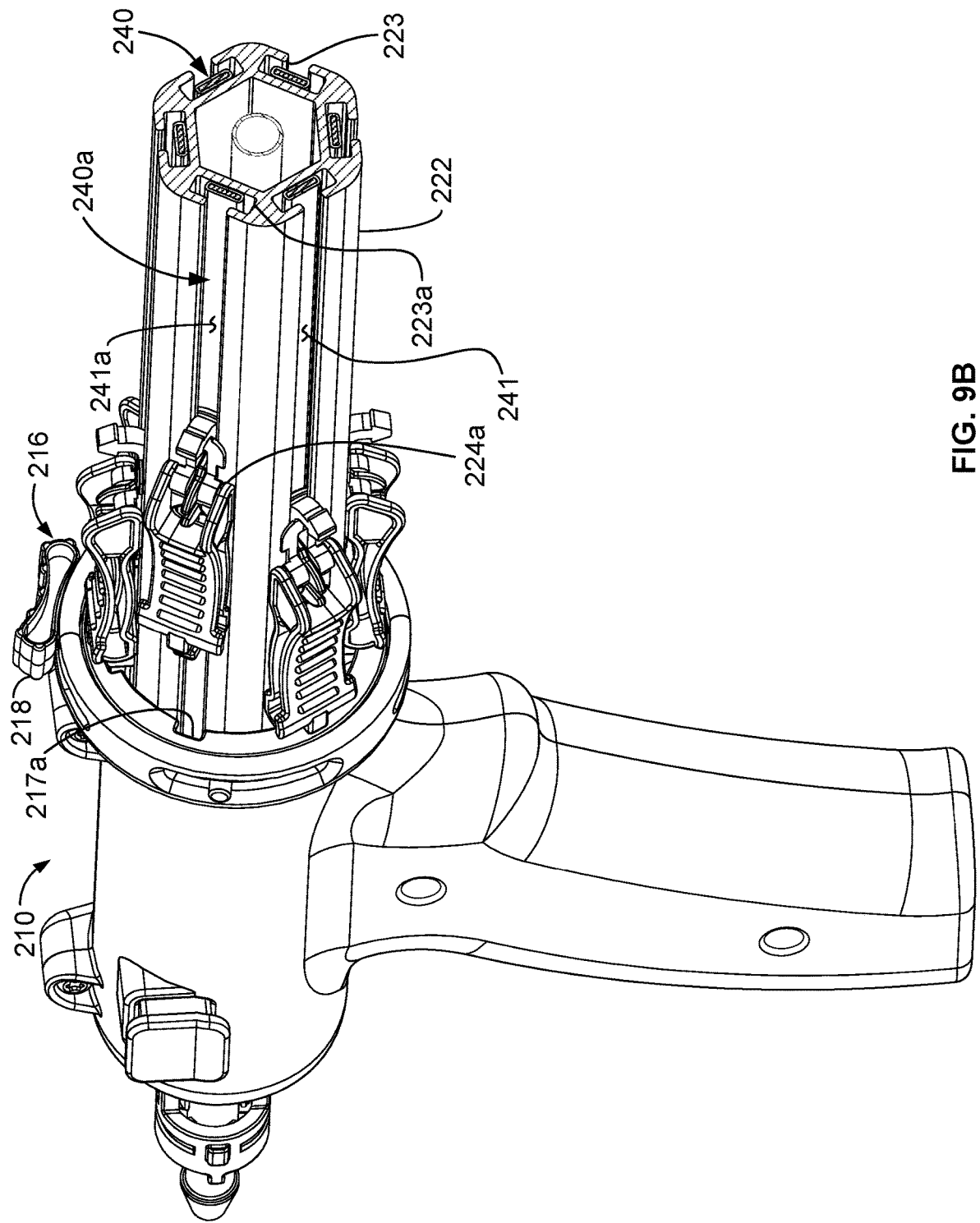
FIG. 9B is a partial perspective and partial cross-sectional view of the implant delivery device of FIG. 9A, the cross section taken along lines 9B shown in FIG. 9A.
Figure 9C:
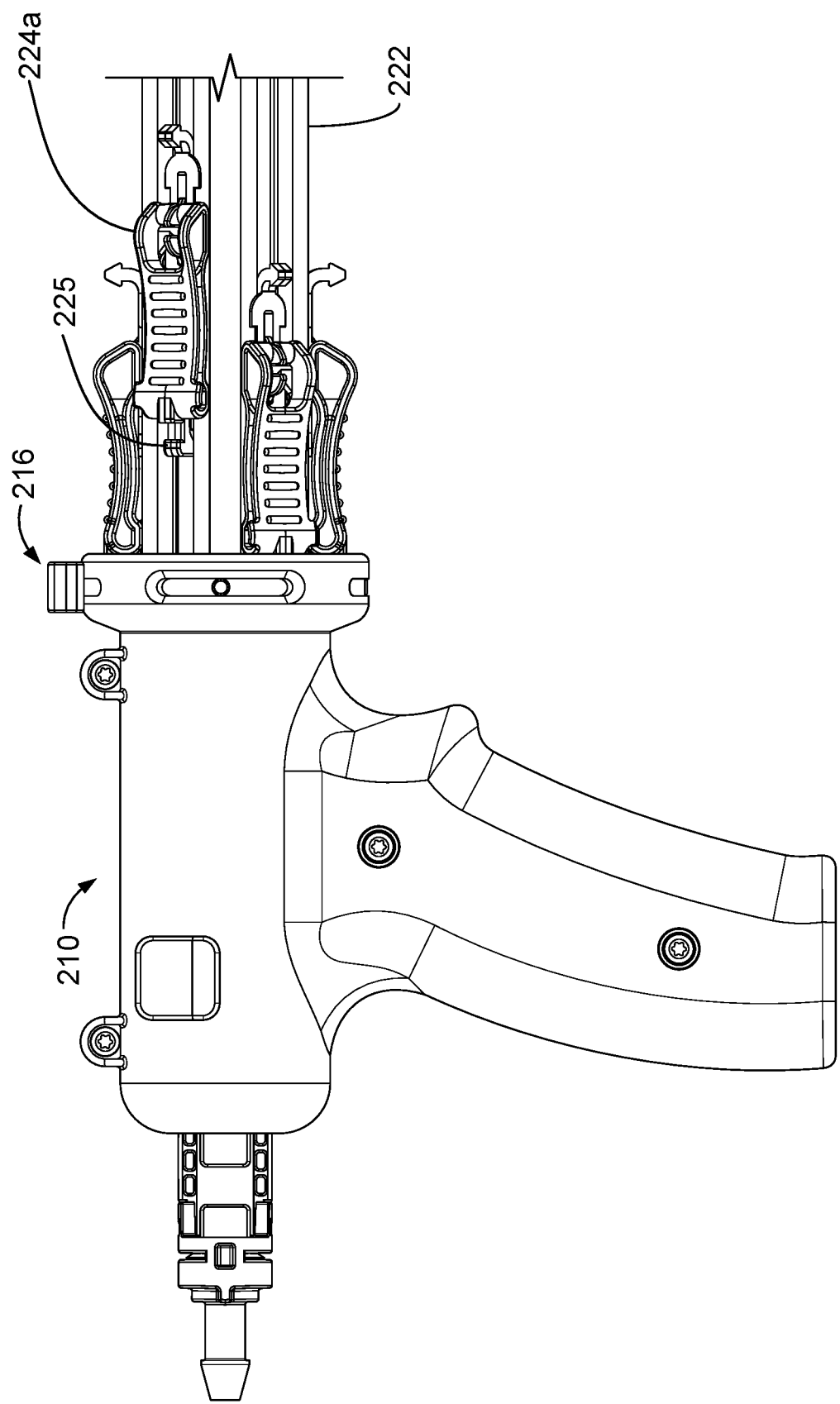
FIG. 9C is a view of a proximal portion of the implant delivery device of FIGS. 9A-9B.
Figure 10:
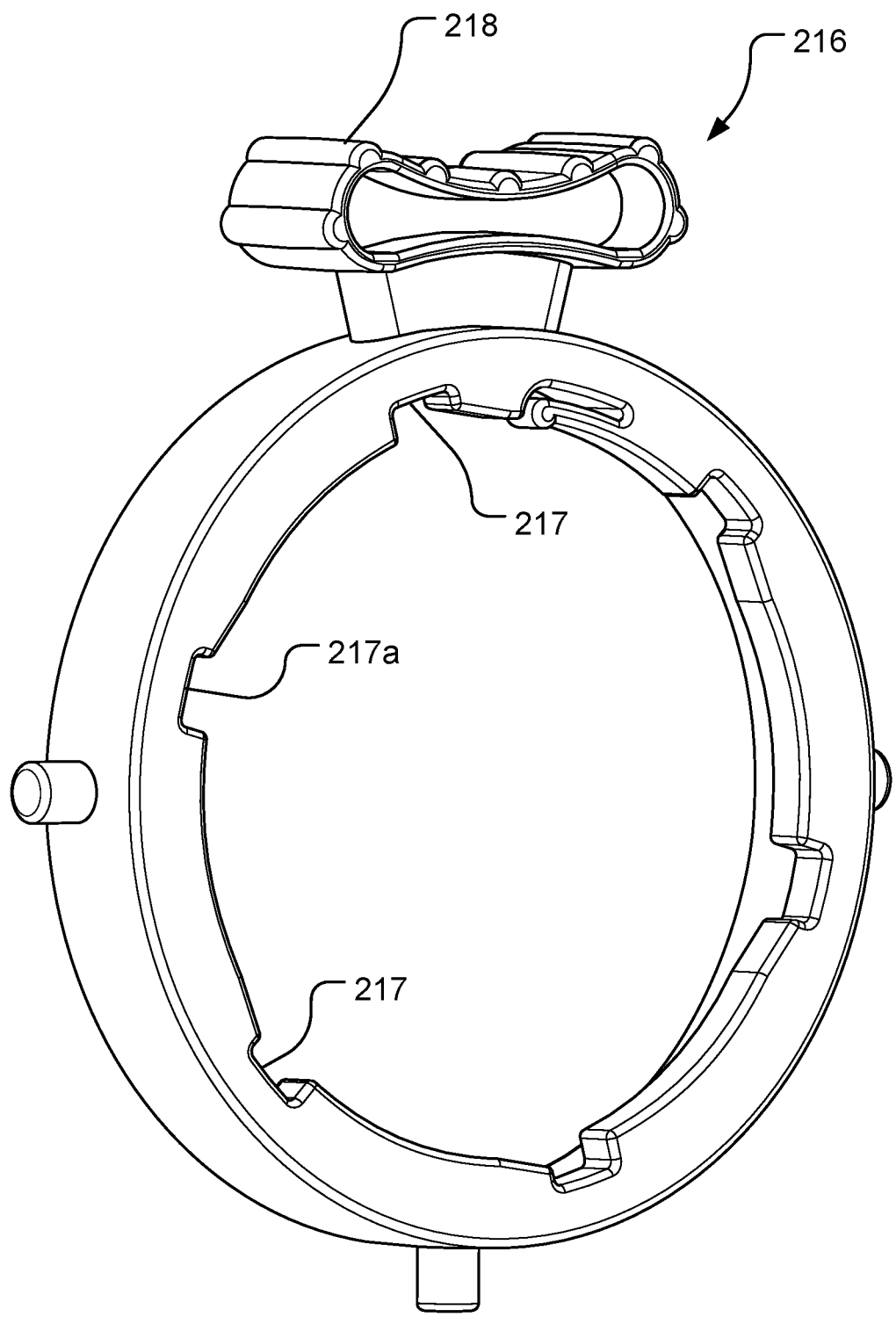
FIG. 10 is a perspective view of an actuator arm retainer ring component of the implant delivery device of FIG. 9A, in accordance with some embodiments.

Referring to FIGS. 9A-9C, the arm actuators 224, and the corresponding arm assemblies 240 coupled thereto, can be individually axially translated along the axis of the splined elongate barrel 222. For example, arm actuator 214a has been slid to a location that is distal of the other arm actuators 224. The corresponding arm assembly 240a is therefore extended further distally from the distal end 221 of the barrel 222 than the other arm assemblies 240. In some embodiments, multiple arm actuators 224 and arm assemblies 240 can be moved concurrently using a mechanical member that simultaneously translates the multiple arm actuators 224.

In this embodiment of the delivery device 200, the actuators 224 and the arm assemblies 240 are each individually slidably coupled with a spline 223 of the barrel 222. Each arm assembly 240 can be at least partially disposed in a corresponding spline 223 of the splined elongate barrel 222. For example, arm assembly 240a is partially disposed in spline 223a. The open space defined by the splines 223 is larger than the outer profile of the portion of the arm assemblies 240 disposed therein. As such, the arm assemblies 240 are free to slide axially within the splines 223. The arm actuators 224 are also partially disposed in or engaged with a particular spline 223. For example, arm actuator 224a is engaged with spline 223a. The arm actuators 224 include shuttle portions that have shapes that are complementary to the shape of the splines 223. As a result, the arm actuators 224 are coupled to, and are slidable in relation to, the splines 223.

Referring to FIGS. 9A-9C and FIG. 10, the main body 210 can include an actuator lock ring 216. The actuator lock ring 216 can be operated to retain the arm actuators 224 at the arm actuator's 224 proximal-most position on the barrel 222. This feature can be useful for purposes of restraining the arm assemblies 240 from inadvertently extending.

The actuator lock ring 216 can be rotatably coupled to the main body 210. That is, in this embodiment the actuator lock ring 216 is coupled to, and is free to be manually rotated in relation to the main body 210. In addition, the actuator lock ring 216 can be manually rotated in relation to the barrel 222 and the arm actuators 224 slidably coupled thereto.

The actuator lock ring 216 includes a rotatable lock knob 218 that can be manually rotated to lock or unlock the actuators 224 to the main body 210. The actuator lock ring 216 also includes six slots 217 (shown in FIG. 10) that are disposed about the inner diameter of the ring 216. The slots 217 are configured to be selectively alignable with the splines 223 of the barrel 222. The slots 217 are also configured to receive actuator tabs 225 (refer to FIG. 9C) that are located on the proximal ends of the arm actuators 224. When the slots 217 of the actuator lock ring 216 are in alignment with the splines 223, and the arm actuators 224 are slid to the distal-most end of travel on the barrel 222, then the tabs 225 pass through the slots 217 and reside proximally to the slots 217. Thereafter, the actuator lock ring 216 can be rotated via the lock knob 218 such that the slots 217 are no longer aligned with the splines 223, thereby locking the arm actuators 224 to the main body 210. For example, in FIG. 9A the actuator lock ring 216 is in a rotary position where the slots 217 are not aligned with the splines 223. Therefore, the arm actuators 224, other than actuator 224a, are locked to the main body 210. In contrast, in FIG. 9B the actuator lock ring 216 is in a rotary position where the slots 217 are aligned with the splines 223. For instance, slot 217a is visibly aligned with slot 223a. Therefore, all of the arm actuators 224 are not locked to the main body 210. In result, the arm actuators 224 can be slid in relation to the main body 210 and splined barrel 222.

In the cross-sectional view of FIG. 9B, it can be seen that each of the arm assemblies 240 include an elongate hollow outer jacket 241. The hollow outer jacket 241 defines an open interior space, or lumen, that can contain another member, such as a core member 242 described in connection with FIGS. 11A-11B.

Figure 11A:
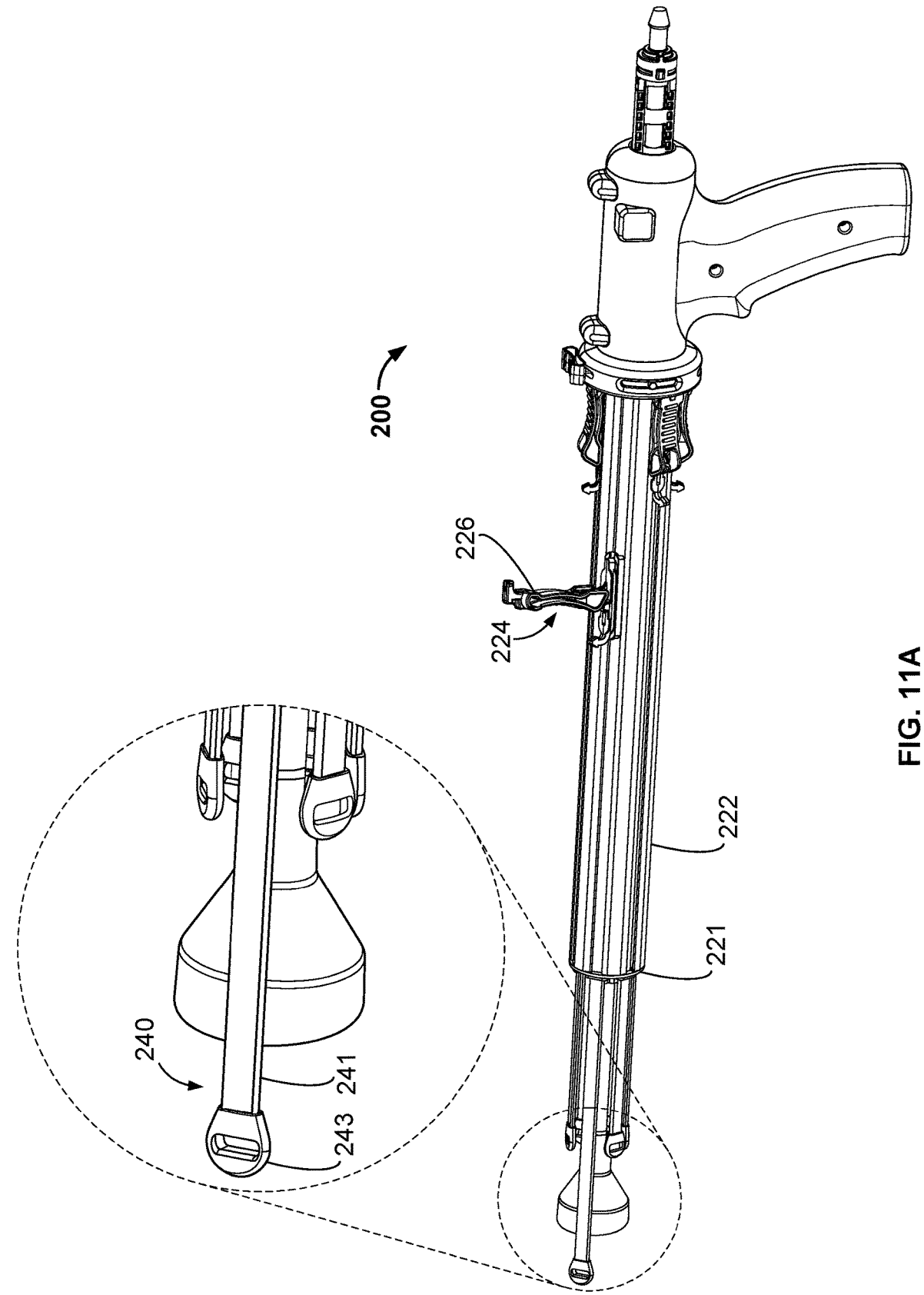
FIG. 11A is a perspective view of an implant delivery device with an elongate arm in an implant released position that enables the release of an implant from the elongate arm, in accordance with some embodiments.
Figure 11B:
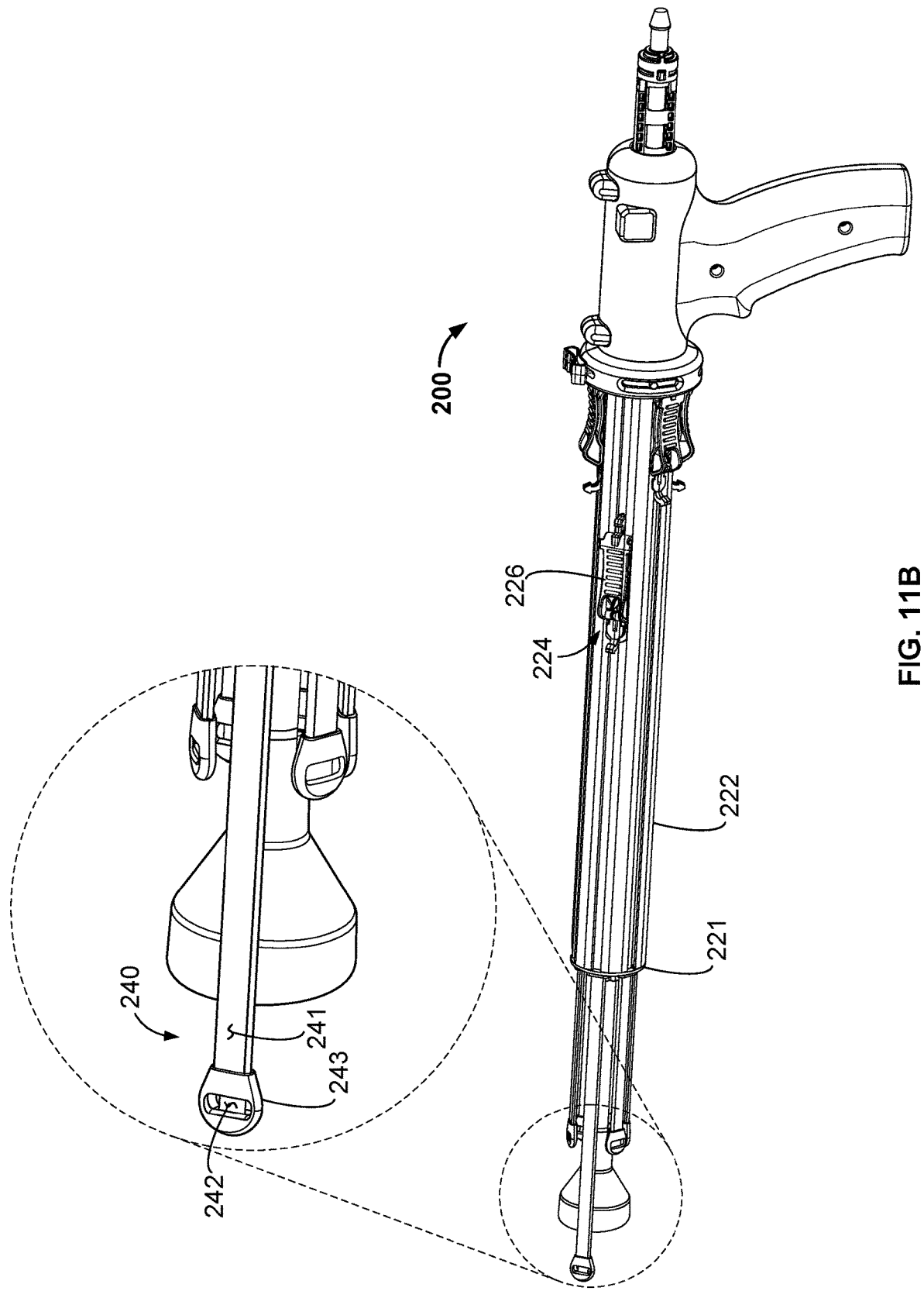
FIG. 11B is a perspective view of the implant delivery device of FIG. 11A with the elongate arm in an implant clamping position, in accordance with some embodiments.

Referring now to FIGS. 11A and 11B, in this embodiment each of the arm assemblies 240 include the hollow outer jacket 241, the core member 242, and an arm cap 243. The core member 242 is slidably disposed within the lumen of the hollow outer jacket 241. The arm cap 243 is affixed to the distal end of the hollow outer jacket 241. Therefore, the core member 242 can also be slid in relation to the arm cap 243. In other embodiments, other configurations of the arm assemblies 240 can be used while providing similar functionality.

As described previously, arm actuators 224 are coupled to corresponding arm assemblies 240. For example, when an arm actuator 224 is axially translated in relation to the splined barrel 222, a corresponding arm assembly 240 is extended or retracted from the distal end 221 of the barrel 222. As each arm assembly 240 is extended or retracted, the hollow outer jacket 241, core member 242, and arm cap 243 of the arm assembly 240 can be extended or retracted in equal distances, and in unison.

The arm actuators 224 are coupled to arm assemblies 240 in a second manner that allows each actuator 224 to move the core members 242 of the corresponding arm assembly 240 relative to the hollow outer jacket 241 and arm cap 243. In particular, the arm actuators 224 are coupled to the core members 242 such that pivoting an actuator lever 226 of an arm actuator 224 can advance or retract a core member 242 of an arm assembly 240 in relation to the outer jacket 241 and arm end 243 of the arm assembly 240. The pivotable actuator lever 226 of an actuator 224 controls the core member 242 of the arm assembly 240 to which the actuator 224 is coupled.

The pivotable actuator lever 226 is shown pivoted away from the barrel 222 in FIG. 11A, such that the longitudinal axis of the pivotable actuator lever 226 is roughly perpendicular to the axis of the barrel 222. In contrast, the pivotable actuator lever 226 is shown pivoted toward the barrel 222 in FIG. 11B, such that the longitudinal axis of the pivotable actuator lever 226 is roughly parallel with the axis of the barrel 222. Such pivoting of the actuator lever 226 controls the axial position of the core member 242 in relation to the hollow outer jacket 241 and the arm cap 243. For example, in FIG. 11A no core member is visible within the window of the arm cap 243. In contrast, in FIG. 11B, the core member 242 is visible within the window of the arm cap 243. This comparison illustrates that, in this embodiment, when an actuator lever 226 is pivoted away from the barrel 222, a core member 242 is retracted in the axial direction. Conversely, when an actuator lever 226 is pivoted toward the barrel 222, a core member 242 is advanced distally in the axial direction.

This second manner by which arm actuators 224 are coupled to arm assemblies 240 can be operated independently of axially translating an arm actuator 224 in relation to the splined barrel 222 to extend or retract a corresponding arm assembly 240. So, for example, at any axial position of an arm actuator 224, the actuator lever 226 can be pivoted to advance or retract the core member 242. Further, the two movements (axial translation of an arm actuator 224 and pivoting of the actuator lever 226) can be performed contemporaneously.

The advancing and retracting of the core members 242 within the windows of the arm ends 243 can be advantageously used for releasably coupling an implant to the delivery device 200. In some embodiments, a portion of the mesh body 110 of the implant 100 can be crimped and contained within a window of an arm end 243 (refer, for example, to FIG. 6C) when the core member 242 is in the advanced position. When it is desired to release the implant 100 from the delivery device 200, the actuator levers 226 can be pivoted to retract the core members 242, and the mesh material will then no longer be crimped within the windows of the arm ends 243, and the implant 100 can then be separated from the delivery device 200. Thereafter, the arm assemblies 240 can be retracted from the patient's chest space (along with the epicardial management strips 250 not shown in FIGS. 8A-11B), while the implant 100 remains in a selected position on the patient's heart H (e.g., with the hem 113 positioned in the atrial-ventricular groove of the heart H).

Figure 12A:
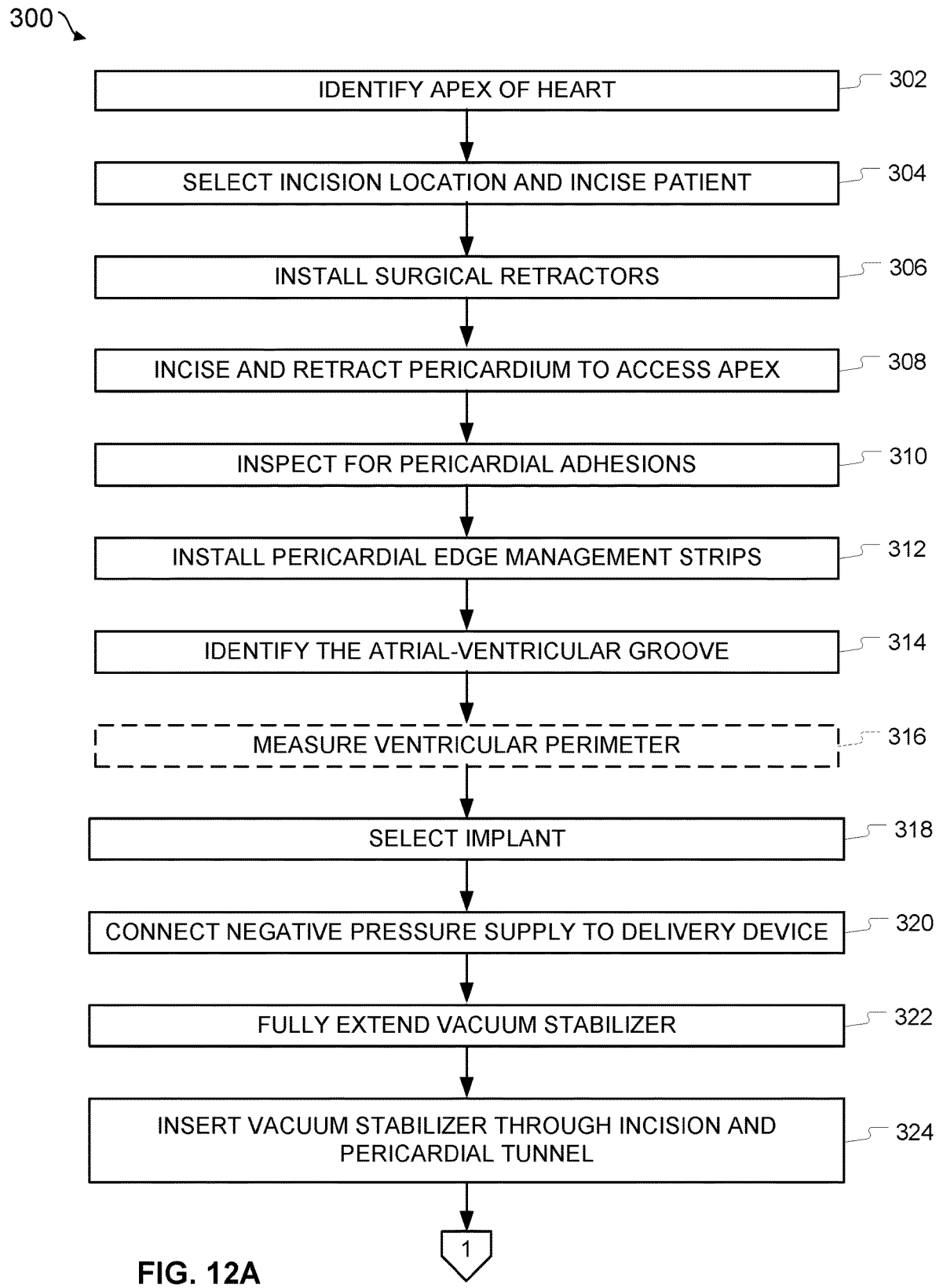
FIGS. 12A-12C is a three-part flowchart of an example method for installing an implant in a patient to treat a heart condition, in accordance with some embodiments.
Figure 12B:
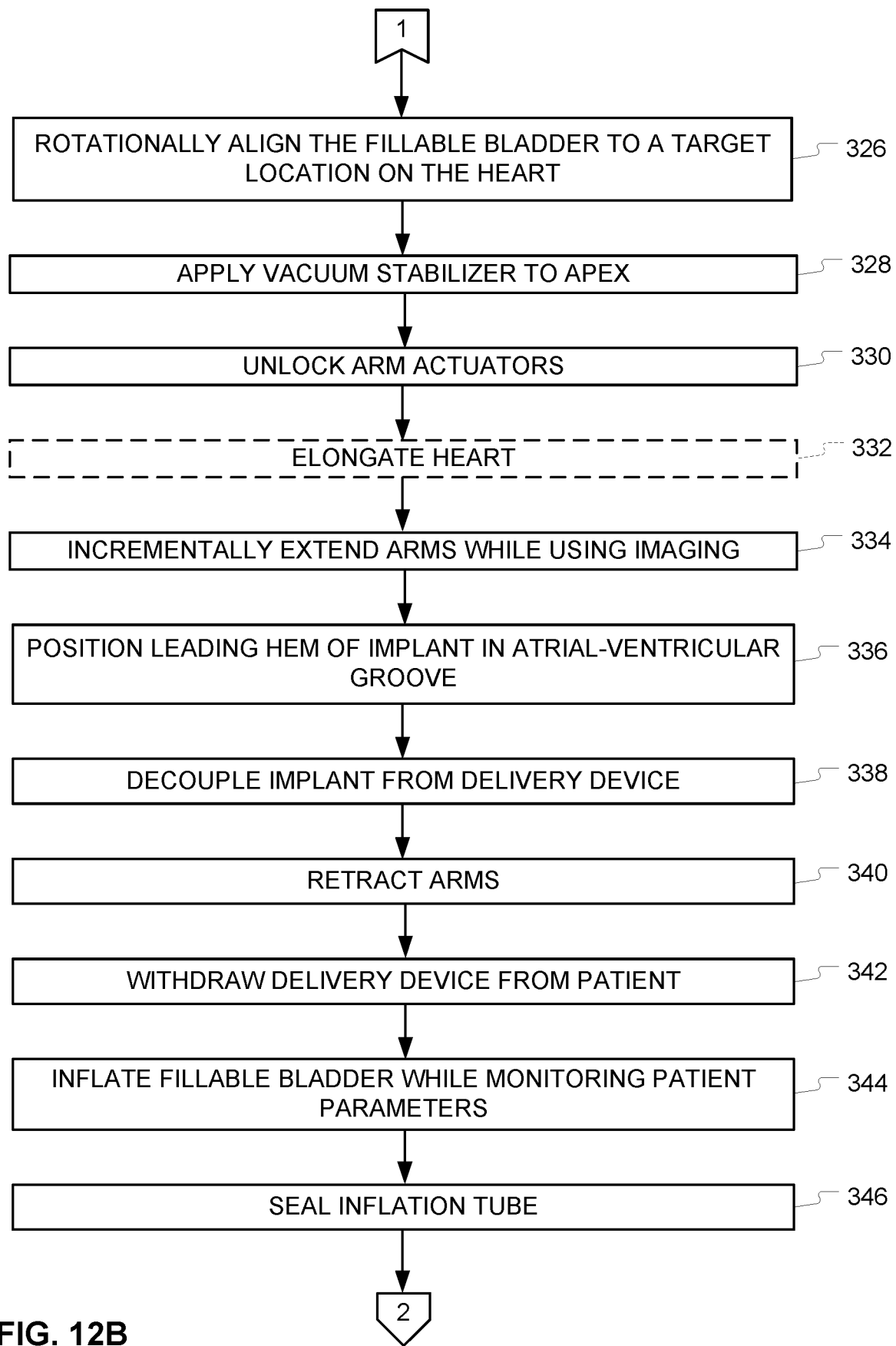
Figure 12C:
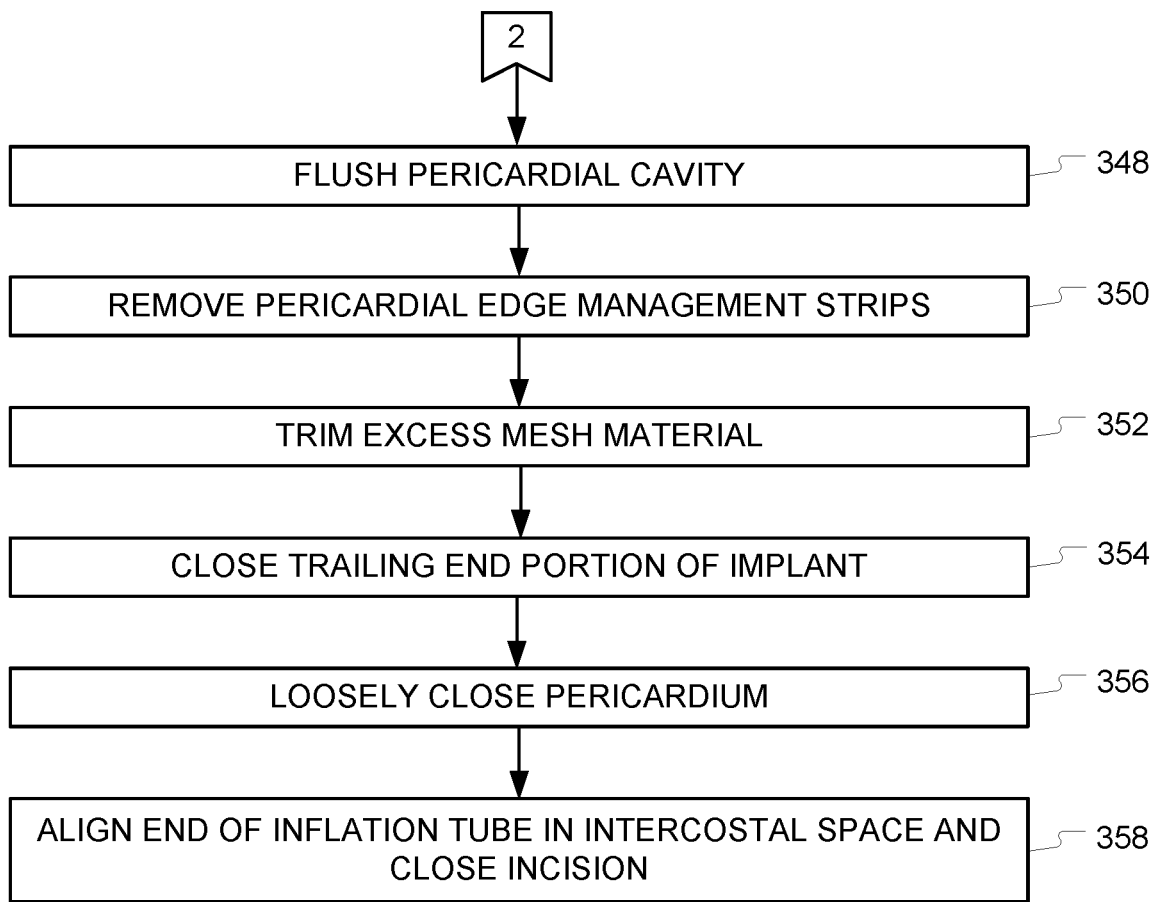

Referring now to FIGS. 12A-12C, some embodiments described herein include a method 300 for installing an implant in a patient to treat a heart condition. In some implementations, such heart conditions can include, but are not limited to, functional mitral regurgitation, tricuspid valve regurgitation, and congestive heart failure. In some embodiments of the method 300, a cardiac implant (including but not limited to the implant 100 described above) is implanted to surround an exterior portion of the patient's heart. The implant employed in the method 300 may include one or more fillable bladders. The fillable bladders can be configured for installation at a selected position on the targeted epicardial region of the heart (for example, on a posterior wall of the heart adjacent the mitral valve) so that the fillable bladder will exert a localized pressure to induce the remodeling of a portion of the heart when the fillable bladder is inflated. In the example of positioning a fillable bladder on a posterior wall of the heart adjacent the mitral valve, the fillable bladder provides localized pressure that in turn is applied to a posterior portion of the mitral valve annulus (refer to FIG. 1B), thus bringing the leaflets of the valve into closer proximity with one another and treating a mitral valve regurgitation problem.

Referring to FIG. 12A, in some implementations of the method 300, step 302 includes identifying the apex of a patient's heart. This step may involve the use of one or more imagining modalities. For example, in some embodiments, radiographic and/or transthoracic echocardiographic information is attained to assist in the identification of the apex of the heart.

At step 304 in some implementations of the method 300, a location for an incision to access the patient's heart is selected, and then an incision through the patient's skin is made. In some embodiments, the selected location of the incision will allow access to the apex of the heart in alignment with the long axis of the heart. Such an incision can allow an implant delivery device to be inserted into the patient's chest cavity substantially coaxially with the heart (e.g., as in step 326). Therefore, the location for the incision can be made at least partly based on the location of the apex of the patient's heart as ascertained in step 302. In some implementations, an intercostal incision location is selected. For example, in particular implementations the fifth intercostal space may be selected. However, the selected incision location can be patient-specific. In some implementations, the incision comprises a mini-thoracotomy heart access procedure. In some embodiments of method 300, a minimum size of incision is recommended. For example, for the delivery device 200 described above, a minimum incision of 7 cm is recommended, although that is optional in some implementations.

At step 306 in some implementations of the method 300, surgical retraction is performed to create and maintain a surgical passageway through the patient's incised skin. In some implementations, a low-profile retractor is used. In some embodiments of method 300, a separation distance of the retractor blades is recommended. For example, when the delivery device 200 described above will be used, the retractor blades should be separated by at least about 4 cm.

At step 308 in some implementations of the method 300, the pericardium is incised and retracted to provide access to the heart's apex. In some embodiments, the selected location of the incision will allow access to the apex of the heart in alignment with the long axis of the heart. In some embodiments of method 300, a minimum size of incision is recommended. For example, for the delivery device 200 described above, a minimum incision of 7 cm is recommended, although that is optional. The edges of the pericardium can be retracted by suturing the edges to the surrounding tissues.

At step 310 in some implementations of the method 300, an inspection is made for pericardial adhesions. Pericardial adhesions are an attachment of the pericardium to the heart muscle. In some implementations, contrast agent solution may be injected into the pericardium to enhance visualization of pericardial adhesions. If pericardial adhesions that may impede complete circumferential access to the heart are identified, the clinician may abandon the method 300 at this point.

At step 312 in some implementations of the method 300, multiple pericardial edge management strips (PEMS) are installed. The PEMS can be used to cover exposed edges of the pericardium, and to create a clear tunnel for access (e.g., by delivery tool 200) to the apex of the heart. In some implementations, four to six PEMS are installed. In other implementations, fewer than four or more than six PEMS may be installed. The PEMS are sterile devices.

Figure 13A:
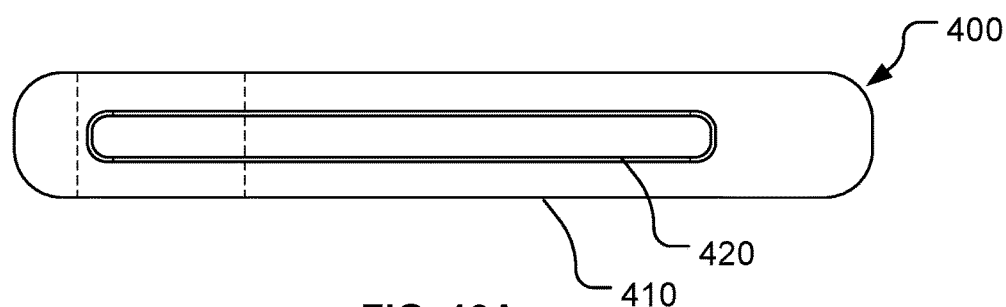
FIGS. 13A and 13B are top and perspective view of a device for facilitating an open surgical access passageway to the patient's heart, in accordance with some implementations of the method of FIGS. 12A-12C.
Figure 13B:
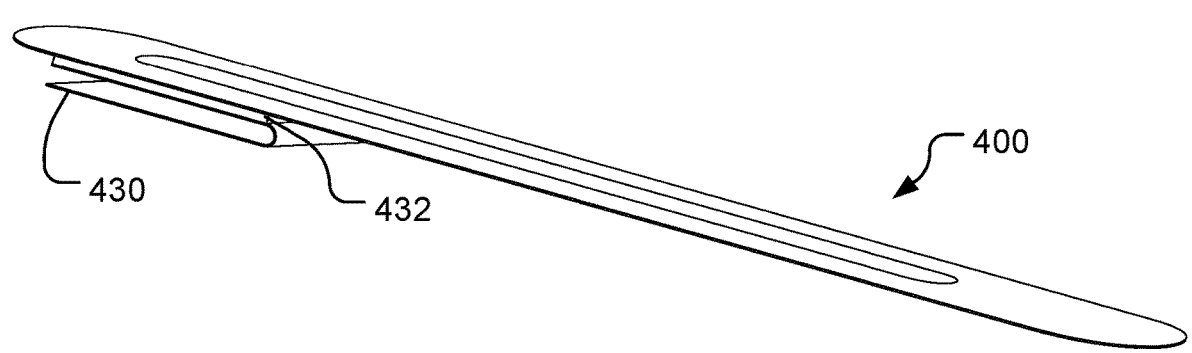

One example embodiment of PEMS is illustrated in FIGS. 13A and 13B. As shown, in some embodiments the PEMS 400 includes a masking member 410, a malleable member 420, and an adhesive member 430. The malleable member 420 and the adhesive member 430 can be attached to the masking member 410. In some embodiments, the malleable member 420 is disposed between multiple layers of masking member 410 material. The masking member 410 can be a flexible biocompatible film such as Teflon, polyester, polyurethane, and the like. The malleable member 420 can be a thin gauge metallic material, such as a stainless steel, titanium, and the like, or alloys thereof. The adhesive member 430 can be a pressure-sensitive biocompatible material such as a medical-grade acrylic adhesive, or other medical-grade adhesives. The adhesive member 430 can comprise an adhesive pad or be coated onto the masking member 410. The adhesive member 430 is covered by a liner 432 that is removed when the PEMS 400 are put into use.

Figure 13C:
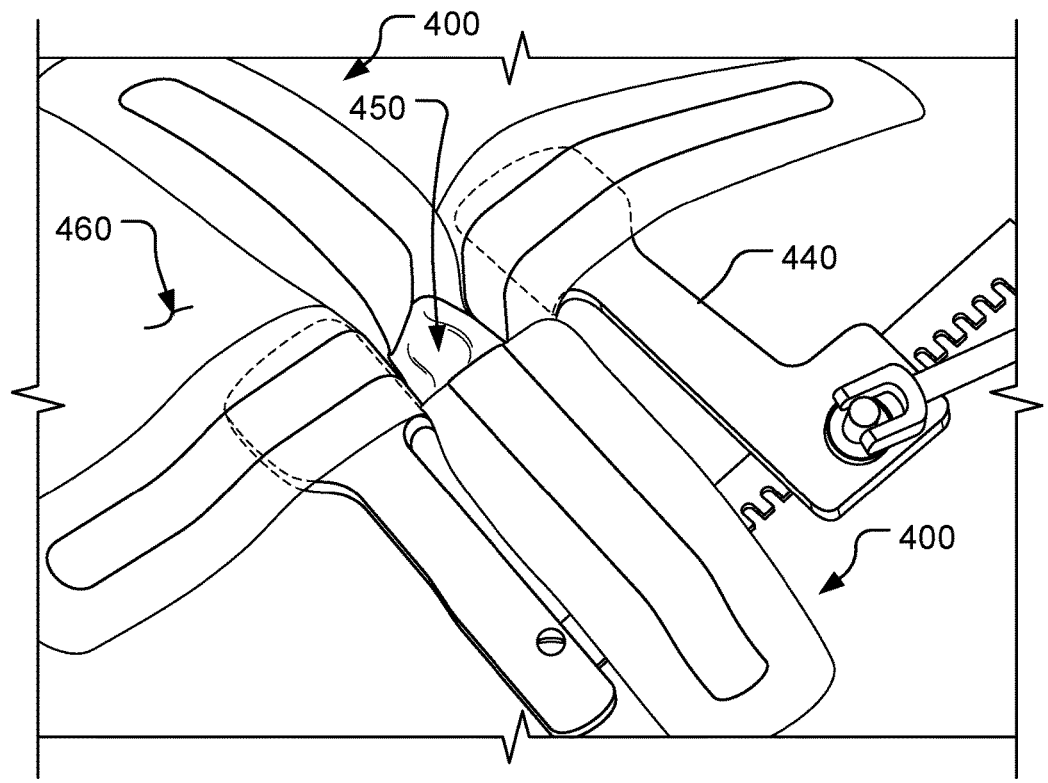
FIG. 13C is a perspective view of multiple ones of the device of FIGS. 13A and 13B in use on a patient, in accordance with some implementations of the method of FIGS. 12A-12C.

One non-limiting example of step 312 (using the PEMS 400) is illustrated in FIG. 13C. A retractor device 440 for spreading open an incision in the chest 460 of a patient depicted. Four PEMS 400 are partially inserted in the chest cavity of a patient to create an access tunnel 450. The end opposite the adhesive member 430 is inserted through the incision and into the pericardial space. Care is used to ensure that the inserted end of the PEMS 400 is within the pericardial space and is not inserted too deep into the incision such that the PEMS 400 will interfere or damage other cardiac structures. The exposed portion of the PEMS 400 is bent back (thereby deforming the malleable member 420) so that the PEMS 400 is in contact with the sterile surgical drape around the incision site. The adhesive liner 432 is removed. The adhesive member 430 of the PEMS 400 is adhered to the sterile surgical draping on the chest 460 of the patient. This process is repeated with additional PEMS 400 until the all edges of the pericardium are covered by PEMS 400.

Referring again to FIG. 12A, in some implementations of the method 300, step 314 includes identifying the atrial-ventricular groove. In some implementations, the atrial-ventricular groove is identified using fluoroscopy. Multiple fluoroscopic images from various angles may need to be used to ascertain the location of the atrial-ventricular groove. In some implementations, the injection of a contrast solution into the pericardial space (e.g., between the pericardium and the epicardium) may enhance the visibility of the atrial-ventricular groove. The boundaries of other cardiac structures may also be determined in this step.

In some implementations of the method 300, the optional step 316 includes intra-operatively measuring the ventricular perimeter of the patient's heart. In some instances, the measurement may have already been performed pre-operatively using imaging modalities such as a CAT scan, MRI, ultrasound, and the like. In such instances, step 316 may be optional to perform.

Figure 14A:
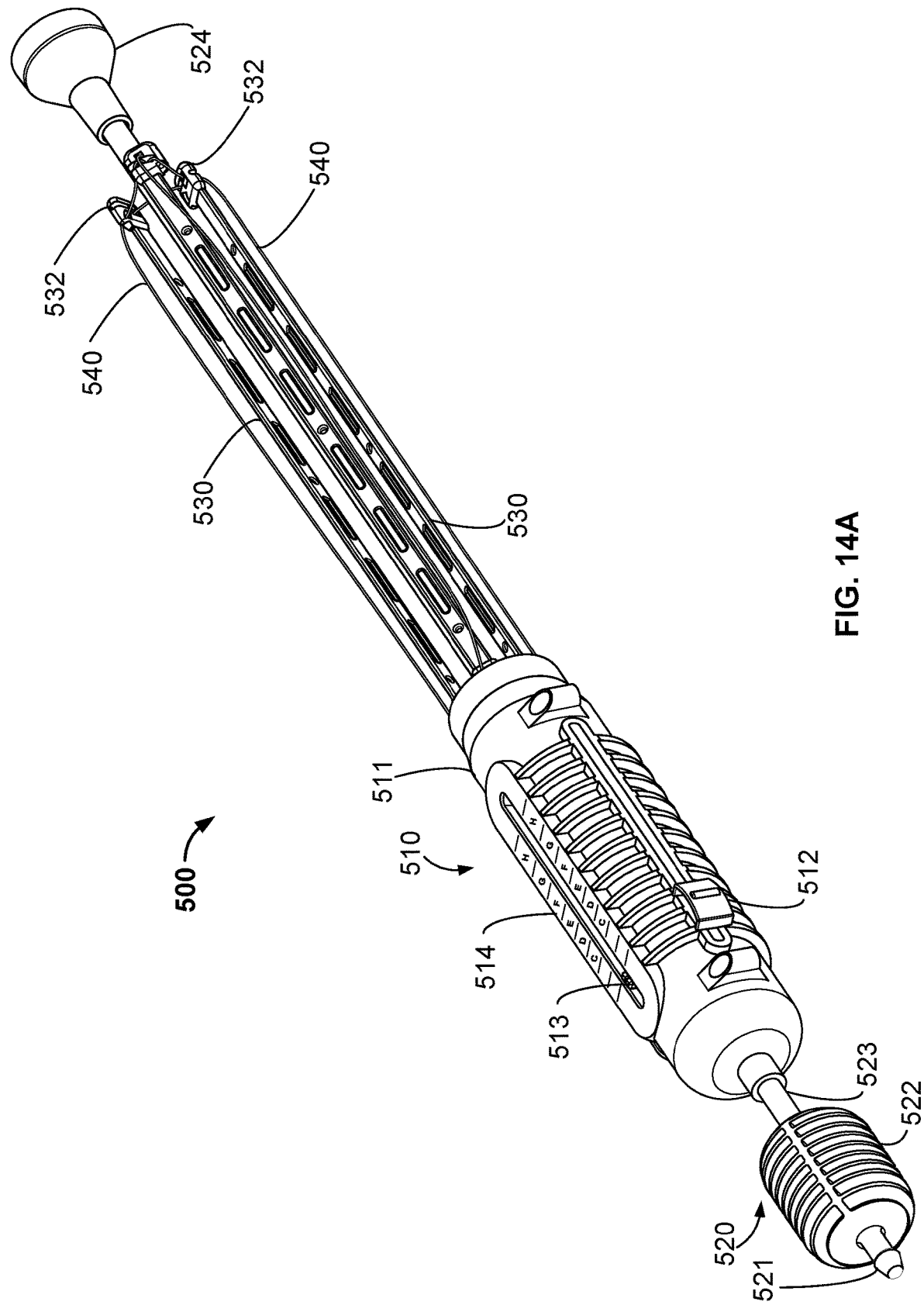
FIGS. 14A-14C are perspective top and side views of a device for measuring the size of a heart within the patient, in accordance with some implementations of the method of FIGS. 12A-12C.
Figure 14B:
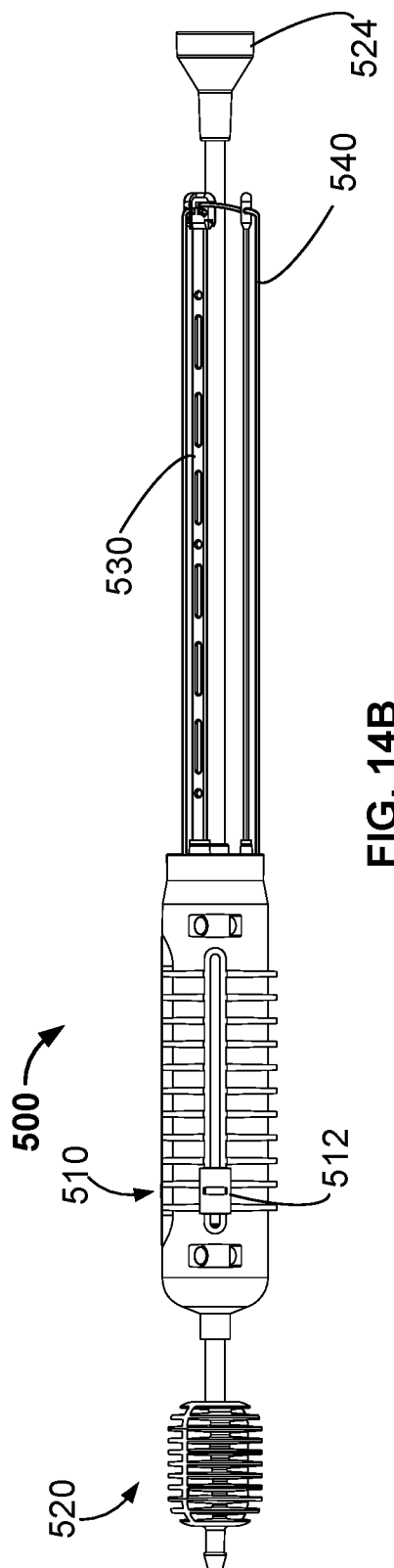
Figure 14C:
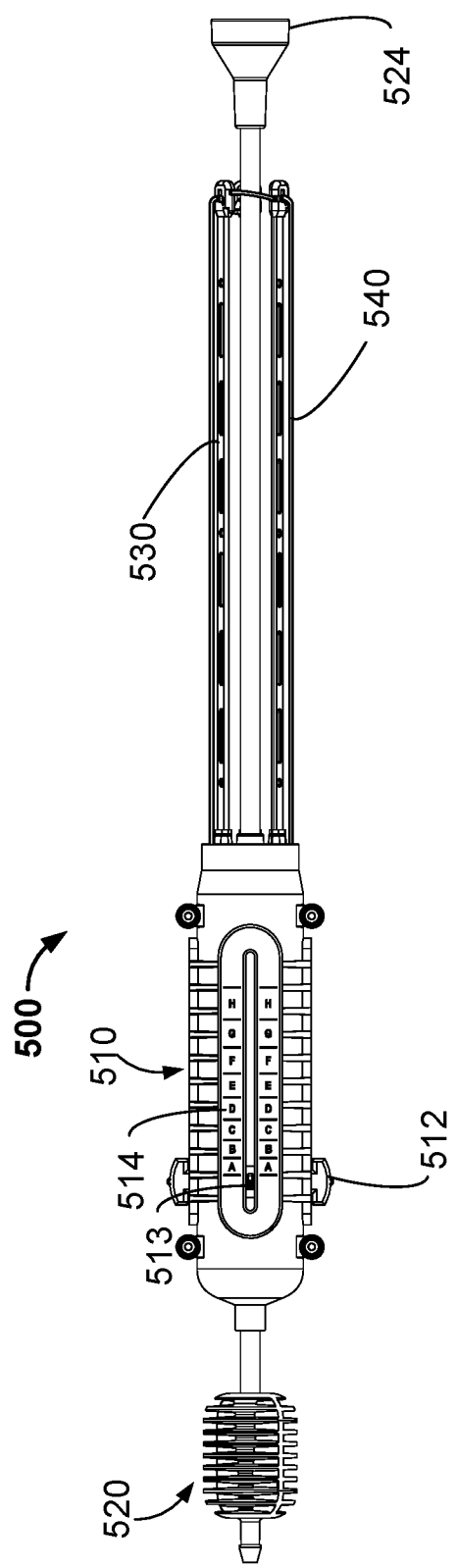

An example intra-operative sizing device 500 for performing step 316 is depicted in FIGS. 14A-14C. In some embodiments, the sizing device 500 includes a main body 510, a vacuum assembly 520, sizing arms 530, and sizing cords 540. The vacuum assembly 520 is slidable in relation to the main body 510. The arms 530 are fixed to the main body 510. The cords 540 (in the embodiment depicted there are three cords) are attached at one end to the end cap 532 of one of the arms 530, and at another end to a sizing positioner 512 in the main body 510.

In some embodiments, the main body 510 includes a casing 511, sizing positioners 512, a sizing indicator 513, and a sizing scale 514. The sizing positioners 512, which are linked to the sizing indicator 513, are slidable in relation to the casing 511. The sizing scale 514 is affixed to the casing. As the sizing positioners 512 are axially translated, the sizing indicator 513 moves in unison. The clinician can ascertain the measurement by viewing the sizing indicator 513 in relation to the sizing scale 514.

The sizing device 500 also includes a vacuum assembly 520. In some embodiments, the vacuum assembly 520 can include a vacuum fitting 521, a knob 522, a vacuum shaft 523, and a vacuum stabilizer cup 524. The aforementioned components of the vacuum assembly 520 are affixed to each other and axially translate in relation to the main body 510 as a unit. The vacuum fitting 52 is in fluid communication with the vacuum shaft 523, which is in fluid communication with the vacuum stabilizer cup 524. Hence, when a source of negative pressure is attached to the vacuum fitting, negative pressure is communicated to the vacuum shaft 523 and vacuum stabilizer cup 524.

In some embodiments, the sizing device 500 also includes multiple sizing arms 530. In the depicted embodiment, three arms 530 are included that are disposed at about 120 degrees apart from each other. In other embodiments, fewer or more arms are included. One end of the arms are affixed to the main body 510, while the other ends of the arms 530 are free ends having end caps 532. The arms 530 are laterally elastically flexible. That is, the arms 530 can radially deflect away from the vacuum shaft 523 while having one end affixed to the main body 510. As such, in some embodiments the arms 530 are made from a polymeric material such as Acrylonitrile Butadiene Styrene (ABS), Polyvinyl Chloride (PVC), Cellulose Acetate Butyrate (CAB), Polyethylene (PE), High Density Polyethylene (HDPE), Low Density Polyethylene (LDPE or LLDPE), Polypropylene (PP), Polymethylpentene (PMP), Polycarbonate (PC), Polypheneylene Ether (PPE), Polyamide (PA or Nylon), and the like. The end caps 532 include clearance holes through which a sizing cord 540 freely passes.

The sizing device 500 also includes sizing cords 540. In the embodiment depicted, three sizing cords 540 are included. In other embodiments, fewer or more cords are included. The cords can be comprised of a biocompatible material such as, but not limited to, PTFE, ePTFE, polypropylene, polyglycolide, nylon, and other like materials. Each cord 540 have two ends. A first end of the cords 540 is attached to the sizing positioners 512, and a second end of the cords are individually attached to an end cap 532. Therebetween, the cords 540 individually pass through a clearance hole in an end cap 532.

In one embodiment, the process for using the sizing device 500 is as follows. A source of negative pressure is connected to the vacuum fitting 521. The vacuum assembly 520 is fully extended in relation to the main body 510. The vacuum stabilizer cup 524 is inserted through the chest incision and placed in contact with the apex of the heart. The main body 510, and sizing arms 530 affixed thereto, are carefully advanced into the pericardial cavity so that the arms 530 and the cords 540 surround the heart. An imaging system, such as a fluoroscope, can be used to provide visualization of the advancement. As the arms and cords 540 are advanced, the sizing positioners 512 may move distally in relation to the main body 510 as the cords 540 require additional length to surround the heart. The advancement is stopped when the sizer cords 540 are around the largest perimeter of the heart. The sizer positioners 512 are then carefully pulled back (manually) to remove any slack in the cords 540. Using fluoroscopy, the clinician confirms that the cords 540 are not over-tightened (e.g., that the heart is not indented by the cords 540). The clinician then observes the relative position of the sizing indicator 513 to the sizing scale 514. The clinician can thereby ascertain the size of the largest perimeter of the heart, and thereafter remove the sizing device 500.

Referring again to FIG. 12A, in some implementations of the method 300, step 318 can include selecting an implant, which may be include selecting the implant based at least in part on the size of the patient's heart as determined previously. In some embodiments, the implant will be pre-loaded on a delivery device in sterile packaging, as previously described herein. The epicardial management strips may also be pre-loaded on the delivery device.

At step 320 in some implementations of the method 300, a source of negative pressure is connected to the delivery device. In the context of the example delivery device 200, the negative pressure is attached to vacuum connection fitting 232. The negative pressure will be communicated to the vacuum cup 238 of the heart stabilizer 230.

At step 322 in some implementations of the method 300, the vacuum stabilizer is fully extended. In the context of the example delivery device 200, the heart stabilizer 230 is fully extended in relation to the main body 210.

Figure 15:
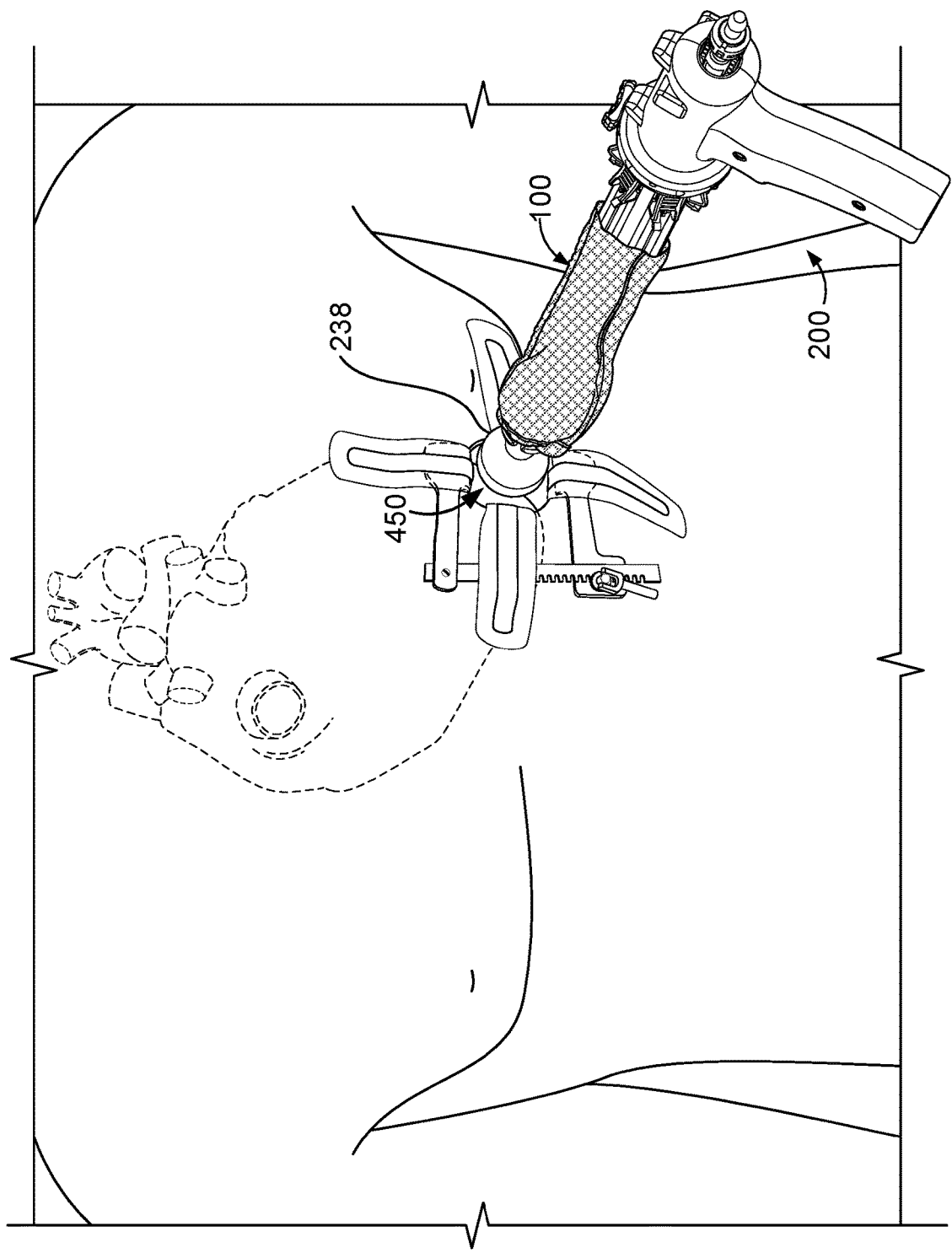
FIG. 15 is a perspective view of the introduction into a patient's chest cavity of an implant that is loaded on an implant delivery device, in accordance with some implementations of the method of FIGS. 12A-12C.

At step 324 in some implementations of the method 300, the vacuum stabilizer is inserted through the incision and into pericardial tunnel. An example of this step is illustrated in FIG. 15. There the vacuum cup 238 of example delivery device 200 is being inserted into the pericardial tunnel 450. The implant 100 is coupled to the delivery device 200.

Referring now to FIG. 12B, at step 326 the fillable bladder is rotationally aligned to a target location on the heart, in accordance with some implementations of the method 300. For example, in some instances the target location may be on the posterior lateral surface of the heart where the fillable bladder will be able to deflect the "P2" portion of the posterior leaflet of the mitral valve to treat FMR. Other target locations may be selected in other instances depending on the condition to be treated using method 300. In this step, the relative positioning between features of the delivery device and the fillable bladder can be used advantageously. In the context of the example delivery device 200, as explained above, the relative orientation of the fillable bladder 120 in relation to the pistol grip handle 212 of the delivery device 200 can have a predetermined orientation such that a clinician may be able to ascertain the position of the fillable bladder 120 based on the conveniently held position of the pistol grip handle 212 over the patient's body. Based on the known orientation, the clinician will be estimate the location of the fillable bladder 120 relative to the targeted surface region of the heart based on the orientation of the pistol grip handle 212 in the clinician's hand.

At step 328 in some implementations of the method 300, the vacuum stabilizer is applied to the apex of the patient's heart. The negative pressure at the delivery device is active at this step. Therefore, the vacuum stabilizer becomes attached to the apex using vacuum. The apex of the heart is thereby stabilized in relation to the delivery device.

At step 330, the arm actuators can be unlocked. In the context of the example delivery device 200, the clinician rotates the actuator lock ring 216, as previously described. Thereafter, all of the arm actuators 224 are not locked to the main body 210, and the arm actuators 224 can be slid in relation to the main body 210 and splined barrel 222 of the delivery device 200.

At optional step 332 in some implementations of the method 300, the heart can be temporarily elongated. The clinician can perform this step by exerting a slight directed pull on the delivery device in a proximal direction. Doing so may elongate the shape of the heart at the heart's apex and ease the initial deployment of the delivery tool's arms over the heart.

Figure 16C:
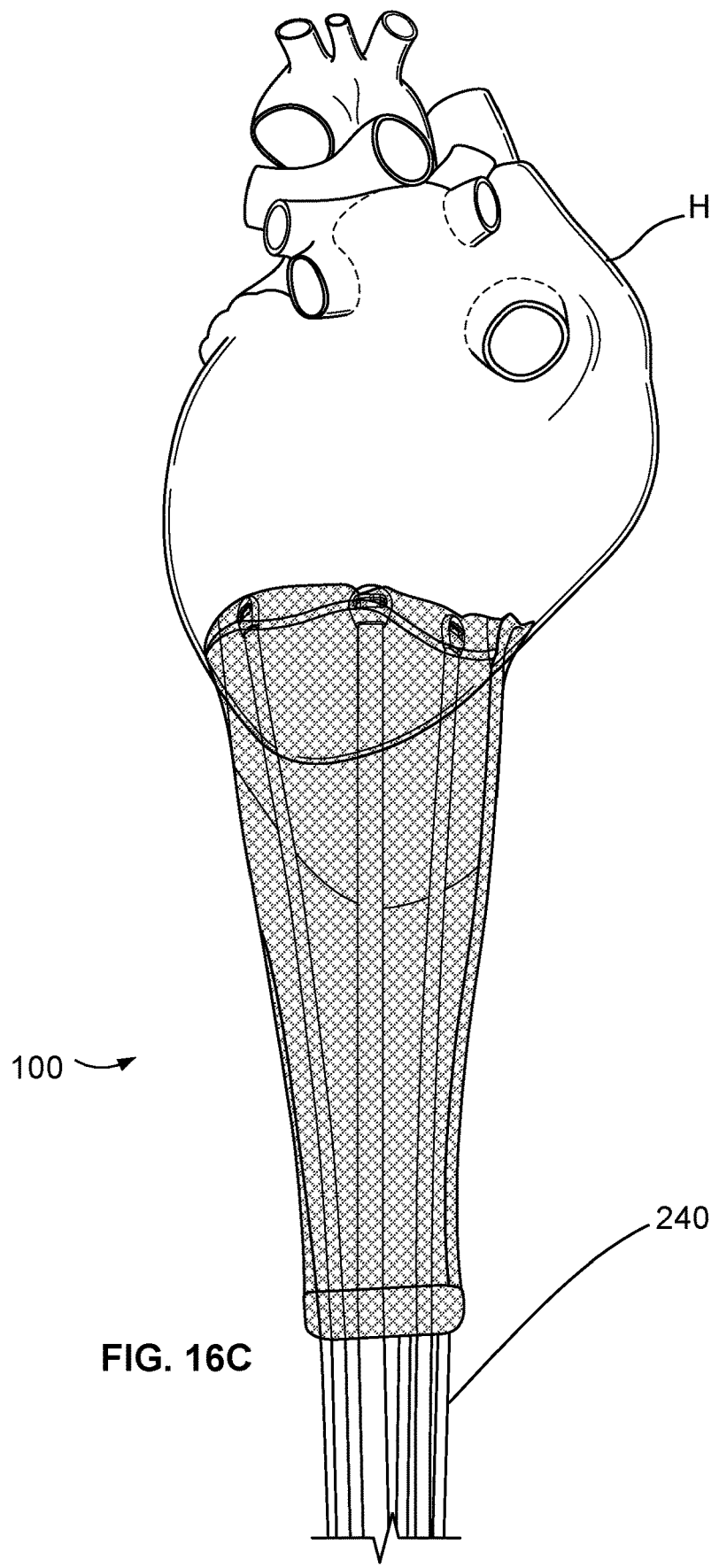

At step 334, the arms of the delivery device are incrementally extended while using imaging to view the position of the arms relative to the heart. FIGS. 16A-16C illustrate one non-limiting example of the step 334, in accordance with some implementations of the method 300. In FIG. 16A a clinician is shown operating a delivery device 200. The clinician is extending the arms 240 of the delivery device, incrementally and individually, by sliding the actuators 224 distally. Contemporaneously, the clinician is observing the video screen of an imaging system 600 (refer to FIG. 16B) whereby the clinician can view the positions of the arms 240 in relation to the heart H. In some implementations, the radiopaque markers of the implant 100 (described above) may also aid in the contemporaneous visualization process and to verify the positioning of the hem 113 and the bladder 120 relative to particular landmarks of the heart H. FIG. 16C illustrates an implant 100 that is coupled to arms 240 as the arms are being extended so as to position the implant 100 around the ventricles of the heart H. The arms 240 are advanced carefully, and in many circumstances, no single arm 240 is greatly advanced further than the others. For example, in some implementations it is recommended that no single arm 240 be positioned more than about 2 cm beyond any other arm 240. In some implementations, it may be advantageous to modulate the extension distance of the vacuum stabilizer in relation to the rest of the delivery device so as to achieve a desirable balance between flexibility and column strength of the arms during this step.

At step 336, the arms are further advanced to position the leading hem of the implant in the atrial-ventricular groove of the heart. This positioning of the implant in the atrial-ventricular groove is depicted in FIG. 1B, for example. As previously described herein, radiopaque markers may be mounted on the implant to assist with the contemporaneous visualization process and to verify the positioning of the hem 113 and the bladder 120 relative to particular landmarks of the heart H. In the context of the example delivery device 200, one or more radiopaque markers 115 located on the hem 113 and one or more radiopaque markers 125 of the bladder 120 can be used as reference points in conjunction with an imaging system.

At step 338, the delivery device is decoupled from the implant. In the context of the example delivery device 200, pivoting an actuator lever 226 of an arm actuator 224 can retract a core member 242 of an arm assembly 240 in relation to the outer jacket 241 and arm end 243 of the arm assembly 240 to decouple the arm assembly 240 from the implant 100. This process can be repeated for every arm assembly 240 to fully decouple the implant 100 from the delivery device 200.

At step 340 the arms of the delivery device can be retracted. For instance, using the delivery device 200 as an example, the arm actuators 224 can be slid proximally to withdraw each arm assembly while leaving the implant 100 on the heart H. The epicardial management strips 250 are also retracted along with the arms 240.

Figure 17:
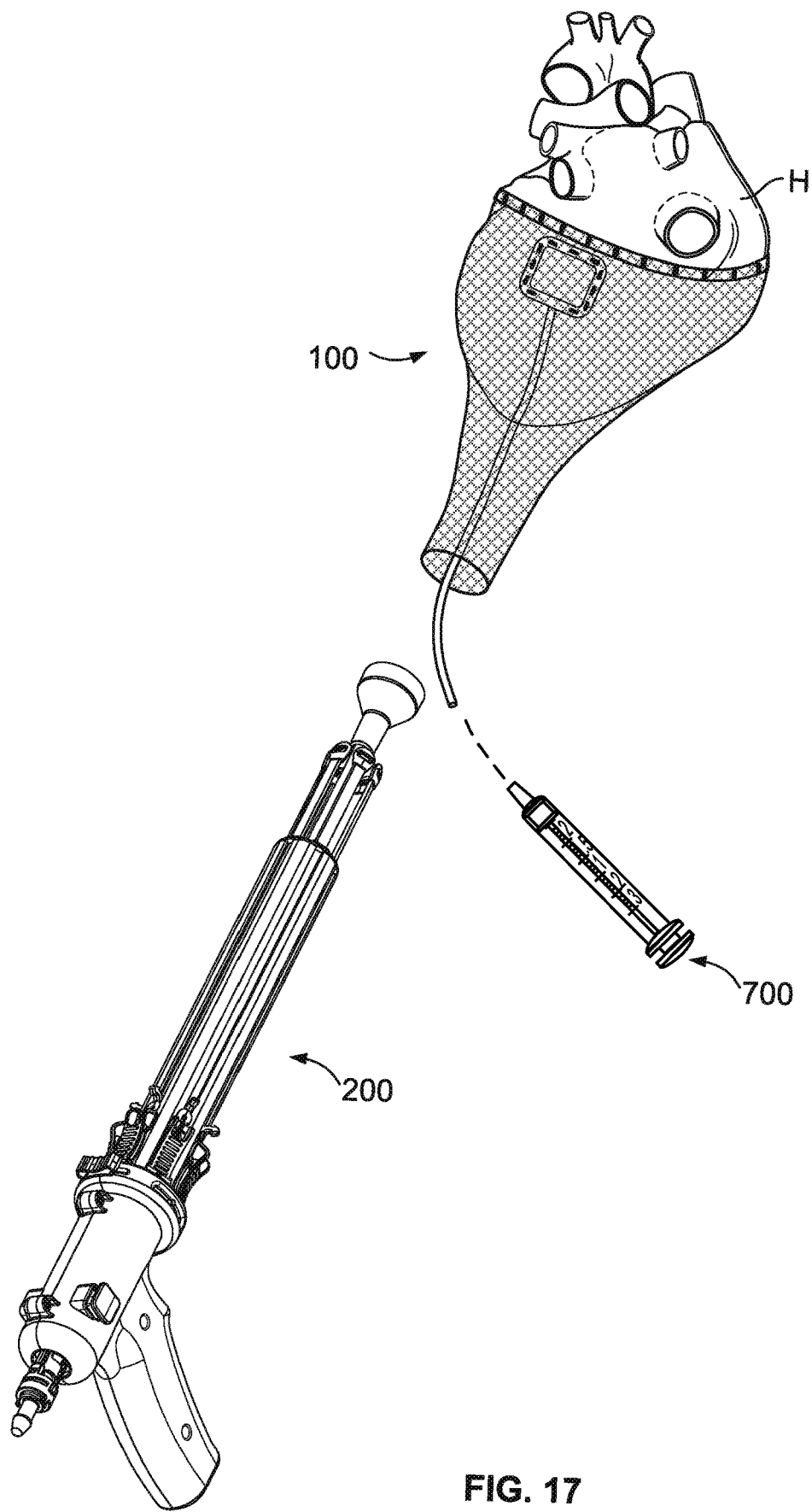
FIG. 17 is a perspective view of the withdrawal of an implant delivery device after installing an implant on the patient's heart, in accordance with some implementations of the method of FIGS. 12A-12C.

At step 342, the delivery device is withdrawn from the patient. The negative pressure source is discontinued, and then the entire delivery device is withdrawn. One non-limiting example of this step is illustrated in FIG. 17.

Referring again to FIG. 12B, at step 344 the fillable bladder(s) are inflated while patient parameters are monitored. Sterile saline solution or other types of inflation fluids may be used to inflate fillable bladders. For example, the inflation fluid can be dispensed from a syringe device or other inflation delivery device that is temporarily coupled to the proximal end opening of the tube. When the condition being treated is valvular regurgitation, the valve may be monitored using, for example, transesophageal echocardiography or other like techniques, while the inflation is taking place. Such contemporaneous monitoring may assist the clinician to determine the volume of inflation fluid to administer into the fillable bladder(s). This step is also illustrated in FIG. 17.

Referring again to FIG. 12B, at step 346, the inflation tube of the fillable bladder is sealed. For example, one or more ligation clips may be applied to the inflation tube to seal the tube (refer, for example, to FIGS. 1A and 1B).

Referring now to FIG. 12C, in some implementations of the method 300, step 348 may include flushing the pericardial cavity. For example, sterile saline solution can be injected and subsequently aspirated. This step can be performed to remove contrast agent substances that may have been injected earlier in the procedure. The injection and aspiration of the solution can be repeated multiple times, as desired, to flush the pericardial cavity.

At step 350, the pericardial edge management strips are removed. The removal can be performed by reversing the steps of the implementation procedure.

Figure 18:
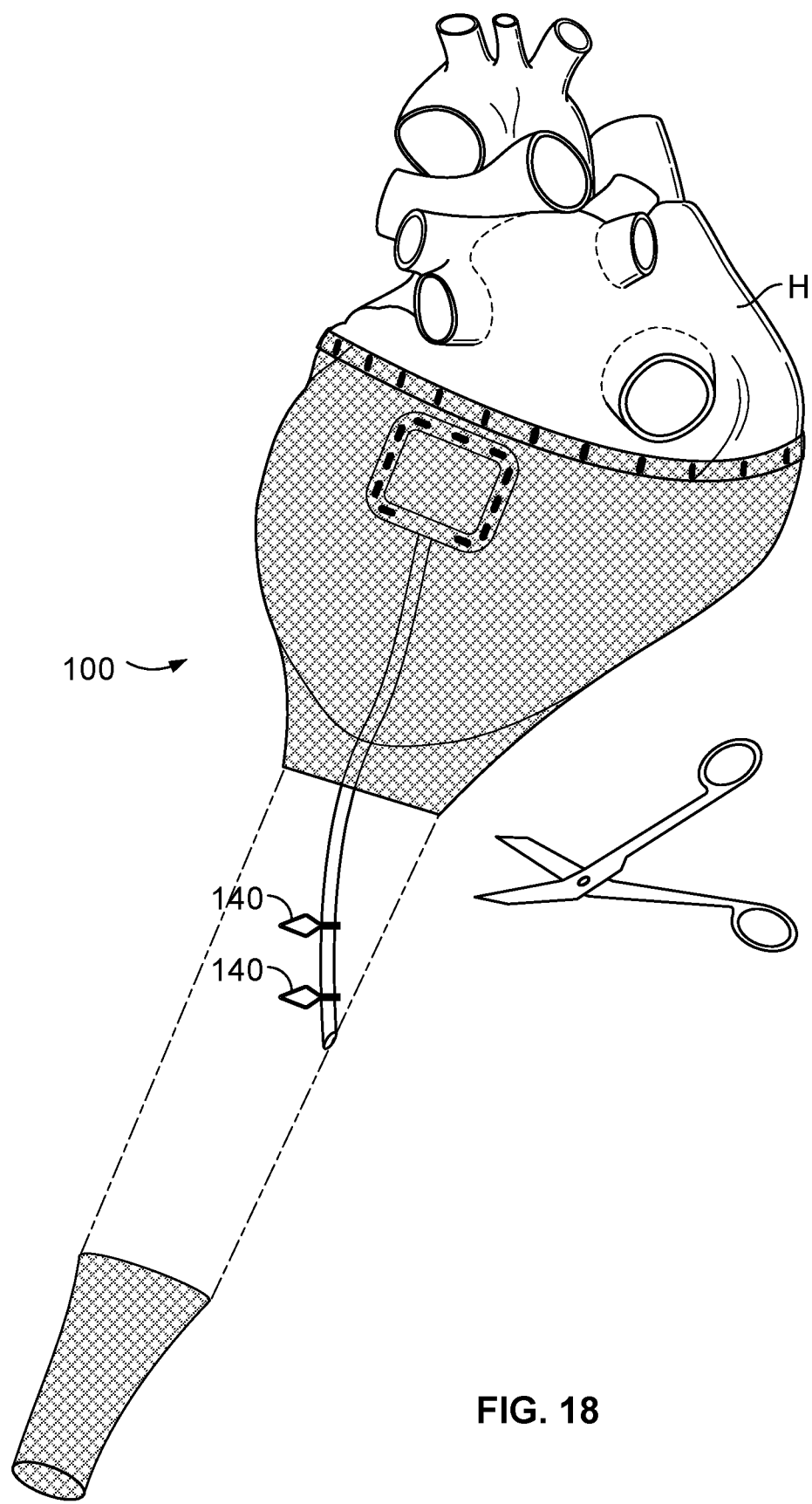
FIG. 18 is a perspective view of trimming of the implant after installing an implant on the patient's heart, in accordance with some implementations of the method of FIGS. 12A-12C.

At step 352, excess mesh material of the implant is trimmed. This step 352, like all other steps in some implementations of the method 300, may be performed while the heart is beating. In such circumstances, the clinician can carefully gather the trailing end material of the implant in the area of the chest opening. Using a scissors or other cutting device, the clinician can trim the excess material. Care is taken to ensure a sufficient amount remains with the implant to close the implant around the apex of the heart. One non-limiting example of this step is illustrated in FIG. 18.

Referring again to FIG. 12C, at step 354 the trailing end of the implant is closed around the apex of the heart. This can be performed by suturing the trailing end portion and cinching the material together like a purse string. The inflation tube remains extending through the cinched trailing end portion. One non-limiting example of this configuration is illustrated in FIG. 1B.

Referring again to FIG. 12C, at step 356 the pericardium is loosely closed. This step can be performed by installing a few sutures (e.g., two or three) to close the pericardium. Having a loose closure will facilitate drainage of fluids form the pericardium, as is common after a procedure such as this. The inflation tube remains extending through the loosely closed pericardium.

At step 358, the end of the inflation tube is aligned in an intercostal space and the chest incision is closed. Aligning the end of the inflation tube in the intercostal space may allow future access to the inflation tube via a simple cut-down procedure through the skin adjacent to the intercostal space between the ribs (e.g., the fifth intercostal space in some implementations). Future inflation or deflation of the fillable bladder may thereby be performed with a minimally invasive access to an intercostal space under the side without extensive surgery to access the pericardium or epicardium.

Figure 19:
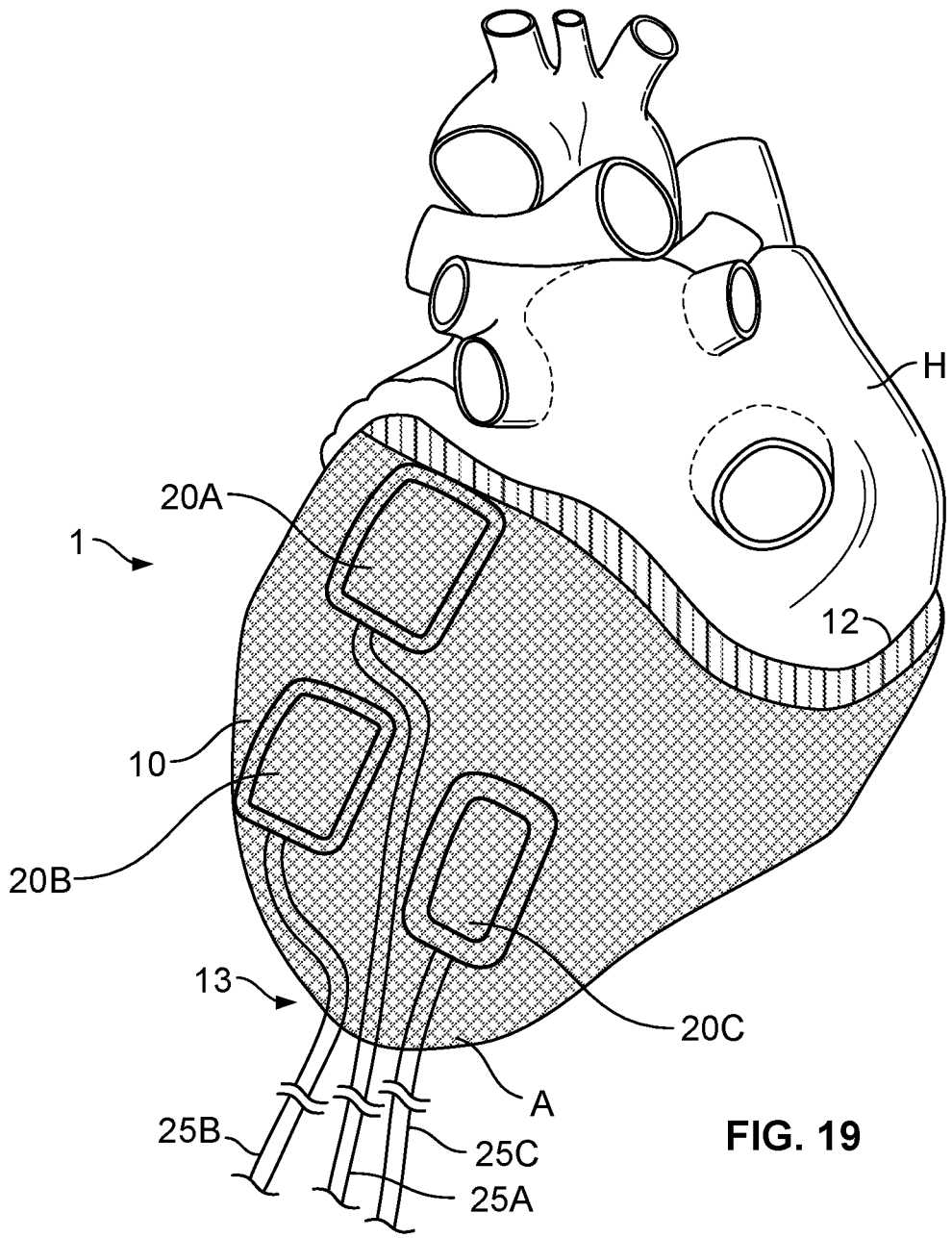
FIG. 19 is a perspective view of another implant for treating a heart including three optional bladder locations at the mitral valve, anterior papillary muscle, and posterior papillary muscle, in accordance with some embodiments.

Referring to FIG. 19, the heart H can be treated (e.g., to reduce FMR) using an implant 1 that includes a jacket 10 and multiple inflatable bladders that facilitate exertion of localized pressure on the epicardium at two or more particular strategic locations. In the depicted example, a first inflatable bladder 20A is positioned on the wall of the heart H near the mitral valve, e.g., at the P2 area of the mitral valve (in the center of the posterior leaflet) to reduce the distance across the valve, thereby potentially reducing the gap between the leaflets responsible for the regurgitation. Additionally, it may be advantageous to also exert localized pressure on the epicardium near papillary muscles from which chordae extend to the valve leaflets. For example, a second inflatable bladder 20B can be positioned to exert localized pressure to the wall of heart H resulting in an advantageous displacement of anterior papillary muscles. Further, in some cases a third inflatable bladder 20C can be positioned to exert additional localized pressure to the wall of heart H resulting in an advantageous displacement of posterior papillary muscles. In some cases, two and only two bladders 20A and 20B, or 20A and 20C are included as part of the implant 1. In some cases, all three bladders 20A, 20B, and 20A are included as part of the implant 1.

The inflatable bladders 20A, 20B, and/or 20C may be disposed on an interior surface of jacket 10. Bladders 20A, 20B, and/or 20C may or may not be attached to jacket 10. In embodiments wherein the bladders 20A, 20B, and/or 20C are attached to the jacket 10 prior to implantation of the implant 1, the implant may include one, two or all of the three bladders 20A-C. When bladders 20B and/or 20C are positioned adjacent to the papillary muscles, the bladders can be inflated to gently correct papillary muscle position and relieve tension on the chordae (which otherwise prohibits normal valve functioning).

Figure 20:
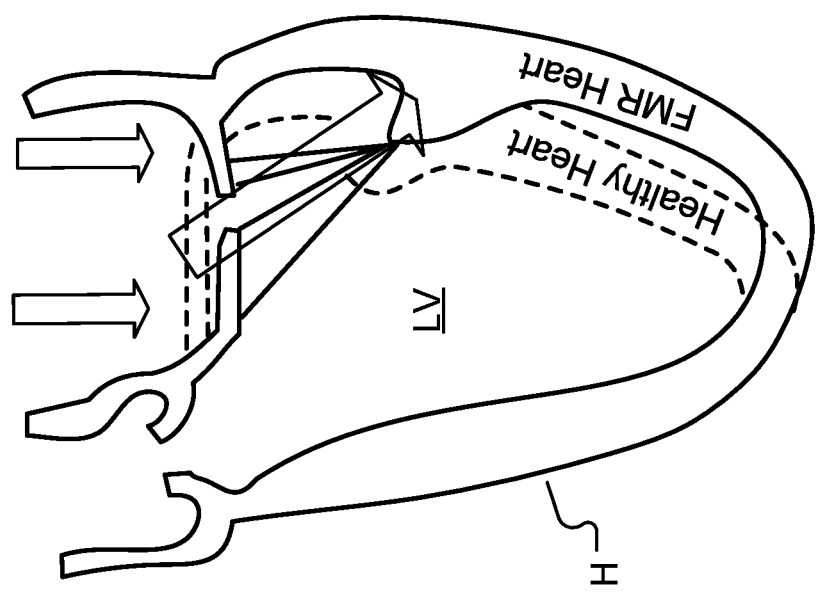
FIG. 20 is a cross-sectional view of an enlarged heart that has functional mitral regurgitation ("FMR").

Referring to FIG. 20, an enlarged heart H is shown in longitudinal cross-section. The enlarged left ventricle LV of the heart H is causing FMR in this example. Such FMR is occurring because the left ventricle LV is distorted or dilated (enlarged), displacing the papillary muscles and chordae that support the two mitral valve leaflets, thereby stretching the mitral valve opening (annulus) as depicted in FIG. 20.

Figure 21:
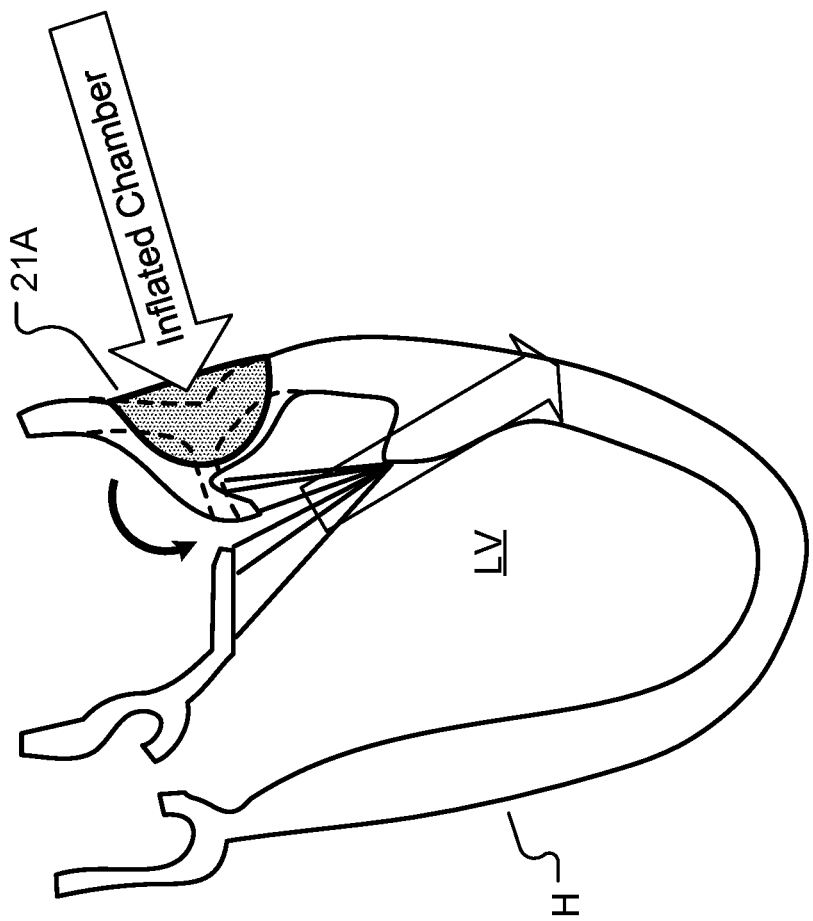
FIG. 21 shows the enlarged heart of FIG. 20 with a first inflated chamber exerting localized pressure on the epicardium near the annulus of the mitral valve.

Referring also to FIG. 21, a first fillable bladder 21A (e.g., coupled to the mesh body of a jacket at a specific location) can be used to exert a localized pressure on the posterior lateral surface of the heart H to thereby deflect the "P2" portion of the posterior leaflet of the mitral valve in an attempt to treat the FMR. While such a treatment may serve to reduce or eliminate FMR in some cases, in other cases (such as the depicted example) the effects of the distended left ventricle LV on the papillary muscles and chordae are not fully overcome by use of the single bladder 21A.

Figure 22:
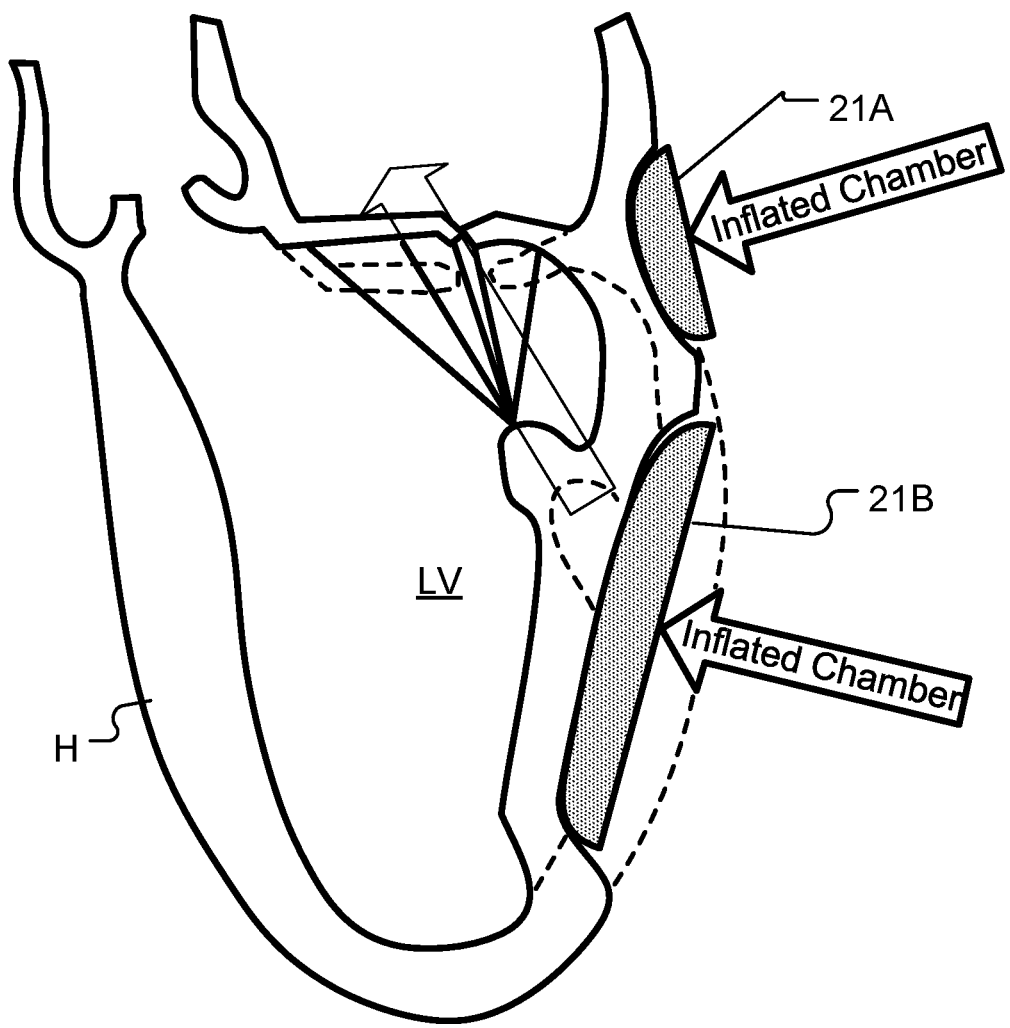
FIG. 22 shows the enlarged heart of FIGS. 20 and 21 being treated with the first inflated chamber at the mitral valve annulus and a second inflated chamber exerting localized pressure on the epicardium near the papillary muscles.

Referring also to FIG. 22, in some cases the effects of displaced papillary muscles and chordae that result from the distorted or dilated left ventricle LV can be counteracted by the use of a second fillable bladder 21B (e.g., coupled to the mesh body of a jacket at a specific location). The second fillable bladder 21B can exert localized pressure on the wall of the heart H adjacent to the effected papillary muscles. Accordingly, the second fillable bladder 21B can be inflated to gently correct papillary muscle position and relieve tension on the chordae (which otherwise prohibits normal mitral valve functioning). Such a concerted local pressurization on the heart H at: (i) the mitral valve annulus and (ii) the left ventricular wall at the location of effected papillary muscles, can be used to effectively reduce or eliminate FMR of an enlarged heart H in many cases.

Referring to FIG. 23, an example inflatable bladder 800 can be used with the cardiac implant devices (jackets) described herein. Inflatable bladder 800 is designed to have an extra-low profile when uninflated, and to be highly expandable in response to inflation. To achieve the highly expandable design, the inflatable bladder 800 has special side walls that are formed with undulations like a bellows. Such side walls make inflatable bladder 800 highly expandable.

The inflatable bladder 800 can be made of any of the materials, shapes, and can be made using any of the construction techniques that are described above in reference to fillable bladders, such as the fillable bladders 20 and 120. In some cases, the inner layer of the inflatable bladder 800 is more compliant than the outer layer of the inflatable bladder 800. Alternatively, in some cases the inner and outer layers of the inflatable bladder 800 are made of materials having the same compliance. In some such cases, the inflatable bladder 800 is expandable without stretching the materials of the layers. Such a design can provide enhanced fatigue resistance of the inflatable bladder 800 in some cases.

Referring also to FIG. 24, the inflatable bladder 800 (shown here in a transverse cross-section view) includes a base layer 810 and an expanding layer 820. The base layer 810 and the expanding layer 820 are bonded together (in a sealed manner) around the periphery of the inflatable bladder 800. In some embodiments, an intermediate layer is interposed between the base layer 810 and the expanding layer 820 around the periphery of the inflatable bladder 800. An inflation tube 830, which is in fluid communication with the interior space of the bladder that is defined between the base layer 810 and the expanding layer 820, extends therefrom. The inflation tube 830 is used to convey an inflation fluid into and/or out of the inflatable bladder 800.

The expanding layer 820 includes a peripheral side wall 822 and a pressure-exerting surface 824 positioned within the periphery of the peripheral side wall 822. The pressure-exerting surface 824 is generally planar. The peripheral side wall 822 includes one or more undulations (e.g., one, two as shown, three, four, five, six, or more than six undulations). The undulations act like the folds of a bellows (or an accordion) to allow the inflatable bladder 800 to transition between a low profile (as shown) to a substantially expanded profile. Moreover, the transition between a low profile to a substantially expanded profile can be accomplished without material stretching if so desired.

Figure 25:
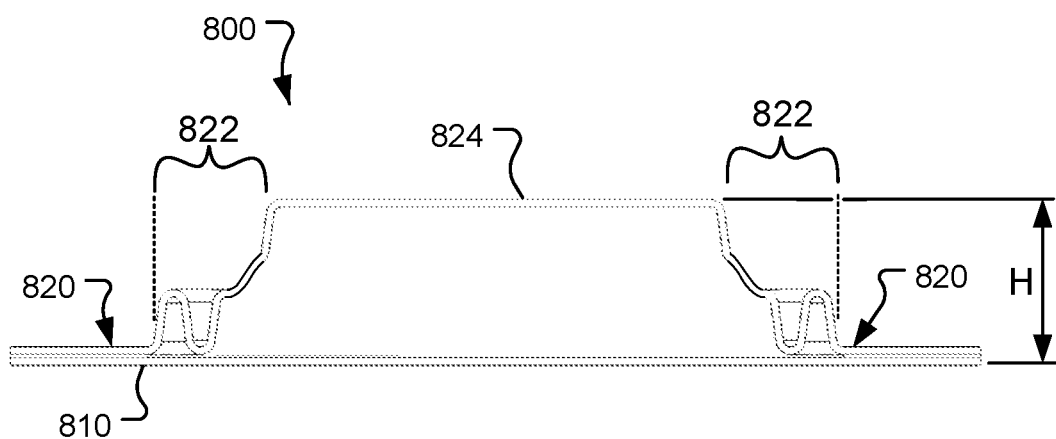
FIG. 25 is a cross-sectional view of the fillable bladder of FIG. 23 after a first stage of expansion of the bladder.

Referring to FIG. 25, the inflatable bladder 800 is again shown in a transverse cross-section view. Here, however, the inflatable bladder 800 has been inflated so that it is enlarged to a first expanded size. In this first expanded size, one of the undulations (folds) of the peripheral side wall 822 has unfolded in response to a pressure increase in the interior space of the inflatable bladder 800 from an infilling of an inflation fluid. As a result, the pressure-exerting surface 824 has moved away from the base layer 810. In this manner, pressure can be exerted by inflatable bladder 800 to a heart wall to treat conditions such as FMR.

Figure 26:
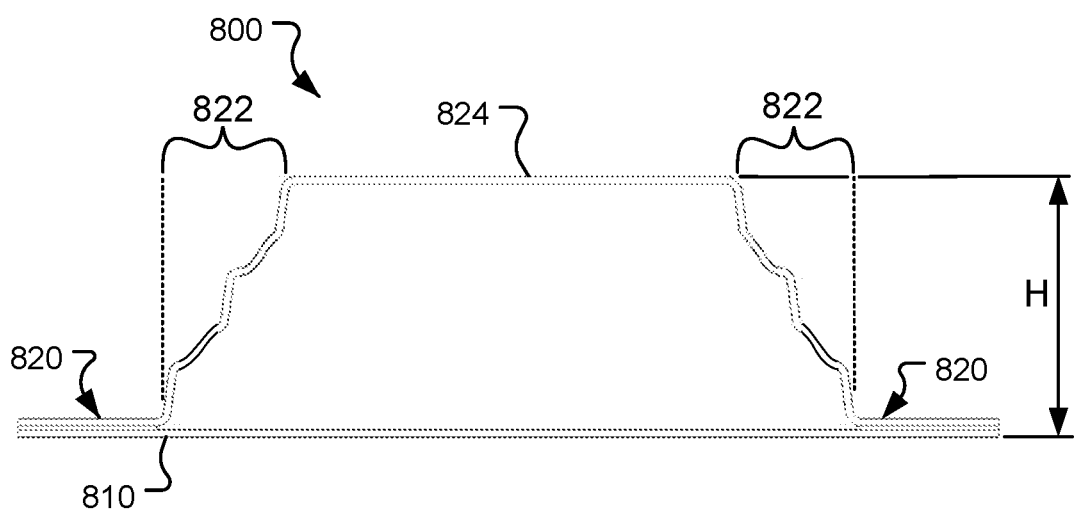
FIG. 26 is a cross-sectional view of the fillable bladder of FIG. 23 after first and second stages of expansion of the bladder.

Referring also to FIG. 26, if additional inflation fluid is added to the interior space of the inflatable bladder 800, the pressure-exerting surface 824 will move still farther away from the base layer 810. In the depicted arrangement, for example, the second undulation (fold) of the peripheral side wall 822 has unfolded in response to a pressure increase in the interior space of the inflatable bladder 800 from an additional infilling of an inflation fluid (in comparison to the arrangement of FIG. 25). It should be understood that, in some embodiments, the expansion of the inflatable bladder 800 as shown can occur without extension (stretching or elongation) of the materials of the pressure-exerting surface 824 and the base layer 810.

In one example embodiment of the inflatable bladder 800, the relationship between the volume of the interior space of the inflatable bladder 800 and the height H of the inflatable bladder 800 is as follows: when the volume is 20 ml the height H is 10.7 mm, when the volume is 40 ml the height H is 18.3 mm, when the volume is 60 ml the height H is 27.4 mm, when the volume is 80 ml the height H is 36.8 mm, when the volume is 90 ml the height H is 41.9 mm, and when the volume is 100 ml the height H is 44.2 mm (a more than four-fold increase compared to the initial height H of 10.7 mm). It should be understood that the foregoing data is just one example and that inflatable bladders can be designed to meet virtually any desired specifications. In some cases, when the interior space of the inflatable bladder 800 is filled, the pressure-exerting surface 824 will naturally tend to bulge outward slightly.

While in the depicted embodiment the dimensions of the two stages of expansion of the inflatable bladder 800 are about equal, such an arrangement is not required in all embodiments. For example, in some embodiments one or more stages of expansion can be a lesser distance than one or more other stages of expansion. The extent of expansions (dimensionally), relating to stages of expansion, can be controlled by the size of the undulation(s) of the peripheral side wall 822. The sizes of the undulations of an inflatable bladder do not need to all be the same size in a particular embodiment of the inflatable bladder 800.

Referring to FIG. 27, some embodiments of the inflatable bladders described herein (such as the depicted example inflatable bladder 900 having an undulated peripheral side wall 922) have a pressure-exerting surface 924 with a layer of fabric 926 attached thereto. The layer of fabric 926 can serve to promote tissue ingrowth and/or fibrosis of the epicardium. Accordingly, the attachment of the pressure-exerting surface 924 to the epicardial surface of a heart is thereby enhanced. For example, in some cases an inflatable bladder with a layer of fabric 926 attached to the pressure-exerting surface 924 is implanted adjacent to a heart. Then, prior to inflation of the inflatable bladder, the layer of fabric 926 is allotted time to attach to the epicardium by way of tissue ingrowth and/or fibrosis. The allotted time may be 1 week, 2 weeks, 3 weeks, 4 weeks, 5 weeks, 6 weeks, or more than 6 weeks, and any time period therebetween. After the allotted time for tissue ingrowth and/or fibrosis has occurred, then the inflatable bladder is inflated. The layer of fabric 926 can be made of any suitable material such as, but not limited to, Denier polyester, polytetrafluoroethylene (PTFE), expanded PTFE (ePTFE), polypropylene, and the like. In some cases, the layer of fabric 926 can be treated with chemical moieties to enhance tissue ingrowth and/or endothelialization.

In some embodiments, one or more of the inflatable bladders of the cardiac implant devices (jackets) described herein can be attached on an exterior surface of the mesh material of the cardiac implant. Such an inflatable bladder can either have an undulated peripheral side wall (such as the inflatable bladder 900 shown in FIG. 27), or not have an undulated peripheral side wall (such as the fillable bladder 120 shown in FIG. 3). For example, in some embodiments the cardiac implant includes three fillable bladders (e.g., refer to FIG. 19) and either one of the fillable bladders, two of the fillable bladders, or all three of the fillable bladders are attached on the exterior surface of the cardiac implant. In such an arrangement, the mesh material of the cardiac implant will be disposed between: (i) the fillable bladder(s) attached on the exterior surface of the cardiac implant and (ii) the exterior of the heart wall when the cardiac implant is positioned on a heart. The mesh material of the cardiac implant can thereby tend to facilitate tissue ingrowth and/or fibrosis of the epicardium with respect to the mesh material and the fillable bladder(s). That is, with the fillable bladder(s) attached on the exterior surface of the mesh material of the cardiac implant, the tissue ingrowth to the mesh material can serve to advantageously anchor the fillable bladder(s) in relation to the exterior of the heart wall.

A number of embodiments of the invention have been described. Nevertheless, it will be understood that various modifications may be made without departing from the scope of the invention. Accordingly, other embodiments are within the scope of the following claims.

What is claimed is:

1. A cardiac implant for implantation around an exterior of a heart, the implant comprising:
   an implant body comprising a mesh material in a tubular configuration that includes: (i) a leading end portion defining an open leading end configured to be positioned in an atrial-ventricular groove of the heart and (ii) a trailing end portion defining an open trailing end of a diameter that is less than a diameter of the open leading end; and
   a first fillable bladder comprising a base layer and an expanding layer, the expanding layer comprising a peripheral side wall and a pressure-exerting surface positioned within a periphery of the peripheral side wall, wherein the peripheral side wall comprises two or more concentric folds positioned interior to a peripheral edge of the first fillable bladder and configured for unfolding in response to pressurization of the first fillable bladder,
   wherein, when the two or more concentric folds are in a folded configuration, a height of an apex of each of the two or more concentric folds relative to the base layer is substantially equal to a height of the pressure-exerting surface relative to the base layer, and
   wherein the first fillable bladder is coupled to the implant body in a manner that the pressurization of the first fillable bladder increases pressure exerted by the first fillable bladder to the exterior of the heart.

2. The cardiac implant of claim 1, wherein the pressure-exerting surface is generally planar.

3. The cardiac implant of claim 1, wherein a height of the first fillable bladder is defined between the base layer and the pressure-exerting surface and the unfolding of the two or more concentric folds in response to the pressurization of the first fillable bladder increases the height of the first fillable bladder.

4. The cardiac implant of claim 1, wherein the first fillable bladder is configured to exert pressure to the exterior of the heart adjacent to a valve or papillary muscle of the heart.

5. The cardiac implant of claim 1, wherein the first fillable bladder is attached to the implant body.

6. The cardiac implant of claim 1, wherein the first fillable bladder is attached to an interior surface of the implant body.

7. The cardiac implant of claim 1, wherein the first fillable bladder is attached to an exterior surface of the implant body.

8. The cardiac implant of claim 1, wherein the first fillable bladder is separate from the implant body and not attached to the implant body.

9. The cardiac implant of claim 1, further comprising a second fillable bladder, wherein the first fillable bladder is configured to exert pressure to the exterior of the heart adjacent to an annulus of a heart valve of the heart, and wherein the second fillable bladder is configured to exert pressure to the exterior of the heart adjacent to papillary muscles of the heart valve.

10. The cardiac implant of claim 9, further comprising a third fillable bladder, wherein the third fillable bladder is configured to exert pressure to the exterior of the heart adjacent to anterior papillary muscles of the heart valve, and wherein the second fillable bladder is configured to exert pressure to the exterior of the heart adjacent to posterior papillary muscles of the heart valve.

11. The cardiac implant of claim 9, wherein the heart valve is a mitral valve or a tricuspid valve.

12. The cardiac implant of claim 1, wherein the peripheral edge of the first fillable bladder does not comprise folds.

13. The cardiac implant of claim 1, wherein the two or more concentric folds are spaced apart from the peripheral edge of the first fillable bladder.

14. The cardiac implant of claim 1, wherein the base layer and the expanding layer are bonded together around a periphery of the first fillable bladder.

15. The cardiac implant of claim 1, further comprising an intermediate layer interposed between the base layer and the expanding layer around a periphery of the first fillable bladder.

16. The cardiac implant of claim 1, wherein the two or more concentric folds are configured to facilitate expansion of the first fillable bladder without extension of a material of the first fillable bladder.

\* \* \* \* \*